(12) United States Patent
Smith et al.

(10) Patent No.: US 9,078,841 B2
(45) Date of Patent: Jul. 14, 2015

(54) PARASITE VACCINE

(75) Inventors: William David Smith, Penicuik (GB); George Fredrick James Newlands, Penicuik (GB); Stuart Smith, Penicuik (GB); Aileen Halliday, Penicuik (GB)

(73) Assignee: Moredun Research Institute, Penicuik (GB)

( * ) Notice: Subject to any disclaimer, the term of this patent is extended or adjusted under 35 U.S.C. 154(b) by 0 days.

(21) Appl. No.: 13/516,909

(22) PCT Filed: Dec. 20, 2010

(86) PCT No.: PCT/GB2010/002298
§ 371 (c)(1), (2), (4) Date: Nov. 15, 2012

(87) PCT Pub. No.: WO2011/073630
PCT Pub. Date: Jun. 23, 2011

(65) Prior Publication Data
US 2013/0064853 A1  Mar. 14, 2013

(30) Foreign Application Priority Data

Dec. 18, 2009 (GB) .................................. 0922099.7

(51) Int. Cl.
*A61K 39/00* (2006.01)
*A61K 39/002* (2006.01)
*C07H 21/04* (2006.01)

(52) U.S. Cl.
CPC ........... *A61K 39/0003* (2013.01); *A61K 39/002* (2013.01); *A61K 2039/552* (2013.01); *A61K 2039/55577* (2013.01)

(58) Field of Classification Search
USPC .............................. 424/9.1, 9.2, 184.1, 265.1
See application file for complete search history.

(56) References Cited

PUBLICATIONS

Vercauteren, I., et al. Infection and Immunity, vol. 72, No. 5, pp. 2995-3001, May 2004.*
Hilderson, H., et al. International Journal of Parasitology, vol. 25, No. 6, pp. 757-760, 1995.*
International Search Report and Written Opinion, PCT/GB2010/002298, mailed Aug. 6, 2011.
De Maere V et al. An aspartyl protease inhibitor of Ostertagia ostertagi: molecular cloning, analysis of stage and tissue specific expression and vaccine trial. Molecular & Biochemical Parasitology. May 1, 2005; 141(1): 81-88.
Wedrychowicz H et al. Surface and excretory/secretory antigens of fourth-stage larvae and adult *Ostertagia circumcincta*. Veterinary Parasitology; May 1994; 53(1-2): 117-132.
De Maere V et al. Identification of potential protective antigens of Ostertagia ostertagi with local antibody probes. Parasitology. Oct. 1, 2002; 125(4):383-391.
Smith WD et al. Evaluation of immunization with gut membrane glycoproteins of Ostertagia ostertagi against homologous challenge in claves and against *Haemonchus contortus* in sheep. Parasite Immunology, 2000; 22: 239-247.
Geldhof P et al. Vaccine testing of a recombinant activation-associated secreted protein (ASP1) from Ostertagia ostertagi. Parasite Immunology. 2008; 30: 57-60.
Halliday AM and Smith WD. Protective immunization of calves aginst Ostertagia ostertagi using foruth stage larval extracts. Parasite Immunology. 2010; 32; 656-663.

* cited by examiner

*Primary Examiner* — Rodney P Swartz
(74) *Attorney, Agent, or Firm* — Myers Bigel Sibley & Sajovec, P.A.

(57) ABSTRACT

The present invention provides one or more antigens from the fourth stage (L4) larvae of non-blood feeding parasitic nematodes, for raising an immune responses in an animals, in particular bovines. The invention further provides methods of making immunogenic and/or vaccine compositions.

24 Claims, 11 Drawing Sheets

SEQUENCE LISTING

<160> NUMBER OF SEQ ID NOS: 201

<210> SEQ ID NO 1
<211> LENGTH: 773
<212> TYPE: DNA
<213> ORGANISM: Ostertagia ostertagi
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t

<400> SEQUENCE: 1

| | | | | | |
|---|---|---|---|---|---|
| ctatcntatt | catcgcgcgc | ancccgggta | taacgaggac | gtcatgtccg | gctttgtncc | 60
| gctttcttca | ccttcttcgt | agcgctttac | gtcaggaatg | tgccaaccat | cgaagacttc | 120
| gctgttcgat | cgatcccaaa | ggaagctcag | gagctgactg | gtgaagcgct | agcggagata | 180
| tgtgaacagg | cagcagccgt | ttcaaggcca | tgtattcgcc | aaatgtggag | cgtcgtatgg | 240
| caagtttgat | gaacacactg | gaatacctcg | agaaaagcaa | gcgtcaattg | aaaatgaaaa | 300
| tgccagaaaa | agccataaac | aacgacacgc | tccctgaaag | tttcgacagt | cgggagcaat | 360
| ggaaggactg | cccctctcta | cagtacgttc | gcgatcagcc | acactgtggc | tcctgttggg | 420
| ctgtctcggc | tgcgagcgct | atgtccgatc | gactccgtat | acagacgaac | ggcaagaata | 480
| aggtgattct | ctcggacact | gacatccttg | catgttgtgg | agaattttgt | ggacttggat | 540
| gtgaaggagg | atacccctca | caagcctggg | aatttgccca | aggaatggc | cgtgtgcagt | 600
| ggaggatggg | atggtgaaaa | gggtgtgtgt | aaaccatatc | ctctccatcc | atgtggaaag | 660
| cacgaaaatc | agactttcta | tggcgaatgt | ccagaccaca | cgtacagaac | tccggcgtgc | 720
| aagaagtact | gccaatatgg | atacgacaag | cgctatgata | atgataaagt | cta | 773

<210> SEQ ID NO 2
<211> LENGTH: 328
<212> TYPE: DNA
<213> ORGANISM: Ostertagia ostertagi
<220> FEATURE:
<221> NAME/KEY: misc_feature
<222> LOCATION: (9)..(9)
<223> OTHER INFORMATION: n is a, c, g, or t

<400> SEQUENCE: 2

| | | | | | |
|---|---|---|---|---|---|
| catcggccnt | aggcgggggt | atgaagaata | tcgacaaaga | cgatacttgc | gttatgtatt | 60
| ctgtgctggc | gtatgacgca | accagtgaaa | ttcacgaaac | tattgtgatg | gttctcataa | 120
| agaatgagac | gggaaaagtc | agatctcact | acttcaagta | tcaggtgata | actgataaga | 180
| caacaaagaa | acaaagcact | tggattgacg | acatggacgc | gcttaatttc | atgttaacga | 240
| taagaaagtg | taagctcgtc | ccttctagag | gttaaaatcc | gtcttgaatg | aatggacatg | 300
| gaaataaatt | ttcgcagctg | taagaagg | | | | 328

<210> SEQ ID NO 3
<211> LENGTH: 355
<212> TYPE: DNA
<213> ORGANISM: Ostertagia ostertagi
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (348)..(349)
<223> OTHER INFORMATION: n is a, c, g, or t

<400> SEQUENCE: 3

```
accgggaaat cggcatccgc gggtttaagc tttacaccga ttccatctat tgtgtcgctg      60
tttgagatta ttccgaaaaa tgtgcatgag gagcagaaca gaaagagta tctggagatg      120 gttaccgaga aaatggagtg cttgctagaa gatcttcttc actgtcatga tcgaaatgtg    180
aaaagtcgtg gaaagaaatc agccgtctag gttttaatac caaacttgct tcccagggag     240
gtcttccaga aaatgcccaa ctttctcgaa aagttttttt tttgcatgat gtanaggtac      300
atgcatggaa gccagaattg tggctcatct ttcctgagcg gccctgtnna atacc          355
```

<210> SEQ ID NO 4
<211> LENGTH: 359
<212> TYPE: DNA
<213> ORGANISM: Ostertagia ostertagi
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t

<400> SEQUENCE: 4

```
tacaaatcgg aagtgacccc agtnantaca atgttctagg caagcgatca tcgtccaact      60
cctcaaacag ccccagccag gatccactac caccgagaac tcctcttccg cttgatttct     120
ggatattccg gtaaagcccc atgggtattg aantggacta tacaacctgc tcacatatat     180
gtcaacactg ttagagtctg ctatgatcgg tctactgagg atctattgcc caaagttatg     240
taatctgtgc tatcgtcgtc tttacatcaa ttttttatttg atcactgtat gatatgggag     300
ggatgtttga atagtagaga aagtgtagta gtataaataa atacctcata catacacag      359
```

<210> SEQ ID NO 5
<211> LENGTH: 258
<212> TYPE: DNA
<213> ORGANISM: Ostertagia ostertagi
<220> FEATURE:
<221> NAME/KEY: misc_feature
<222> LOCATION: (29)..(29)
<223> OTHER INFORMATION: n is a, c, g, or t

<400> SEQUENCE: 5

```
gccgggatct ggcacttacg gccggggtna ggaggaattg ttaaaatcct tcaaaacaag      60
cgaggagagc cactagatga tgatgaaatc aaggccatgt acaaggctaa gccaccaatc     120
gagaacggtg aagtcgacta caaggcattc gcacatctca tcactaccgg agctcaagac    180
gaactcactg ccgcataaac gttccttcaa tcatttgtgt gtgtctttga tcgaatcgga     240
tgaaagagaa atggccag                                                   258
```

<210> SEQ ID NO 6
<211> LENGTH: 581
<212> TYPE: DNA
<213> ORGANISM: Ostertagia ostertagi
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature

```
<222> LOCATION: (20)..(20)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t

<400> SEQUENCE: 6
gcgggaattt gggnactgan ggcgggatag ctagctngca acaacatgtg gatcaaaacc     60
gtcaccctg  aaggagaggt taccaagtgt agactggaca gatgtttacc agcaacgccc   120
gaaatgctgt cggtatttct gaaccaggat accttacaca tgaggcggtt cagtggtcag   180
aaacacaggg acattggtac ttccttccta gaaaggagtc aaagactgtc tacgtagaag   240
aagaggatga gacgaaaggc acggatctcc tgattactgg aaatccggac cttgaccaat   300
tcgaagtcaa gaggatagga atactgcgac ccgaacgcgg atattcggca ttcgatttta   360
ttcctggtac cgacgacaag atcatcgttg ccttgaagtc aaagaagtg accgacgagc    420
cagtcgaaac ctacatcaca gtatttacca ctgacggtca actcctactt gatgatcaga   480
aactcgacgg caactacaaa tttgagggac tctacttcat ttgaattttc cctcgtcatg   540
aaaagtgtca aatgttggct aacaataaat aattttatag c                       581

<210> SEQ ID NO 7
<211> LENGTH: 641
<212> TYPE: DNA
<213> ORGANISM: Ostertagia ostertagi

<400> SEQUENCE: 7
ttaaacagct tctactactg aagcttcgac cactactgtt ccgtatgagg aggacaacca     60
gatatgccca catcaccgtg gcatgaaaga cacattaaga ataagggcat tagtggctca   120
caattatcgg aggtcaaggc ttgctatggg gcttgtcaga aacaggagag gaagaacact   180
gccaacggcg tccaacatga gacatttgtc ctcaaaaaga acattttcca cgacgacagc   240
gcaccacatc cacagagcag tgatacctcc tatcactgac aattattgaa tacaattgca   300
caagtgaagc atatgccata caaaatgcgg tgaggtgctc tgtagttcca ccttcgacaa   360
tgccttcttt tgtccaagaa aaccgccata tggttttaaa gtctttagca aacactaagg   420
agaaagcgct tatagttccg acttcacggc cgatcacgtc tggtgaaatg cactttcaca   480
atgctattga ttatgatatc atacatttca acttattgtg ctcgaaaagt gacagtttct   540
gagggcgag  atgagctcaa ctgcatagcc actagtgcat cttgcacagc ggaaacacca   600
cgagttattc cttctgcctg gctaccgtac caatgttgca t                       641

<210> SEQ ID NO 8
<211> LENGTH: 469
<212> TYPE: DNA
<213> ORGANISM: Ostertagia ostertagi
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 8
gccgggaatt cggnaccgcg gntttgcgaa gtgctcctgg aagttgctgg tcgtgatgcc     60
actgaggcct tgaggacgt  cggtcattct acagatgctc gtgagaatga gggagcaata   120
```

| | |
|---|---|
| tcttgtcgga gatattgctg acgaggagaa gcagcaatat tcgtatgata agaaggaatg | 180 |
| ggtgaccagc cccagcgata ataaacaaag ggactcgaac ccgtgggcag cattggacaa | 240 |
| atacatctat cctgctctgt tcgccatcgt cttcgccctt atttactacc ttatcacaaa | 300 |
| ctagatttct gcttttgaa gtagatttgg gttttatttc ttcatgttcc gatttcttgg | 360 |
| attgtcactt aaatgtttca catttgcatg taccggtata tcagttttta tccgttgcac | 420 |
| gatatattat agttaaggtt tgtggtctaa cattgttagg aataaaagt | 469 |

<210> SEQ ID NO 9
<211> LENGTH: 253
<212> TYPE: DNA
<213> ORGANISM: Ostertagia ostertagi

<400> SEQUENCE: 9

| | |
|---|---|
| cgatcggcat tacggcgggt atatggaacg aggacttgac cccaagctgt ggaaggactt | 60 |
| ctgggatatc ttcgagaagt tcctggagaa ccgcaagcca ctaactgctg accagaaggc | 120 |
| tgcgcttgat gcgatgggca caagattcaa cgatgaagct caggaagcga actggccgtc | 180 |
| cttggacttc cacacacata agaaactctc ttgggaaatg cctaggtctt gatgcgtcag | 240 |
| tgaataaagt atg | 253 |

<210> SEQ ID NO 10
<211> LENGTH: 301
<212> TYPE: DNA
<213> ORGANISM: Ostertagia ostertagi

<400> SEQUENCE: 10

| | |
|---|---|
| gccgggaatc ggcactacgg ccgggttagc gatgaagaaa atcgaagatc acaacacgct | 60 |
| tgtcttcatc gttgatgtgc gagcgaacaa gcaccaaatt cggcagctg tgaagaagtt | 120 |
| gtacaagtat tgaggtgcaa aagattaaca cacttatcac tccccgttat ggagaaaaag | 180 |
| gcctacattc gcgtgtgacg acggattatg atgccttaga ttgcgccaat aagatcggaa | 240 |
| tcatatgaat tcttgttgtt ttgttatgaa tggttgataa atttgggtta attgaacaag | 300 |
| g | 301 |

<210> SEQ ID NO 11
<211> LENGTH: 325
<212> TYPE: DNA
<213> ORGANISM: Ostertagia ostertagi
<220> FEATURE:
<221> NAME/KEY: misc_feature
<222> LOCATION: (292)..(292)
<223> OTHER INFORMATION: n is a, c, g, or t

<400> SEQUENCE: 11

| | |
|---|---|
| ggccggggt atcggaagga aagcatattc agacaaaagc acgagtctag cccaatcaga | 60 |
| cacttcactc tgatggcatg ggcaaccacc gaatacattg gatgcgctgt gtcgctcgct | 120 |
| cgtgccccag gcgagtggta tattgtatgt cactacagaa acggaggtaa tacttgtaaa | 180 |
| cgaacacgtt tacatgccag ggtcccacat gttcagactg atcccacaag ctaccactgt | 240 |
| ggcgcggaca agtagtagca cgaaatctta aacagcctcc atgcttatat anagctaata | 300 |
| aaaggaaaat aaagttataa cgagc | 325 |

<210> SEQ ID NO 12
<211> LENGTH: 412
<212> TYPE: DNA
<213> ORGANISM: Ostertagia ostertagi

```
<220> FEATURE:
<221> NAME/KEY: misc_feature
<222> LOCATION: (19)..(19)
<223> OTHER INFORMATION: n is a, c, g, or t

<400> SEQUENCE: 12
gccgggaatt ggcattacng cgggttggga ttagtttgtg atgaagtttc ataacagtgt      60
ctatgtttat gataagttga tgatgagtgc tgtgttttt  ttaatatttt ttggtgttaa     120
tttgactttt tttcctttgc attttgctgg tttgcacggt tttcctcgta agtatataga    180
ttatccggat gtttattctg tgtgaaatgt tatatcttcg tatggttcaa tagtaagtgt    240
ttttgctttg ttttggtt  ttgtatgtgt tgttagaatc ttttttagt  tatcgcttag    300
tgttggttga taattttggt aaacagcaga cccgagtata gttatagcag ttatgttttg    360
ggtcacagtt atcagagtga tatttatttt agaagtgctg tgttaaaaaa tt            412

<210> SEQ ID NO 13
<211> LENGTH: 437
<212> TYPE: DNA
<213> ORGANISM: Ostertagia ostertagi

<400> SEQUENCE: 13
ccgggatcat caatgagcaa tccagacgtt ctcaactcga tcacttccaa tcgcgtaaag     60
caagtggtca atgctggtgc gtcagtggcg cgttgcatca aaatgtgttt catcgagaaa   120
gaataaagac gggttttgct tcgacaagaa aggttgtgaa ccgaacattg cggaccgaaa   180
cgcaaagctt gcgatcaaac agtgtccacg tttgattaat tggaagaagg agatcagcga   240
cttgtgcatg tgttccagtc aagcaggtgt tcatggaatt tcggactact gcggaatgct   300
gagcataatg ggatagaagg aacatcttgg tgatcatttc gcgattgttg catgatttgt   360
acatttattg tatttatacg acagcgtaat catcaagaaa ctaacttcac tcgattttcc   420
tgataaaatt taacgac                                                   437

<210> SEQ ID NO 14
<211> LENGTH: 322
<212> TYPE: DNA
<213> ORGANISM: Ostertagia ostertagi

<400> SEQUENCE: 14
ttcagcgtcg tgctttcgtt cgcgtcattg gtggcagcca cttgggtact cttcagcgac     60
tatgtccttc tcaccggtga tcatccagtg tggcctggag tagcactttt ccttaccaat   120
ttcataattt ttgcctcatc ttgtgtttac aaatttggcc gtaccgaaga atgtgggga    180
taaatgtaat ataatttcag ttggtcccct atttattcca ggatttcgct ttttctttcc   240
atcggaggca gacacaggcc ataatttcta cttactttg  tgaggacatg ttcatacttg   300
tattggacta agtatatta  cg                                             322

<210> SEQ ID NO 15
<211> LENGTH: 116
<212> TYPE: DNA
<213> ORGANISM: Ostertagia ostertagi

<400> SEQUENCE: 15
gatcgattcg attccgattc cgattccgat tccgattccg attccgattc cgattccgat     60
tccgattcga ttcgattcga tcgatcgatc gatcgatcga tcgatcgatc atcatc       116

<210> SEQ ID NO 16
```

```
<211> LENGTH: 85
<212> TYPE: DNA
<213> ORGANISM: Ostertagia ostertagi

<400> SEQUENCE: 16
catcgatccg atccgatccg atccgatccg atccgatccg atccgatccg atcgatcgat    60
cgatcgatcg tcgtcgtctc tcccc                                          85

<210> SEQ ID NO 17
<211> LENGTH: 74
<212> TYPE: DNA
<213> ORGANISM: Ostertagia ostertagi

<400> SEQUENCE: 17
gatcggatcg atcggatcgg atcgatcgat cgatcgatcg atcgatcgac gtcgcgacgc    60
gcgcgcgcgg ggcg                                                      74

<210> SEQ ID NO 18
<211> LENGTH: 142
<212> TYPE: DNA
<213> ORGANISM: Ostertagia ostertagi

<400> SEQUENCE: 18
atcagcgact ggggcgaaga cggttacttc cgtatcgtac gaggagtgga caactgcggt    60
ttccagtcgg acgtcatcgc tggggacttc ctttgacggt gtgatcgatc accataaatc   120
tcatatgcat gaaataaatt gt                                            142

<210> SEQ ID NO 19
<211> LENGTH: 145
<212> TYPE: DNA
<213> ORGANISM: Ostertagia ostertagi

<400> SEQUENCE: 19
gatcgattcc gattcgattc ggatttcgga ttcgattcgg attcggattc ggattgattg    60
gattgaattg aattcgaatt gaatttgaat ttgaatttga atttgaattt cgaatttgaa   120
atttgaaaat tgaaaaattg aaaaa                                         145

<210> SEQ ID NO 20
<211> LENGTH: 50
<212> TYPE: DNA
<213> ORGANISM: Ostertagia ostertagi

<400> SEQUENCE: 20
tcgatccgat ccgatccgat ccgatccgat cgatcgtctc tctctccccc              50

<210> SEQ ID NO 21
<211> LENGTH: 160
<212> TYPE: DNA
<213> ORGANISM: Ostertagia ostertagi

<400> SEQUENCE: 21
gatccgatcc gatccgatcc gatccgatcc gatccgattc cgatccgatt ccgaattccc    60
gattcccgat tccgaattc ccgaattccg attccggatt ccggattccg aattccgaat   120
tccgaattcc gaattcccga attcccgaat ttccccgaaa                         160

<210> SEQ ID NO 22
<211> LENGTH: 102
<212> TYPE: DNA
<213> ORGANISM: Ostertagia ostertagi
```

<400> SEQUENCE: 22

```
ctcacggacg ggaagccgca gcacatttca cttcacctca tcgatcagcg ttgtacagaa      60
tactctcatc accactcaga gtctttaata aaacaatatt tc                         102
```

<210> SEQ ID NO 23
<211> LENGTH: 102
<212> TYPE: DNA
<213> ORGANISM: Ostertagia ostertagi

<400> SEQUENCE: 23

```
catcgatccg atccgatccg atccgatccg atccgatccg atccgatccg atccgatccg      60
atccgatccg atcgatcgat cgatcgatcg tcgtcgtcgt cg                         102
```

<210> SEQ ID NO 24
<211> LENGTH: 343
<212> TYPE: DNA
<213> ORGANISM: Ostertagia ostertagi

<400> SEQUENCE: 24

```
aaatcatgtt atacttcagc agagccgcaa acgatgaacg aggatcacgc cggcagtatg      60
gctcggatag gattggagcg ttataggaaa gatggatggt gtaataaata ctattactca     120
tgtcgtgcga tacttggctt accgccaaag gaacgagctc ctatcggacc taatggcaaa     180
cgtctgtgcc gcaaaaaacc gctgtgattc gtccctatt tgcgtatttg tagtgaaata      240
cgagctgatt ttcgctccat aatgactagt tcgttgaata tttgtcatcg ctttgcagaa     300
tttcacagaa tttttgcttg cgcagaaata aatattccgc tcc                       343
```

<210> SEQ ID NO 25
<211> LENGTH: 102
<212> TYPE: DNA
<213> ORGANISM: Ostertagia ostertagi

<400> SEQUENCE: 25

```
atccgatccg attccgatcc gatccgatcc gatccgatcc gatccgatcc gatccgatcc      60
gtcgtcgatc gtcgtcgtcg tcgtcgtcga tcgatcgatc ga                         102
```

<210> SEQ ID NO 26
<211> LENGTH: 558
<212> TYPE: DNA
<213> ORGANISM: Ostertagia ostertagi

<400> SEQUENCE: 26

```
aaccagggcg ctcttggcct acggactgtt tgcaaggcgt tccgacagtt caaaggatgc      60
atgggaaagg gatactcggc ttgcataaac gctggtcact tgttaccgc ttcagttccg      120 attttcgagt cctatcagtt tgtcagcatc ttcaatcaaa tgcattatgt ttgtagagga     180
ggatttcaga tttatatgag taatgatgac tgcatgtcaa aagcttggag tgggagcact     240
ggagatcagc tgaacgcctg tcggtacaag tttgaaaaga gtagcgatgt cagcgcagaa     300
gacgctcagt ccgtgaagta cttggccaac acttacctga cgtgtttcga agaccaattc     360
aaggaggctt gtggtctaaa ctcccgcgac acgcaattct ggggttgtga atacgcgcgc     420
gtcaatgttt tcactcgctt tcctcagact gacgtggact gtgtcttacc ctacgcaggc     480
ggcatgattg gatgagagcg aagccaatac tattgtaaat gttactgtgt caagatattg     540
tgataagatt tgaaatat                                                   558
```

<210> SEQ ID NO 27
<211> LENGTH: 96
<212> TYPE: DNA
<213> ORGANISM: Ostertagia ostertagi

<400> SEQUENCE: 27
cgatcgatcc gatccgattc cgatccgatc cgatccgatc cgatccgatc cgatccgatc    60
cgatccgatc gatcgatcga tcgtcgtcgt cgcgcc                              96

<210> SEQ ID NO 28
<211> LENGTH: 88
<212> TYPE: DNA
<213> ORGANISM: Ostertagia ostertagi

<400> SEQUENCE: 28
catcgatcga tccgatccga tccgatccga tccgatccga tccgatccga tccgatcgat    60
cgatcgatcg atcgtcgtcg tcgtcccc                                       88

<210> SEQ ID NO 29
<211> LENGTH: 141
<212> TYPE: DNA
<213> ORGANISM: Ostertagia ostertagi

<400> SEQUENCE: 29
gatccgattc cgattccgat tccgattccg attccgatcc gattccgatt ccgattcgat    60
tccgattcga ttcgattcga ttccgattcg gattccgatc cgatccgatc cgatccggaa   120
tccggaatcc ggaatccgga a                                             141

<210> SEQ ID NO 30
<211> LENGTH: 148
<212> TYPE: DNA
<213> ORGANISM: Ostertagia ostertagi

<400> SEQUENCE: 30
gatccgattc cggattccgg attccggatt ccggattccg gattccgatc cggatccgga    60
tccggatccg atccgatccg atccgatccg atcgatccg atcccgatcc gatcccgga    120 tcccggatcc cggatcccgg atcccgga                                      148

<210> SEQ ID NO 31
<211> LENGTH: 109
<212> TYPE: DNA
<213> ORGANISM: Ostertagia ostertagi

<400> SEQUENCE: 31
gatcgatccg atccgatccg atccgatccg atcgatccga tccgatccat ccgatcgatc    60
cgtccgatcg atcgatcgat cgaatcgatc gatcgaatcg atcgatcga                109

<210> SEQ ID NO 32
<211> LENGTH: 107
<212> TYPE: DNA
<213> ORGANISM: Ostertagia ostertagi

<400> SEQUENCE: 32
cgatcgatcc gatccgatcc gattccgatc cgatccgatc cgatccgatc cgatccgatc    60
cgatccgatc cgatcgatcg atcgatcgat cgatcgatcg tcgatcg                  107

<210> SEQ ID NO 33
<211> LENGTH: 360

```
<212> TYPE: DNA
<213> ORGANISM: Ostertagia ostertagi

<400> SEQUENCE: 33
gtgtaagtct ggtggtaaat catgttatac ttcagcagag ccgcaaacga tgaacgagga      60
tcacgccggc agtatggctc ggataggatt ggagcgttat aggaaagatg gatggtgtaa     120
taaatactat tactcatgtc gtgcgatact tggcttaccg ccaaaggaac gagctcctat     180
cggacctaat ggcaaacgtc tgtgccgcaa aaaaccgctg tgattcgtcc cctatttgcg     240
tatttgtagt gaaatacgag ctgattttcg ctccataatg actagttcgt tgaatatttg     300
tcatcgcttt gcagaatttc acagaatttt tgcttgcgca gaaataaata ttccgctccg     360

<210> SEQ ID NO 34
<211> LENGTH: 105
<212> TYPE: DNA
<213> ORGANISM: Ostertagia ostertagi

<400> SEQUENCE: 34
cgatcgatcc gatccgatcc gatccgatcc gattccgatc cgatcgatc cgatccgatc       60 cgatccgatc gatccgatcg atcgatcgat cgtcgatcgt cgtcg                     105

<210> SEQ ID NO 35
<211> LENGTH: 320
<212> TYPE: DNA
<213> ORGANISM: Ostertagia ostertagi

<400> SEQUENCE: 35
gccgcaaacg atgaacgagg atcacgccgg cagtatggct cggataggat tggagcgtta      60
taggaaagat ggatggtgta aaatactta ttactcatgt cgtgcgatac ttggcttacc     120
gccaaaggaa cgagctccta tcggacctaa tggcaaacgt ctgtgccgca aaaaaccgct     180
gtgattcgtc ccctatttgc gtatttgtag tgaaatacga gctgattttc gctccataat     240
gactagttcg ttgaatattt gtcatcgctt tgcagaattt cacagaattt ttgcttgcgc     300
agaaataaat attccgctcc                                                 320

<210> SEQ ID NO 36
<211> LENGTH: 110
<212> TYPE: DNA
<213> ORGANISM: Ostertagia ostertagi

<400> SEQUENCE: 36
gatcgattcc gattccgatt ccgattccga ttcgattcga ttcgattcga ttcgttcgtt      60
cgattcgatt cgatgattga ttgattgatg atgattgatt gattgattga                110

<210> SEQ ID NO 37
<211> LENGTH: 259
<212> TYPE: DNA
<213> ORGANISM: Ostertagia ostertagi

<400> SEQUENCE: 37
tttgtgtaaa gatgttattt aatagttaga attatatagg tagcgaataa ctgtgaactg      60
tgttaaagtt aattattgat gactcggtgt tcggtggta tttatttgtt tagaagttta     120
tttatcaaaa atttgttata attagatttt gtttgttgat ttgtgggaat taaaattaat     180
aacactgtgc tgtgtgtttt ttgatatttta ttgtaaatgt tttgtaactt tgtgcaggtg     240
ggttttggtg gtaagtcag                                                  259
```

<210> SEQ ID NO 38
<211> LENGTH: 95
<212> TYPE: DNA
<213> ORGANISM: Ostertagia ostertagi

<400> SEQUENCE: 38
cgatcgatcg atccgatccg atccgatccg atccgatccg atccgatccg atccgatccg        60
atccgatcga tcgatcgatc gatcgtctcg cctcg                                    95

<210> SEQ ID NO 39
<211> LENGTH: 368
<212> TYPE: DNA
<213> ORGANISM: Ostertagia ostertagi

<400> SEQUENCE: 39
gatgttgagt gtaagtctgg tggtaaatca tgttatactt cagcagagcc gcaaacgatg         60
aacgaggatc acgccggcag tatggctcgg ataggattgg agcgttatag gaaagatgga        120
tggtgtaata aatactatta ctcatgtcgt gcgatacttg gcttaccgcc aaaggaacga        180
gctcctatcg gacctaatgg caaacgtctg tgccgcaaaa aaccgctgtg attcgtcccc        240
tatttgcgta tttgtagtga aatacgagct gattttcgct ccataatgac tagttcgttg        300
aatatttgtc atcgctttgc agaatttcac agaattttttg cttgcgcaga aataaatatt       360
ccgctccg                                                                 368

<210> SEQ ID NO 40
<211> LENGTH: 100
<212> TYPE: DNA
<213> ORGANISM: Ostertagia ostertagi

<400> SEQUENCE: 40
gatcgatccg atccgatccg atccgatccg atccgatccg atccgatcga tcgatccgat         60
cgatcgatcg atcgtcgtcg tcgtcgtcgt cgtcgatcga                              100

<210> SEQ ID NO 41
<211> LENGTH: 75
<212> TYPE: DNA
<213> ORGANISM: Ostertagia ostertagi

<400> SEQUENCE: 41
ggcgatcgat cgatcgatcg atcgatcgat cgatcgatcg atcgtcgtcg acgcgtcgcg         60
acgacgacga cgcgc                                                          75

<210> SEQ ID NO 42
<211> LENGTH: 67
<212> TYPE: DNA
<213> ORGANISM: Ostertagia ostertagi

<400> SEQUENCE: 42
gatcgattcc ggatccggat ccggatccga tcgatcgatc gtcgtcgcgc gacgacgcgc         60
ccccccc                                                                   67

<210> SEQ ID NO 43
<211> LENGTH: 180
<212> TYPE: DNA
<213> ORGANISM: Ostertagia ostertagi

<400> SEQUENCE: 43 acctccccctt ctgctcaaaa gcgaagccgt caacattcag agctgctgat tgaactctcg        60

```
ttctcttctg caaagcatct tacagtgtat tttcatacgc acctactgcg taattcttcc    120
ttcttcttat gtaaacttgg tacctatata atccattctc tttccccgaa taaatattac    180
```

<210> SEQ ID NO 44
<211> LENGTH: 60
<212> TYPE: DNA
<213> ORGANISM: Ostertagia ostertagi

<400> SEQUENCE: 44

```
gtcgatcgat cgatcgatcg tcgtcgtcgt cgtcgtcgtc gtcgtctctc tctctctctc    60
```

<210> SEQ ID NO 45
<211> LENGTH: 129
<212> TYPE: DNA
<213> ORGANISM: Ostertagia ostertagi

<400> SEQUENCE: 45

```
ttatatccat aatctgttta ttcgtgtctg tgccctgtg agttctttt ttgaggtgaa     60 acatctggat ttgatctgtc gtgttccttc tattgatgcg ttaacgcgac acagaaatga    120
aatgtcacg                                                             129
```

<210> SEQ ID NO 46
<211> LENGTH: 50
<212> TYPE: DNA
<213> ORGANISM: Ostertagia ostertagi

<400> SEQUENCE: 46

```
ggcgtcgtcg tcgtcgtcgt cgtcgtcgtc tctctctctc tctctccccc              50
```

<210> SEQ ID NO 47
<211> LENGTH: 225
<212> TYPE: DNA
<213> ORGANISM: Ostertagia ostertagi

<400> SEQUENCE: 47

```
cattacggcc gggggagctg tgggcgcttt tttggacact cattcttgag tgccatatcc    60
atcgaaattc actatgccca gaccaattgt agccacccat cgtttgttag tcggtgcgac   120
ggtggctctt gaaaccaaac gttgtttctg agctagatgc ctgcatgcga tgtacgttcg   180
tcttacggat gcccatcatc tctctgtata aaattccatg atgct                    225
```

<210> SEQ ID NO 48
<211> LENGTH: 91
<212> TYPE: DNA
<213> ORGANISM: Ostertagia ostertagi

<400> SEQUENCE: 48

```
gtcgatcgat cgatcgatcg atcgatcgat cgtcgatcga tcgatcgatc gatcgatcga    60
tcgatcgatc gtcgtcgtcg atcgatcgtc g                                    91
```

<210> SEQ ID NO 49
<211> LENGTH: 265
<212> TYPE: DNA
<213> ORGANISM: Ostertagia ostertagi

<400> SEQUENCE: 49

```
cggcattacg gccggggtgg aagaagggcg tggttctcga cctaaccatt tcaagaaagg    60
gtccggctcc gtagtgcgca aggccttgca gaccctcgaa gctatcaaat gggttgagaa   120
```

```
acatgcagat ggcaagggtc gagtcttgtc aaagcaggga agaaaggatt tggatcgaat    180
tgcaaccgaa cttcgtcagc acgttaaacc gattgagctc taagttgttt tcagtgcatg    240
ttgttttgtt ataaatgttg caatg                                          265

<210> SEQ ID NO 50
<211> LENGTH: 131
<212> TYPE: DNA
<213> ORGANISM: Ostertagia ostertagi

<400> SEQUENCE: 50
ggatccggga ttcccgggat tccggattcc ggattccgga ttccggattc cggattcgga    60
ttcgattcga tttcgattcg attcgattcg attcgattca ttcattcgtt cttcattcat   120
tcgattcgtt g                                                         131

<210> SEQ ID NO 51
<211> LENGTH: 102
<212> TYPE: DNA
<213> ORGANISM: Ostertagia ostertagi

<400> SEQUENCE: 51
attacggccg gggcgtgtag tcattgacgt gtatcttttg aaacttaact tgttatcttt    60
tgctacattg ttgtgctgaa aataaagta gtttgaattt tg                       102

<210> SEQ ID NO 52
<211> LENGTH: 489
<212> TYPE: DNA
<213> ORGANISM: Ostertagia ostertagi

<400> SEQUENCE: 52
tcggcattac ggccggggtc cgtcgtcgac tccaaagcta ctaagactgg tccaacccctt    60 catggaatta ttggtcgcaa atccggaacc gttgatggtt ttgattactc tgctgccaat   120
aaaaacaagg gagtggtatg gacgcgagag acattgtttg aataccttct gaaccctaag   180
aagtacatcc ctggaacaaa gatggtcttc gctggattga agaaagtcga tgaacgagct   240
gatctcataa aatacattga agttgaatcg gcgaaacctg tcagttaacc ataatgatta   300
tttaatttga gatatgttcg tataggtttt agtgaaagtt ttataaagat cttgatattt   360
gcgctgttgc agaaacgtta gcgctcgact taaccattcg ttcattatct catctcagct   420 gcccttacc cgtattgtaa taccaatttt atagtagcaa tgtctcattg aagtgaatct   480
tccaccgcg                                                            489

<210> SEQ ID NO 53
<211> LENGTH: 256
<212> TYPE: DNA
<213> ORGANISM: Ostertagia ostertagi

<400> SEQUENCE: 53
gtgctcggga gcgcgccatt gtgctcggga agcagcgcca ttgtgctcgc gcaaatgcat    60
cgtcatgtgg gcccgaaaaa ggacgattgt ggggtgcgaa tacaagccaa ccgggaacta   120
ctttggagct ccgatctacg aagtaggaga accgtgctcg aagtgcgact gtgagggctg   180
caaatgtaac aaggacgatg gtctttgcgt tacaccgtaa atccagctgg aaagtcttcc   240
aaataaactt gaaaag                                                    256

<210> SEQ ID NO 54
<211> LENGTH: 95
```

```
<212> TYPE: DNA
<213> ORGANISM: Ostertagia ostertagi

<400> SEQUENCE: 54
catcgatccg atccgatccg atccgatccg atccgatccg atccgatcga      60
tcgatcgatc gtcgtcgtcg tcgtcgtcgt cgtcg                      95

<210> SEQ ID NO 55
<211> LENGTH: 153
<212> TYPE: DNA
<213> ORGANISM: Ostertagia ostertagi

<400> SEQUENCE: 55
gatccgatcc gatccgatcc gattccgatt ccgatccgat ccgatccgat cccgatcccg     60
atccgatccg atcccgatcc cgatcccga ttcccgattc ccgattcccg attccggatt    120
cccggatttc ccggatttcc cggatttccc gga                                153

<210> SEQ ID NO 56
<211> LENGTH: 114
<212> TYPE: DNA
<213> ORGANISM: Ostertagia ostertagi

<400> SEQUENCE: 56
gatcgatccg atccgatccg atccgatccg atccgatccg atccgatccg atccgatccg     60
atccgatccg atcgatcgat cgatcgatcc gatccgatcc gatcgatcga tcga          114

<210> SEQ ID NO 57
<211> LENGTH: 93
<212> TYPE: DNA
<213> ORGANISM: Ostertagia ostertagi

<400> SEQUENCE: 57
gatcgatccg attccgatcc gatccgatcc gatccgatcc gatccgatcg atcgatcgat     60
cgatcgatcg tcgtcgtcgt cgtcgtccgc gcg                                  93

<210> SEQ ID NO 58
<211> LENGTH: 711
<212> TYPE: DNA
<213> ORGANISM: Ostertagia ostertagi

<400> SEQUENCE: 58
gttacaaagg gagtacaata tttgaatgaa atcaaggatt cggtcgttgc tggattccaa     60
tgggcaacaa gagaaggagt tctggctgac gaacacatgc gcggaattcg ttttgacatc    120
caagatgtaa cacttcacgc tgacgctatc cacagaggtg gtggccaaat catcccaact    180
gctcgtcgtg taatttatgc atctgtactc actgctgcac cacgacttct ggaacccgtt    240
tacctcgttg aaattcaatg tcctgaggtt gccgttggtg gtatctatgg tgtgctcaat    300
cgtcgaagag gacacgtgtt cgaagagtca caggtcaccg gaactcctat gtttgttgtc    360
aaagcctacc ttcccgtcaa cgaatcattt ggtttcactg ccgatcttcg ttcgaatacc    420
ggtggtcaag cttttccctca atgtgtgttt gatcactggc aagttctacc aggagaccca    480
ctggagcccg gtactaagcc taaccaagtt gttctggaga caaggaagcg taaaggactc    540
aaggagggcg tgcccgctct tgacaactac cttgacaaaa tgtaaatcta ttgttccggc    600
ttgttgttac cgaagttatc taataaaaaa ggttgttgat ggagctgttt cgcagttatt    660
cgaaattccc gttgttttat ttatgcaaga gctaaataaa gttgtatagc t             711
```

<210> SEQ ID NO 59
<211> LENGTH: 161
<212> TYPE: DNA
<213> ORGANISM: Ostertagia ostertagi

<400> SEQUENCE: 59
gatccgatcc cgattcccgg attccggatt ccggattccg gatccggatt ccggattccg    60
gatccggatt ccgattccga tccggaatcc ggatccggat ccggaatcgg aatcggaaat   120
cggaattcgg aattcggaat tcggaattcg gaatttcgga a                       161

<210> SEQ ID NO 60
<211> LENGTH: 100
<212> TYPE: DNA
<213> ORGANISM: Ostertagia ostertagi

<400> SEQUENCE: 60
atcgatccga tccgatccga tccgatccga tccgatccga tccgatcgat cgatcgatc     60 gatcgatcga tcgatcgatc gtcgtcgtcg atcgtcgtcg                         100

<210> SEQ ID NO 61
<211> LENGTH: 498
<212> TYPE: DNA
<213> ORGANISM: Ostertagia ostertagi

<400> SEQUENCE: 61
tattccttaa ttctggaccc ggaaacacta ccagccccctt caaatgcgag tggatgacca    60
ttaaggatga cgtgctctat gttggcggtc acggcaatgt gttcagaaat agagcaggag   120
aaattgtgca cagcaacaac atgtggatca aaaccgtcac cccggaagga gaggttacca   180
atgtagactg gacagatgtt tacaacaacg cccgaaatgc tgtcggtatt tctgaaccag   240
gataccttac acatgaagcg gttcagtggt cagaaacaca gggacattgg tacttccttc   300
ctagaaagga gtcaaagact gtctacgtag aagaagagga tgagcaaaaa ggcacggatc   360
tcctgattac tggaaatccg gaccttgatc aattcgaagt caagaggata ggaatactgc   420
gacccgaacg cggatattcg gcattcgatt ttattcctgg taccgacgac aagatcatcg   480
ttgccttgaa gtccaaag                                                 498

<210> SEQ ID NO 62
<211> LENGTH: 48
<212> TYPE: DNA
<213> ORGANISM: Ostertagia ostertagi

<400> SEQUENCE: 62
gcgtcgatca tcatcgatca catcatcaca cacaaaaaaa aaacccccc                48

<210> SEQ ID NO 63
<211> LENGTH: 113
<212> TYPE: DNA
<213> ORGANISM: Ostertagia ostertagi

<400> SEQUENCE: 63
atcgatcgat ccgatccgat ccgatccgat ccgatccgat ccgatccgat ccgatccgat    60
ccgatccgat ccgatccgat ccgatccgat ccgatccgat ccgatccgat cga          113

<210> SEQ ID NO 64
<211> LENGTH: 59
<212> TYPE: DNA
<213> ORGANISM: Ostertagia ostertagi

<400> SEQUENCE: 64
gatcggatcg gatcgatcga tcgacgaacg acgacgacac gagatgtcgt cgcgccgga    59

<210> SEQ ID NO 65
<211> LENGTH: 50
<212> TYPE: DNA
<213> ORGANISM: Ostertagia ostertagi

<400> SEQUENCE: 65
gatccgattc cgatccgatc cgatccgatc gatcgtcgtc gtcgtcgtcc    50

<210> SEQ ID NO 66
<211> LENGTH: 405
<212> TYPE: DNA
<213> ORGANISM: Ostertagia ostertagi

<400> SEQUENCE: 66
ttacggccgg gcttcggagg tgcgatgaag ggcatcttgg gttatactga agaccaagtt    60
gtgtcgactg acttcttgtc tgacacacgc tcatccattt tcgacgcggg agcgtgcatc    120
tctcttaacc cgaactttgt caagctcatt tcatggtatg acaacgagta cggatactcg    180
caccgtgtcg tcgatctgct tacctacatt gccagcaagg cctaaaatgt tgccgtgtt    240 tgctggtttg cgctctcaat caaagttgtg gttccctaat gtttcataga gttagtcacc    300
actatgagcg tacattttt ctgtagtctt gtaggtttcc ttttttcttt ggtagcatgt    360
aatttatgta gagcttttat gtaataaaat tttgtgatgt aaaac    405

<210> SEQ ID NO 67
<211> LENGTH: 97
<212> TYPE: DNA
<213> ORGANISM: Ostertagia ostertagi

<400> SEQUENCE: 67
gatccgatcc gattccgatt ccgatccgat ccgatccgat ccgatccgat cgatcgatcg    60
atcgtcgatc gtctctcgtc gatcgatcga cgacaca    97

<210> SEQ ID NO 68
<211> LENGTH: 596
<212> TYPE: DNA
<213> ORGANISM: Ostertagia ostertagi

<400> SEQUENCE: 68
ggcattacgg ccggggatct gattcggagg accacaatgc cgagacactg gatcatcaat    60
tcactttggt gaagaaaaga acgaaacaat cccacgtgat gcgttacggt agtctggata    120
tagccaaaga gccaccccaa gaagagaagg tgtcatggcc atcaagagac gtccaactca    180
tgcatctgca gatgcagaaa ctgttcaatc ctcaagcagc cgctgtcgac atcgaaatca    240
acagaatcca gacggatcga caaaacattg aggcagtttt cacaagtctg atcaaccacc    300
tcgtcgaaga tggtagcgaa aggcgtcgtt tatttgagca aaggagcgat attgaaaatc    360
tcgactgcca tgacgatgtc gtgagggtat tcgatatgat ttgcattgac gtaaataagt    420
atgactatgc cctgaagtat gtgtatgttc tgaacaacct atgcacaaag ttcaacgatt    480
cggcgaagat catcaaggca atgtggacta tctgctcaaa gacgcgctca agttcctct    540 gaagcatctt cttaatgagc tctgtcgata ttatttcaga ataaatattc atgaag    596

<210> SEQ ID NO 69

-continued

```
<211> LENGTH: 116
<212> TYPE: DNA
<213> ORGANISM: Ostertagia ostertagi

<400> SEQUENCE: 69
gatccgattc cgattccgat ccgatccgat ccgatccgat ccgatcgatc gatcgaatcc    60
gatcgaatcg aatcgatcga tcgatcgatc ggatcggatc ggatcggatc gatcga       116

<210> SEQ ID NO 70
<211> LENGTH: 110
<212> TYPE: DNA
<213> ORGANISM: Ostertagia ostertagi

<400> SEQUENCE: 70
gtcgtccgat ccgatccgat ccgatccgat ccgatccgat ccgatcgatc gatcgatcga    60
atcgatcgat cgaatcgaac ggaacgaacg acggacggat ccggatcgga              110

<210> SEQ ID NO 71
<211> LENGTH: 136
<212> TYPE: DNA
<213> ORGANISM: Ostertagia ostertagi

<400> SEQUENCE: 71
ctcacggccg ggggttgcca gccaaccgat gatatcccta gagcgaagaa agagtcgaag    60
agaaagcaga ggcgccaatt ggctcgtgga gagtattgaa catgattgtt gttgttgttc   120
agtaaatatt ttgttg                                                    136

<210> SEQ ID NO 72
<211> LENGTH: 88
<212> TYPE: DNA
<213> ORGANISM: Ostertagia ostertagi

<400> SEQUENCE: 72
gtcgatccga tccgattcga tcgtcgtcgt cgtcgtcgat cgacgatcga tcgatcgtcg    60
atcgatcgtc gtcgtcgtcg tcgatcga                                       88

<210> SEQ ID NO 73
<211> LENGTH: 331
<212> TYPE: DNA
<213> ORGANISM: Ostertagia ostertagi

<400> SEQUENCE: 73
tcggcattac ggccgggggg agtacagttc ggagcagtag cagtacaata tgctgttctg    60
cttcgtatgc ctttctctca tccttagctc cgctatccag agtggagtca attctatgtt   120
tgcatcagtg ccgcctggag cttcggtaat gcaagaatgc cgagatcggc ttctcacatg   180
cgaacacgat gctaaaaatg gtttctgtga agacctgagc gactactaca tatattattg   240
ctgtaaaagt tgtagccaac ttgagtcagt tgaaaaaaaa atgaaacaag tttcaattct   300
attcatcgat ttcaataaac atttcgctta c                                  331

<210> SEQ ID NO 74
<211> LENGTH: 117
<212> TYPE: DNA
<213> ORGANISM: Ostertagia ostertagi

<400> SEQUENCE: 74
ggatccgatc cgattccgat tccgattccg atccgatccg atccgattcc gatccgatcc    60
gatccgattc cgatcgatcg ttcgttcgtt cgtcgtcgtc gttccgttcc attccga      117
```

<210> SEQ ID NO 75
<211> LENGTH: 275
<212> TYPE: DNA
<213> ORGANISM: Ostertagia ostertagi

<400> SEQUENCE: 75

| | | |
|---|---|---|
| gcttacggcc gggggctca tcattaatcc agcacatttc gccatgatct tctactttgt | 60 |
| ctgtgcactt ttccttctca acgcattcac agctgagggt gctgccaccg cgccatgtga | 120 |
| ggatcaagga ggcgagtcgt tctgccttgg cccaaagcac gccggccagt gcagcagtcc | 180 |
| ggacttccag cccattgcac agcagttctg tgctaaaact tgtggtattt gtcactgaat | 240 |
| aatctggagg atattcacta ataaagtttc tcggg | 275 |

<210> SEQ ID NO 76
<211> LENGTH: 131
<212> TYPE: DNA
<213> ORGANISM: Ostertagia ostertagi

<400> SEQUENCE: 76

| | | |
|---|---|---|
| ggatcggatc ggatcggatc ggatcgatcg atcgatcgat cgatcgaatc gatccgatcg | 60 |
| atcggattcg gattcgattc gattcgatcg attcgaattc gaaaattcga aaatcgaaa | 120 |
| aaatcgaaaa a | 131 |

<210> SEQ ID NO 77
<211> LENGTH: 153
<212> TYPE: DNA
<213> ORGANISM: Ostertagia ostertagi

<400> SEQUENCE: 77

| | | |
|---|---|---|
| gatcgatccg attccgatcc gaatccgaat ccgaatccga tccgaatccg aatccgaatc | 60 |
| cgaatccgaa tccgaatccg gaatccggaa tccgaatccg aatccgaatc cggaatccgg | 120 |
| aatccggaat ccggaaatcc ggaaatccgg aaa | 153 |

<210> SEQ ID NO 78
<211> LENGTH: 190
<212> TYPE: DNA
<213> ORGANISM: Ostertagia ostertagi

<400> SEQUENCE: 78

| | | |
|---|---|---|
| gtcgatccga tccgatccga tccgatccga tccgatccga ttccgattcc gattccggat | 60 |
| tccggattcc gattccgatt ccgatttccc gatttcccga atttcccga atttccccgg | 120 |
| aatttccccc ggaatttccc ccggaatttc ccccgggaaa tttccccccg ggaaatttcc | 180 |
| cccgggaaaa | 190 |

<210> SEQ ID NO 79
<211> LENGTH: 285
<212> TYPE: DNA
<213> ORGANISM: Ostertagia ostertagi

<400> SEQUENCE: 79

| | | |
|---|---|---|
| gggacaacaa tgctcgtcta tctgttggtc gctctaatat tcctcaacac cgtcactgca | 60 |
| caagctgatg caaccgcgtg caaagacgcc gacccagggg atctcgccac gccctgtgaa | 120 |
| aacctcaagg accaaggttt ttgcgacgat ctcgacatgc gcgactacat gaacgactac | 180 |
| tgcaaaaaga cgtgcaagtt ttgtatgcct taatgtgact ctatcaagta aatttcggag | 240 |

```
ggctcatatc actatgtctt aagtatcgga taaatgtcta gcaat                    285
```

<210> SEQ ID NO 80
<211> LENGTH: 105
<212> TYPE: DNA
<213> ORGANISM: Ostertagia ostertagi

<400> SEQUENCE: 80

```
gcgatcgatc gatcgatccg atccgatccg atccgatccg atccgatccg atccgatccg    60
atccgatcga tcgatcgatc gatcgatcga tcgatcgatc gatcg                    105
```

<210> SEQ ID NO 81
<211> LENGTH: 303
<212> TYPE: DNA
<213> ORGANISM: Ostertagia ostertagi

<400> SEQUENCE: 81

```
cggggaccaa acgatccatt cggcaattat aaggttctct catacaagga aggacgccga    60
ttcgaatacg tccattaccc tttcttcgtt ctgcaatacg atgagaggag gcaaacttac    120
aaagcacact actttggata catagaggag gaggacaagc aaacaaagaa gttcactcgc    180
aaaataggtc cgttgaccgc tgaggaattc acaactaaat ataatcattg caacaagtgg    240
tgataatggt cgtctacaac aaaactttgt ccacttcgat gaaataaaat ttcgcagttg    300
aat                                                                  303
```

<210> SEQ ID NO 82
<211> LENGTH: 66
<212> TYPE: DNA
<213> ORGANISM: Ostertagia ostertagi

<400> SEQUENCE: 82

```
gtcgatcgat ccgaatcgaa tcgatcgatc gatcgtcgtc tctcatctcc cacctccatc    60
atatat                                                               66
```

<210> SEQ ID NO 83
<211> LENGTH: 110
<212> TYPE: DNA
<213> ORGANISM: Ostertagia ostertagi

<400> SEQUENCE: 83

```
gtcgtccgat ccgatccgat ccgatccgat ccgatccgat ccgatcgatc gatcgatcga    60
atcgatcgat cgaatcgaac ggaacgaacg acggacggat ccggatcgga              110
```

<210> SEQ ID NO 84
<211> LENGTH: 275
<212> TYPE: DNA
<213> ORGANISM: Ostertagia ostertagi

<400> SEQUENCE: 84

```
gcattacggc cggggtgtat ttaatagtta gaattataaa ggtagagtaa ataactgtga    60
actgtgttaa agttaattat taatgactcg gtgtttcggt gatatttatt tgtttagaag    120
tttatttatt taaaaattta ttataattag attttgtttg ttgatttgtc ggaattaaaa    180
ttaacaatac tgtgctgtgt gcttttttgat atttattgta aatgttttgt aaacgttttg    240
taattttgtg taggtgggtt ttggtggtaa gttac                               275
```

<210> SEQ ID NO 85
<211> LENGTH: 98

```
<212> TYPE: DNA
<213> ORGANISM: Ostertagia ostertagi

<400> SEQUENCE: 85
tcgatccgat ccgatccgat ccgatccgat cgatcgatcg atcgatcgat cgatcgatcg        60
atcgatcgat cgatcgatcg atcgtcgtcg atcgtcga                                98

<210> SEQ ID NO 86
<211> LENGTH: 384
<212> TYPE: DNA
<213> ORGANISM: Ostertagia ostertagi

<400> SEQUENCE: 86
tcggcttacg gccggggtcc gggtcgcagt cgaaggtgtc agatgaggac ctgggaagag        60
tgatgggaat tgccgatgt cttaaccttt ccttcactga agaacaagtg ttggcgataa        120
tcgcggtaat cgaagcagga gcgaatccat ctacgctggt ggattggttg ccgatatgg        180 aagaagcaaa agcgggagag acaactagct tgaattttg aaaaacgatt gatcgtagaa        240
ggatattatt tgttttattt atgttcacga ttatttaaga gaatatgttg tggcagacgg        300
gatgatcctc tttgatattt attgagggtc aattatgtga agcatattgt tgtttgcgga        360
tttttcgcaa ataaatgtca tttc                                              384

<210> SEQ ID NO 87
<211> LENGTH: 138
<212> TYPE: DNA
<213> ORGANISM: Ostertagia ostertagi

<400> SEQUENCE: 87
gatcgatccg atccgatccg atccgatccg atcgatccg atcgatcga tcgatcgatc         60 cgatccgatc cgattccgat tccgattccg gattccggat tccggattcc ggatttccgg       120
atttccggat ttcccgga                                                     138

<210> SEQ ID NO 88
<211> LENGTH: 89
<212> TYPE: DNA
<213> ORGANISM: Ostertagia ostertagi

<400> SEQUENCE: 88
gatcgatcga tcgatcgatc gatcgatcat catcatcgat cgacgacgac gacgacgacg        60
atcgatcgat cgatcgatcg atcgatcga                                         89

<210> SEQ ID NO 89
<211> LENGTH: 45
<212> TYPE: DNA
<213> ORGANISM: Ostertagia ostertagi

<400> SEQUENCE: 89
gattcgattc gatcgatcgt cgtctctctc tttttttttt ttttt                       45

<210> SEQ ID NO 90
<211> LENGTH: 96
<212> TYPE: DNA
<213> ORGANISM: Ostertagia ostertagi

<400> SEQUENCE: 90
gatcgatccg atccgatccg atcgatcgat cgatcgatcg atcgatcgat cgatcgatcg        60
atcgatcgat cgatcgatcg tcgtcgtcgt cgtcga                                 96
```

<210> SEQ ID NO 91
<211> LENGTH: 92
<212> TYPE: DNA
<213> ORGANISM: Ostertagia ostertagi

<400> SEQUENCE: 91
gatcgatccg atccgatccg atcgatcgat cgatcgatcg atcgatcgat cgatcgatcg    60
atcgatctca tctcatcgat cgatcatcat ca                                  92

<210> SEQ ID NO 92
<211> LENGTH: 120
<212> TYPE: DNA
<213> ORGANISM: Ostertagia ostertagi

<400> SEQUENCE: 92
gatcgatccg atccgatccg atccgatccg atccgatccg atccgatcga tcgatcgatc    60
gatcgatcga tcgatcgatc gatccgatcc gattccgaat tccgaattcc gaattccgaa   120

<210> SEQ ID NO 93
<211> LENGTH: 116
<212> TYPE: DNA
<213> ORGANISM: Ostertagia ostertagi

<400> SEQUENCE: 93
atcgatccga tccgatccga tccgatccga tccgatccga tccgatccga tccgatccga    60
tccgatccga tccgatccga tcgatccgat cgatccgatc cgatcgatcc gatcga       116

<210> SEQ ID NO 94
<211> LENGTH: 103
<212> TYPE: DNA
<213> ORGANISM: Ostertagia ostertagi

<400> SEQUENCE: 94
cgatcgatcc gatccgatcc gatcgatccg gatccgatcc gatccgatcc gatccgatcc    60
gatccgatcc gatcgatcga tcgatcgatc gtcgtcgtcg tcg                     103

<210> SEQ ID NO 95
<211> LENGTH: 308
<212> TYPE: DNA
<213> ORGANISM: Ostertagia ostertagi

<400> SEQUENCE: 95
ggccggggac tttacgatgt atatcgcatt gattgcgggg caaacgtgac attcaacctg    60
actatcggtg atcatgtcta cactctcgag tcggaaaatc ttattgtcaa atttgatgtt   120
gatttctgtg cattggcaat attcccgatg cgctccggcg gctatggacc ccagtggatt   180
cttggcgatc cgttcatacg ccagtactgc aacattcatg acatcggcaa acagcgaatt   240
ggctttgcaa aaccagtcaa gaaatagcga ttttgtgatg ttctgattag atggtataaa   300
tgcttcac                                                            308

<210> SEQ ID NO 96
<211> LENGTH: 114
<212> TYPE: DNA
<213> ORGANISM: Ostertagia ostertagi

<400> SEQUENCE: 96
gtcgatcgat cgatcgatcg atcgatcgat cgatcgatcg atcgatcgat cgatcgatcg    60
atcgatcgat ccgatcggat ccggattcgg attcgggatt ccgggattcc ggga         114

<210> SEQ ID NO 97
<211> LENGTH: 286
<212> TYPE: DNA
<213> ORGANISM: Ostertagia ostertagi

<400> SEQUENCE: 97

```
tcggcttacg gccggggtag aaggaagtga attagctaag gctgaagcac ttatacgagc      60
tgaggttgct gacgcgttgc tgaaggctgc cactggacaa caataaatgt aacataggcc     120
aatttaggat ggattctttg caaattcaaa aaccactctt aatggcaatt ttctaaaatt     180
taatagtgtt aacttcatac tcgcccttgg ttatcgtact atagactgat tgacgttgat     240
gtagtgagaa taaatatcct tctattatat aaagcgctaa ctttgt                    286
```

<210> SEQ ID NO 98
<211> LENGTH: 157
<212> TYPE: DNA
<213> ORGANISM: Ostertagia ostertagi

<400> SEQUENCE: 98

```
atcgatccga tccgattccg attccgattc cgattccgat tccgattccg attccgattc      60
cgattccgat tccgattccg attccgattc cgattccgat ttccgatttc cgatttccga     120
tttccggatt tccggaattt ccggaatttt cccggaa                              157
```

<210> SEQ ID NO 99
<211> LENGTH: 114
<212> TYPE: DNA
<213> ORGANISM: Ostertagia ostertagi

<400> SEQUENCE: 99

```
gtcgatcgat ccgatccgat ccgatccgat ccgatcgatc cgatccgatc gatccgatcc      60
gatccgatcg atcgatcgat ccgatccgat ccgatccgat ccgatccgat ccga           114
```

<210> SEQ ID NO 100
<211> LENGTH: 121
<212> TYPE: DNA
<213> ORGANISM: Ostertagia ostertagi

<400> SEQUENCE: 100

```
gatccgattc cgattccgat tccgattccg gattccgatc cgatccgatc cgatccgatc      60
cgtcgatcga tcgatcgatc gatcgatcga ttcgattcga ttcgattcga ttcgatttcg     120
a                                                                     121
```

<210> SEQ ID NO 101
<211> LENGTH: 111
<212> TYPE: DNA
<213> ORGANISM: Ostertagia ostertagi

<400> SEQUENCE: 101

```
gatcgatccg atccgatccg atccgatccg atccgatccg atccgatccg atccgatccg      60
atccgatcga tcgatcgatc gattcgatcg atcgatcgat cgatcgatcg a              111
```

<210> SEQ ID NO 102
<211> LENGTH: 312
<212> TYPE: DNA
<213> ORGANISM: Ostertagia ostertagi

<400> SEQUENCE: 102

```
agggcgtaaa cgacgtgtag acatgtagat tatttcgatt ccttctccac gatgacccca    60
tgtgaaataa gccoctgtgc gattccatgt gcctctagat tctcatactt gcaagcctta   120
ccaatttcgg cgacctaggc gccttctgac ggcgtccgct cttcgatgtt gcttttttccc   180 aactccgtaa aaccagcaac atcagtgaac agctcgtggg cgctctgcct agctgccacg   240
cgccgtcgat tacttgtata tgtcttgtga atattacatt atttacggat atcatgtgga   300
aataaattat tg                                                        312

<210> SEQ ID NO 103
<211> LENGTH: 110
<212> TYPE: DNA
<213> ORGANISM: Ostertagia ostertagi

<400> SEQUENCE: 103
atcgatccga tccgatccga tccgatccga tccgatccga tccgatccga tccgatccga    60
tcgatccgat cgatcgatcg atcgatcgat cgatcgatcg atccgatcga               110

<210> SEQ ID NO 104
<211> LENGTH: 182
<212> TYPE: DNA
<213> ORGANISM: Ostertagia ostertagi

<400> SEQUENCE: 104
ggtcgatcga attcgaattc gaattcgaat tcgaattccg aattcgaaaa ttcgaaaaat    60
cgaaaaatcg aaaaatcgaa aaatcgaaaa tccggaaatc cggaatcccg gaatcccgga   120
atccccggaa tccccggaat cccggaattc ccggaattcc cggaattccc ggaatcccgg   180
aa                                                                   182

<210> SEQ ID NO 105
<211> LENGTH: 93
<212> TYPE: DNA
<213> ORGANISM: Ostertagia ostertagi

<400> SEQUENCE: 105
atcgatccga tccgattccg atccgatccg atccgatccg atccgatcga tcgatcgtcg    60
atcgatcgtc gtcgtcgtcg tcgtcgtcgt ctc                                  93

<210> SEQ ID NO 106
<211> LENGTH: 135
<212> TYPE: DNA
<213> ORGANISM: Ostertagia ostertagi

<400> SEQUENCE: 106
atcgatccga tccgatccga tccgattccg attccgatcc gatccgatcc gatccgatcc    60
gatccgatcc gatccgatcc gatccgatcc gatccgattc cgattccgga attccggaat   120
tccggaattc cggaa                                                     135

<210> SEQ ID NO 107
<211> LENGTH: 72
<212> TYPE: DNA
<213> ORGANISM: Ostertagia ostertagi

<400> SEQUENCE: 107
gatcgatccg atccgatccg atccgatcga tcgatcgtcg tcgtcgtcgt cgtctcgtcg    60
acgccctccc cg                                                         72
```

<210> SEQ ID NO 108
<211> LENGTH: 107
<212> TYPE: DNA
<213> ORGANISM: Ostertagia ostertagi

<400> SEQUENCE: 108

```
gatcgattcc gatccgatcc gatcgatccg atcgatcgat cgatcgatcg atcgatcgat    60
cgatcgatcg atcgatcgat cgatcgatcc gatccgatcc gatcga                   107
```

<210> SEQ ID NO 109
<211> LENGTH: 156
<212> TYPE: DNA
<213> ORGANISM: Ostertagia ostertagi

<400> SEQUENCE: 109

```
gatcgatccg atccgatccg atccgattcc gattccgatc cgatccgatc cgatccgatc    60
cgatccgatc cgattccgat tccgattccg atttcccgaa ttcccgaatt cccgaattcc   120
ccgaattccc cggaattccc cggaattccc cggaaa                              156
```

<210> SEQ ID NO 110
<211> LENGTH: 93
<212> TYPE: DNA
<213> ORGANISM: Ostertagia ostertagi

<400> SEQUENCE: 110

```
gatcgatccg atccgatccg atccgatccg atccgatccg atccgatccg atcgatcgat    60
cgatcgatcg tcgtcgtcgt cgtcgtcgtc gcc                                 93
```

<210> SEQ ID NO 111
<211> LENGTH: 116
<212> TYPE: DNA
<213> ORGANISM: Ostertagia ostertagi

<400> SEQUENCE: 111

```
catcgatcga tccgatccga ttccgatccg atccgatccg atccgatccg atccgatccg    60
atccgatccg atccgatccg atccgatccg atccgatccg atccgatccg atccga       116
```

<210> SEQ ID NO 112
<211> LENGTH: 126
<212> TYPE: DNA
<213> ORGANISM: Ostertagia ostertagi

<400> SEQUENCE: 112

```
ggatcggatc cggatccgat ccgatccggg aatccggaat ccgaaatccg aaatccgaaa    60
tccgaaaatc gaaaacaaaa caaaacgaaa tcgaatcgaa tccgaaccga ccgaccgacc   120
gacgac                                                               126
```

<210> SEQ ID NO 113
<211> LENGTH: 86
<212> TYPE: DNA
<213> ORGANISM: Ostertagia ostertagi

<400> SEQUENCE: 113

```
gatcgatcga tcgatcgatc gatcgatcga tcgatcgtcg atcgatcgtc cgtcctctcg    60
atcgtcgcgt cgtcgtcgtc gatcga                                         86
```

<210> SEQ ID NO 114
<211> LENGTH: 250
<212> TYPE: DNA

<213> ORGANISM: Ostertagia ostertagi

<400> SEQUENCE: 114

| | |
|---|---|
| cggcattacg gccggggaga gagggtgatt caacagctgt cagagtcccc tcctatacgc | 60 |
| gcactcgctc gagcaatggt acgtggagga aaaacagtcc aggacaagct cggtaacacg | 120 |
| gaggttgctt cgcgactgga gaagtttaca aagctctacc aagaagaatt ccagaaagca | 180 |
| ctgaaaaaat agctcgagtg aggtgtatgc agtcatagaa taatatgggt agtaataaag | 240 |
| aattctgatt | 250 |

<210> SEQ ID NO 115
<211> LENGTH: 46
<212> TYPE: DNA
<213> ORGANISM: Ostertagia ostertagi

<400> SEQUENCE: 115

| | |
|---|---|
| tcgtcgtcgt cgatcgtcgt cgtcgacccc acacgaccct cacaca | 46 |

<210> SEQ ID NO 116
<211> LENGTH: 619
<212> TYPE: DNA
<213> ORGANISM: Ostertagia ostertagi

<400> SEQUENCE: 116

| | |
|---|---|
| tgatccatgc ggttgatggc gactgtcgtc ttgccgtgct cgctgcggta gcccacccca | 60 |
| tgggtgtccg gcatgaaata gctgtccatc tccacgaggg taaggcggcc ccgtaccatc | 120 |
| tgtgcggcca cgtggctttc caccgtgtca aagatggcaa gctcgccgac gcgaatgcca | 180 |
| taaagcgtct ccagatcctc cagcggcacc ttgaaaaagg taaactgatc accttcaaag | 240 |
| tcctggttca gggtgaagcc cagcattgct tccggcggca ggttctgtgc agcaagaacc | 300 |
| tcgatccaca gatcaacgta gcagtttgtc tccggccaaa tccggtcctg cgcatgcagg | 360 |
| gcatgcggcc ggtaggtctg cggatcgata tgggggaaaa cagcttgcat gccgccggtc | 420 |
| agccccacaa ttcctggcga acctgttccg gccaggcttc gatatcgagg ccatgatggt | 480 |
| ggaacagggc aagcgcaatc cgctccaggc caaatccgac acaggcagta tgggcggtcg | 540 |
| tgccatcagc gaattgaatg ccccatttcg tgccgaaatg atcctgatga tagttgaagc | 600 |
| ttatgcatgc ggccgcaag | 619 |

<210> SEQ ID NO 117
<211> LENGTH: 118
<212> TYPE: DNA
<213> ORGANISM: Ostertagia ostertagi

<400> SEQUENCE: 117

| | |
|---|---|
| atcgatccga tccgatccga tccgatccga tccgatccga tccgatccga tccgatccga | 60 |
| tccgatccga tccgatcgat ccgatcgatc cgatccgatc cgatccgatc cgatccga | 118 |

<210> SEQ ID NO 118
<211> LENGTH: 122
<212> TYPE: DNA
<213> ORGANISM: Ostertagia ostertagi

<400> SEQUENCE: 118

| | |
|---|---|
| acttgagggg aggcgccaag aaggttgtca tctccgcacc atcagcagat gccccgatgt | 60 |
| ttgttatggg tgtaaacaac gagacttaca acgctgccaa caaccacatt atcaggaacc | 120 |
| cg | 122 |

<210> SEQ ID NO 119
<211> LENGTH: 98
<212> TYPE: DNA
<213> ORGANISM: Ostertagia ostertagi

<400> SEQUENCE: 119

```
catcgatcga tccgatccga tccgatccga tccgatccga tccgatccga tcgatcgatc    60
gatcgatcga tcgatcgatc gatcgtcgat cgtcgtcg                            98
```

<210> SEQ ID NO 120
<211> LENGTH: 50
<212> TYPE: DNA
<213> ORGANISM: Ostertagia ostertagi

<400> SEQUENCE: 120

```
gatccgatcc gattccgatc cgatccgatc cgatcgtcgt cgtctctccc               50
```

<210> SEQ ID NO 121
<211> LENGTH: 602
<212> TYPE: DNA
<213> ORGANISM: Ostertagia ostertagi

<400> SEQUENCE: 121

```
gaccagaacg ccaccactac acaatgttgg agtacaaatg agtacaccgc attttactga    60
caggtatccc tatgtgcgtt atagctacgg aaatacggac acctccttag gcatcgctac   120
tcaatccgag tctgtatacg ctagaagtac tgccgttcga gatattggta cgaaacggtg   180
gttggaaggc aagttgaccg cgtacaaccc atctcaattt caacatcgag cggactatag   240
accaacatac gaacgtccac atgtgccaca gagaagctac ataaggtaca tgcctgttga   300
cgacgccgtc gatatgtata agaagagatg catgactgtt gggaccctgt caaagtactg   360
gctatcccct gccacgtggg cctctcgaag agacaaggaa ttgaatctgt catcgtcgct   420
gagtcgtgga aattacacct acaccaacaa atataacaga ttcagcagcc gtctatacta   480
actgcagaaa cactgccctt acatcatttg gtctatcagc tatcaaacgt ttccgacctt   540
tcattatgtt cgatcgtttg ctcatatctt aacggaggaa tactattgaa tgaatctttt   600
at                                                                  602
```

<210> SEQ ID NO 122
<211> LENGTH: 99
<212> TYPE: DNA
<213> ORGANISM: Ostertagia ostertagi

<400> SEQUENCE: 122

```
atcgatcgat cgatcgatcg atcgatcgat cgatcgatcg atcgatcgat cgatcgatcg    60
atcgatcgat cgatcgatcg atcgatcgat cgatccgga                           99
```

<210> SEQ ID NO 123
<211> LENGTH: 284
<212> TYPE: DNA
<213> ORGANISM: Ostertagia ostertagi

<400> SEQUENCE: 123

```
ggaagaagtg cggtgaagaa ggtggagcga aatgctgcga aggaaaacca tgctgcaagt    60
aatttcgccc gagatgtcga acggtggacg tggtcatcat ggtcgcctag ctatctgcga   120
tctacaccac tgatcaacag cgataattcc cttgtgcagc tgtaatttcg tatttaaatt   180
```

```
tccatatttg tccgtttgtt tgtgttcagt gtgagtgtga aagcgcgata attgtgtttt    240
taagtgtgta ttcctcatcg gcatagtcga ataaaatttt ctgc                    284

<210> SEQ ID NO 124
<211> LENGTH: 114
<212> TYPE: DNA
<213> ORGANISM: Ostertagia ostertagi

<400> SEQUENCE: 124
gatccgattc cgattccgat tccgatccga tccgatccga tccgatccga tcgatccgat     60
ccgatcgatc gatcgatcga tcgatcgatc gatcgatcga tcgatccgat ccga          114

<210> SEQ ID NO 125
<211> LENGTH: 100
<212> TYPE: DNA
<213> ORGANISM: Ostertagia ostertagi

<400> SEQUENCE: 125
atcgatccga tccgatccga tccgatccga tccgatccga tccgatccga tcgatccgat     60
cgatcgatcg atcgtcgtcg atcgtcgtcg tcgtcgatcg                          100

<210> SEQ ID NO 126
<211> LENGTH: 91
<212> TYPE: DNA
<213> ORGANISM: Ostertagia ostertagi

<400> SEQUENCE: 126
atcgatcgat ccgatccgat ccgatccgat ccgatccgat ccgatccgat ccgatcgatc     60
gatcgatcga tcgatcgtcg tctcgtcgtc c                                    91

<210> SEQ ID NO 127
<211> LENGTH: 200
<212> TYPE: DNA
<213> ORGANISM: Ostertagia ostertagi

<400> SEQUENCE: 127
gattcgattc cgattccgat tccgattccg attccgattc cgattccgat tccgattccg     60
attccgattc ccgatttccg atttccgatt tccggatttt ccggaatttc cggattttcc    120
ggaatttccg gaatttcccg ggaatttttc cgggaaattt tcccgggaat tttttcccgg    180
ggaaattttt cccggggaaa                                                200

<210> SEQ ID NO 128
<211> LENGTH: 105
<212> TYPE: DNA
<213> ORGANISM: Ostertagia ostertagi

<400> SEQUENCE: 128
cgatcgatcc gatccgatcc gatccgatcc gatccgatcc gatccgatcc gatccgatcc     60
gatccgatcc gatcgatcga tcgatcgatc gatcgatcgt cgtcg                    105

<210> SEQ ID NO 129
<211> LENGTH: 73
<212> TYPE: DNA
<213> ORGANISM: Ostertagia ostertagi

<400> SEQUENCE: 129
gggacgtttc gatccatcga attcgattcg tctcgacgaa cacgcgtctc atcacgtctt     60
catagtcttg aga                                                        73
```

<210> SEQ ID NO 130
<211> LENGTH: 101
<212> TYPE: DNA
<213> ORGANISM: Ostertagia ostertagi

<400> SEQUENCE: 130
gggcaatttt caaattcaaa ttcaaattca aatcggattc ggtttcgatc atcgatttca      60
ttcatttcgt ctcatttgtt atgttgattg gtcgagtgtt a                        101

<210> SEQ ID NO 131
<211> LENGTH: 136
<212> TYPE: DNA
<213> ORGANISM: Ostertagia ostertagi

<400> SEQUENCE: 131
tattttgtta agttgattgg gtcagtgttt agtggaagag cctttactac cactaagtcc     60
tattttttcg tttatttatt tttttattat ttttattatg atattaatat ttaattttag    120
taaaaaattg tttatt                                                    136

<210> SEQ ID NO 132
<211> LENGTH: 150
<212> TYPE: DNA
<213> ORGANISM: Ostertagia ostertagi

<400> SEQUENCE: 132
gggggatccg gattccgatt tcccggaaat tccggatttc gaatttccc ggattcccga      60 ttcccgattc cggattccga ttccggattc cgatccgatt ccgattccga tccgatccga    120
tcgatccggt ccgatccgaa tcgatcgtcg                                     150

<210> SEQ ID NO 133
<211> LENGTH: 18
<212> TYPE: DNA
<213> ORGANISM: Ostertagia ostertagi

<400> SEQUENCE: 133
gaaaaaaaaa aaaaaaaa                                                   18

<210> SEQ ID NO 134
<211> LENGTH: 93
<212> TYPE: DNA
<213> ORGANISM: Ostertagia ostertagi

<400> SEQUENCE: 134
gggacttcat ccggatcgat tcatcctcat cctcggattc gatcgtccat ccgaacgacc     60
acatcgacga tcgaatcacg tcgatcgatc cga                                  93

<210> SEQ ID NO 135
<211> LENGTH: 400
<212> TYPE: DNA
<213> ORGANISM: Ostertagia ostertagi

<400> SEQUENCE: 135
gacggggatt tacggaatgt tactactgga ttgagtctcc aaaaggaacc acaatcgaag     60
tgaaattagc ggattaccca tggggttatg ttggttcagg atgcagtgtt gctggtttcg    120
agctcaaaac caacaagaac caaacactta ctggctacag gttctgcact cctgagggtg    180
ttggacatgt gtttcaatct tacacaaatc gtgtgccagt gattacgtac agcagctctc    240

```
tttataatttt cataaccact gaactcgaat atcgatacgt tcctggacgt ccatctgcct      300
aaacgatttc tgcatatgga cactattatg gccatcagag tgataaagtg ctgaagtgac      360
ttttctgttg ctaaacttcg cggtttaata aagttttcgc                            400
```

<210> SEQ ID NO 136
<211> LENGTH: 99
<212> TYPE: DNA
<213> ORGANISM: Ostertagia ostertagi

<400> SEQUENCE: 136

```
gcatcgatcg atccgatccg atccgatccg atccgatccg atccgatccg atccgatcga      60
tcgatcgatc gatcgatcga tcgatcgatc gtctcgtcg                             99
```

<210> SEQ ID NO 137
<211> LENGTH: 100
<212> TYPE: DNA
<213> ORGANISM: Ostertagia ostertagi

<400> SEQUENCE: 137

```
gatcgatcga tccgatccga tccgatccga tccgatccga tccgatccga tccgatcgat      60
cgatcgatcg atcgatcgat cgatcgatcg tcgatcgtcg                            100
```

<210> SEQ ID NO 138
<211> LENGTH: 136
<212> TYPE: DNA
<213> ORGANISM: Ostertagia ostertagi

<400> SEQUENCE: 138

```
gggggaatcg gattttccga aaatttcccc cgaattttcc cgggattccg gattccggat      60
ccccggattt cggatttcga aattcgatcc gaattcgatt tcgattcaa tcgaacgcgg       120 tcgtcacagt acgtcg                                                      136
```

<210> SEQ ID NO 139
<211> LENGTH: 184
<212> TYPE: DNA
<213> ORGANISM: Ostertagia ostertagi

<400> SEQUENCE: 139

```
gggacgatcg atccgatttc cgattccgga tcccggatcc cgattcccga ttccggatcc      60
cggaattccg aatcccggaa tccggaattt ccggatttcc ggattcccga tttccgaaat     120
tttccggatt ttccggattt ccggattttc cggatttttc cgaatttccg aaaatttttc     180
cgga                                                                   184
```

<210> SEQ ID NO 140
<211> LENGTH: 53
<212> TYPE: DNA
<213> ORGANISM: Ostertagia ostertagi

<400> SEQUENCE: 140

```
gcctcatcga tcgatcatca tcatcatcat cgtctcatct ctcgtcgtct ctc              53
```

<210> SEQ ID NO 141
<211> LENGTH: 96
<212> TYPE: DNA
<213> ORGANISM: Ostertagia ostertagi

<400> SEQUENCE: 141

```
ggaattatct ttggaaaaaa aaaaaaaaca atcgatcgt ccgtccgtcc gtccgccgtc       60
```

```
gatcgtctca tcgatcgatc gatcgacgac gatcga                                  96

<210> SEQ ID NO 142
<211> LENGTH: 57
<212> TYPE: DNA
<213> ORGANISM: Ostertagia ostertagi

<400> SEQUENCE: 142
gggccgtcac gtcgatcatc gacgcaacgt cgctgtcgtg tcatcagtcg tgacacg         57

<210> SEQ ID NO 143
<211> LENGTH: 62
<212> TYPE: DNA
<213> ORGANISM: Ostertagia ostertagi

<400> SEQUENCE: 143
gggctggcac ggaattcctt cactcacgat cgtgttgttt ggagatagct gtgagtgctg       60
cg                                                                       62

<210> SEQ ID NO 144
<211> LENGTH: 249
<212> TYPE: DNA
<213> ORGANISM: Ostertagia ostertagi

<400> SEQUENCE: 144
aaatactaga atgtgttgtt tttgggagaa tagctggtgg aagtgctgcg tctattaatt       60
atggccatga agaactttga gtttccagca cttacaattt caaaatgtga tctgtcacga     120
gtttttacgt agccggttgt tcataatca ggccattata attgtttggg cagcatagta       180
ttttattgtt cacttttga catgtttggc tttgtgtgtt gtgaatactg acaataaagt       240
aattcgtac                                                              249

<210> SEQ ID NO 145
<211> LENGTH: 63
<212> TYPE: DNA
<213> ORGANISM: Ostertagia ostertagi

<400> SEQUENCE: 145
gggaatgttg acagtgaaga gtaattgttc ttgttatcat aatgtgttta aaaaaaaaac      60
gcg                                                                     63

<210> SEQ ID NO 146
<211> LENGTH: 73
<212> TYPE: DNA
<213> ORGANISM: Ostertagia ostertagi

<400> SEQUENCE: 146 gggtataccht gtggcggatt cattttgata tttggcaaac taatacaatt atgcaaaaaa     60 aaaaaaaaa atg                                                           73

<210> SEQ ID NO 147
<211> LENGTH: 67
<212> TYPE: DNA
<213> ORGANISM: Ostertagia ostertagi

<400> SEQUENCE: 147
gggattcacg tcggctcatc cagcttggct cgacagtgaa tcgaccacga cagtgtcatc      60
caacaca                                                                67
```

<210> SEQ ID NO 148
<211> LENGTH: 159
<212> TYPE: DNA
<213> ORGANISM: Ostertagia ostertagi

<400> SEQUENCE: 148

```
gggcacaaga atcgaccacg acagtgtcat ccaacacagt gccggtaact atcccgatca      60
aggtaccccg ggcgtttcca gaaactggat cgttcggatc attcggatct tatggaaagg     120
ctggtcttgc atgctaatca aataaagcat ttggtttac                            159
```

<210> SEQ ID NO 149
<211> LENGTH: 41
<212> TYPE: DNA
<213> ORGANISM: Ostertagia ostertagi

<400> SEQUENCE: 149

```
gctcatctcg atcgtcatca tcatcatcgc atccctcctt a                          41
```

<210> SEQ ID NO 150
<211> LENGTH: 61
<212> TYPE: DNA
<213> ORGANISM: Ostertagia ostertagi

<400> SEQUENCE: 150

```
ggcccttcac tcgatgtcac acatcatcgc atagcttatg ttatatttga taagttagaa      60
g                                                                      61
```

<210> SEQ ID NO 151
<211> LENGTH: 177
<212> TYPE: DNA
<213> ORGANISM: Ostertagia ostertagi

<400> SEQUENCE: 151

```
ggcattcgat ccgatcgatc cgggatccga tccgatccga ttccggattc cgatccgatt      60
ccgggatccg atccggatcc cgggaattcc gaattccggg atttccggga ttccggaatc     120
ccgaaaaatt cccggatttc cccccccggat ttcccgggga tttcccgggg gggggaa       177
```

<210> SEQ ID NO 152
<211> LENGTH: 99
<212> TYPE: DNA
<213> ORGANISM: Ostertagia ostertagi

<400> SEQUENCE: 152

```
gatcatcgat cgatccgatc cgatccgatc cgatccgatc cgatccgatc cgatcgatcg      60
atcgatcgat cgatcgatcg atcgatcgat cgatcgatc                             99
```

<210> SEQ ID NO 153
<211> LENGTH: 59
<212> TYPE: DNA
<213> ORGANISM: Ostertagia ostertagi

<400> SEQUENCE: 153

```
gggatactgg atcagacagc acaccattcc tctgtcttca gtaacctata gagatataa       59
```

<210> SEQ ID NO 154
<211> LENGTH: 86
<212> TYPE: DNA
<213> ORGANISM: Ostertagia ostertagi

<400> SEQUENCE: 154
```

```
aggcacatcc catttcctct gttcttaagt aaaaccctat agagaatata actaacttga    60
taaaagacag tgcttcttat tcaaga                                         86

<210> SEQ ID NO 155
<211> LENGTH: 65
<212> TYPE: DNA
<213> ORGANISM: Ostertagia ostertagi

<400> SEQUENCE: 155
ggtacgaaag gagaaccatc gcaacaacga acgactcgta gtgttccggt cgtcgcactg    60
cagtg                                                                65

<210> SEQ ID NO 156
<211> LENGTH: 133
<212> TYPE: DNA
<213> ORGANISM: Ostertagia ostertagi

<400> SEQUENCE: 156
gcaaaacata cgaagactgt aagtgttccg gctgcacttg cagtgtagaa gaagcgctct    60
gtgttgctcc ttaacaccta tgtcaataaa ttttcatcaa taaaaaaaaa aaaaaaaaaa   120
aaaaaaaaaa ttg                                                      133

<210> SEQ ID NO 157
<211> LENGTH: 66
<212> TYPE: DNA
<213> ORGANISM: Ostertagia ostertagi

<400> SEQUENCE: 157
gggcgaatca tcgaatcgcg accgcgcaat tcgtcacgtc gacttcgtga cgcgtagtac    60
tgcacg                                                               66

<210> SEQ ID NO 158
<211> LENGTH: 289
<212> TYPE: DNA
<213> ORGANISM: Ostertagia ostertagi

<400> SEQUENCE: 158
caatgtgagc gtagtacttg caagcgccca tttgctatca tagcactgat ttctctcgtc    60
tttttctcag ttattgaagg tttatattct atccgtgtgg tttccttaat atttagtcaa   120
ccaaaagagt gttatgctca acacagtcgt tgacggattg gtggttgttc attcttcgct   180
gccgacctcg cgaatgtctc gagaagaacc aactgcttcc gttcatcccc tcatgcaagt   240
catatgtcat acagtgtgtt atgagattat tgtgatgaat aaagagttg               289

<210> SEQ ID NO 159
<211> LENGTH: 170
<212> TYPE: DNA
<213> ORGANISM: Ostertagia ostertagi

<400> SEQUENCE: 159 gggggatcc aaaatcggaa tccggaaatc ccgaatccgg gaatcccgaa atccggatcc     60
ccgaatcgga atcccgattc gggattccgg aaatcggaaa tcggtcccga ttcggtcccg   120
gatcccgaat cggaatcgga aatcggaaat cgggaatcgg gaaacgggaa               170

<210> SEQ ID NO 160
<211> LENGTH: 122
<212> TYPE: DNA
```

```
<213> ORGANISM: Ostertagia ostertagi

<400> SEQUENCE: 160
gtaaatctga catccaaaac aacgatcgat cactctcatc tctcatcatc tacatgttct      60
tctcctcgct ttcgacactt cttgaacaat ttcgctattg tgtgagtgtg taaaacgtgg     120
ct                                                                    122

<210> SEQ ID NO 161
<211> LENGTH: 95
<212> TYPE: DNA
<213> ORGANISM: Ostertagia ostertagi

<400> SEQUENCE: 161
gggacgatcg gatcctcgat ccgattcgga tccatcgtcc atccaatcac accatccggt      60
cgtcggatcg atcgtcgttc gtcgccaacc accga                                 95

<210> SEQ ID NO 162
<211> LENGTH: 48
<212> TYPE: DNA
<213> ORGANISM: Ostertagia ostertagi

<400> SEQUENCE: 162
ggatcgtccg tcgtccgtca tcgatcacgc tcgcgtgtgc gtacacac                   48

<210> SEQ ID NO 163
<211> LENGTH: 77
<212> TYPE: DNA
<213> ORGANISM: Ostertagia ostertagi

<400> SEQUENCE: 163
gggggagtca tccgaacgat cggtcgtcga cgtcgtcgga cattcggttc acgctattga      60
tgctgatcac gatcgtc                                                     77

<210> SEQ ID NO 164
<211> LENGTH: 49
<212> TYPE: DNA
<213> ORGANISM: Ostertagia ostertagi

<400> SEQUENCE: 164
ggtgtccatc gtccgatcat cgcacgatcg acgtcgctct cctccgtgc                  49

<210> SEQ ID NO 165
<211> LENGTH: 163
<212> TYPE: DNA
<213> ORGANISM: Ostertagia ostertagi

<400> SEQUENCE: 165
gctcatcgat cgaatcgaat cgatccgatc cgattccgat ccgatccgaa ttccgaatcc      60
gaatcccgat tccgattcc gaattccgga tttcccgggg attcccggaa tttttcccgg     120
aattcccggg gaattcccgg aatttcccgg gaattccccg gaa                       163

<210> SEQ ID NO 166
<211> LENGTH: 79
<212> TYPE: DNA
<213> ORGANISM: Ostertagia ostertagi

<400> SEQUENCE: 166
ggtaacgatc gatcgatcga tcatccgtcc atcgatcatc gtctcatcgt cgatcacgac      60
gtcgatctcg acatcatcg                                                   79
```

```
<210> SEQ ID NO 167
<211> LENGTH: 388
<212> TYPE: DNA
<213> ORGANISM: Ostertagia ostertagi
<220> FEATURE:
<221> NAME/KEY: misc_feature
<222> LOCATION: (329)..(329)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (364)..(364)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (373)..(374)
<223> OTHER INFORMATION: n is a, c, g, or t
<220> FEATURE:
<221> NAME/KEY: misc_feature
<222> LOCATION: (377)..(377)
<223> OTHER INFORMATION: n is a, c, g, or t
<220> FEATURE:
<221> NAME/KEY: misc_feature
<222> LOCATION: (380)..(380)
<223> OTHER INFORMATION: n is a, c, g, or t

<400> SEQUENCE: 167
ggcggcatgc ggcgtgtcct tgtttaacgg aacggaatga agaagagaaa aagctttctt      60
aaagtaacga ggccaataac ggatcgcaat gaagatctaa tagagctgta cggctacttc     120
tctgatttcc ttcagtatac aaaaaatgtt gttagtatcc gcaatcgtct aggggaaacg     180
atcttattaa gaaagtagaa agaaatagct aacacctatt tcgtttcttg atttttttgaa    240 ccactggcgt aaatgctctt acacatgttt cccatgaaac cagggttttc cgttatccta     300
gtcttcctca taatcaaatg atctggtant tcctggatgn cgtttcctct ttctaccaag     360
accntcatcn tcnnatnacn acaacgcc                                        388

<210> SEQ ID NO 168
<211> LENGTH: 99
<212> TYPE: DNA
<213> ORGANISM: Ostertagia ostertagi

<400> SEQUENCE: 168
atcgatcgat ccgatccgat ccgatccgat ccgatccgat ccgatccgat ccgatcgatc      60
gatcgatcga tcgatcgatc gatcgatcga tcgatcgtc                            99

<210> SEQ ID NO 169
<211> LENGTH: 217
<212> TYPE: DNA
<213> ORGANISM: Ostertagia ostertagi

<400> SEQUENCE: 169
cggcttacgg ccggggacgt gaacaggcag ccaaggccgc aaaagaggcg aacaaagcag      60
ctcgagcagc caaagctgcc atgaacaagg aaaagaagcc cgctgcacaa aaaatgaaac     120
caccgaagcc agtgaagact gctgcacccc gagtcggagg aaaacgttaa gcttggatag     180
catgttgttt gttattgcaa ataaatattg ttatcgt                              217
```

<210> SEQ ID NO 170
<211> LENGTH: 328
<212> TYPE: DNA
<213> ORGANISM: Ostertagia ostertagi
<220> FEATURE:
<221> NAME/KEY: misc_feature
<222> LOCATION: (9)..(9)
<223> OTHER INFORMATION: n is a, c, g, or t

<400> SEQUENCE: 170

| | | | | | |
|---|---|---|---|---|---|
| catcggccnt | aggcggggt | atgaagaata | tcgacaaaga | cgatacttgc | gttatgtatt | 60 |
| ctgtgctggc | gtatgacgca | accagtgaaa | ttcacgaaac | tattgtgatg | gttctcataa | 120 |
| agaatgagac | gggaaaagtc | agatctcact | acttcaagta | tcaggtgata | actgataaga | 180 |
| caacaaagaa | acaaagcact | tggattgacg | acatggacgc | gcttaatttc | atgttaacga | 240 |
| taagaaagtg | taagctcgtc | ccttctagag | gttaaaatcc | gtcttgaatg | aatggacatg | 300 |
| gaaataaatt | ttcgcagctg | taagaagg | | | | 328 |

<210> SEQ ID NO 171
<211> LENGTH: 283
<212> TYPE: DNA
<213> ORGANISM: Ostertagia ostertagi

<400> SEQUENCE: 171

| | | | | | |
|---|---|---|---|---|---|
| acggatatca | aggtcgatta | caagtcacat | aacaaagctg | gtgaatacca | gttagttagc | 60 |
| tgtagaaggc | caataagtga | cgaggaattg | gaggatccag | acgttgctat | gaagcaactg | 120 |
| gaactgcaaa | tcaaaaagga | aatgctgatc | tcggatttaa | tgaagtctaa | gcgaaagctt | 180 |
| acaaagaag | agctgagtat | tctcaatgag | gaactgcctg | ttggacaagc | gaaaaagtca | 240 |
| tgaccgatca | ctcagttgta | gtatagctag | gttttcaatt | aac | | 283 |

<210> SEQ ID NO 172
<211> LENGTH: 304
<212> TYPE: DNA
<213> ORGANISM: Ostertagia ostertagi

<400> SEQUENCE: 172

| | | | | | |
|---|---|---|---|---|---|
| cggcttacgg | ccggggtgga | acaagatttt | ccgcatcctt | aaggccaagg | gcatggctcc | 60 |
| ggaaatccct | gaggatctct | accatctgat | caagaaggcg | gtatccatcc | gaaagcacct | 120 |
| tgagcactcg | cgcaaggaca | ttgacagcaa | atacagattg | attcttgttg | agtctcgaat | 180 |
| ccatcgtttg | gctcgctact | acaaaaccag | ccgtcaactc | ccagcgacct | ggaagtatga | 240 |
| gtcggcgacc | gctgcctcac | tcatctcata | aagttgtttt | gtgattattt | gttataaatt | 300 |
| gttg | | | | | | 304 |

<210> SEQ ID NO 173
<211> LENGTH: 214
<212> TYPE: DNA
<213> ORGANISM: Ostertagia ostertagi

<400> SEQUENCE: 173

| | | | | | |
|---|---|---|---|---|---|
| ggcattacgg | ccgggagagg | agggaagttt | acaaaccata | ctactttgaa | tacatagagg | 60 |
| aggaagacaa | gataacaaag | aagtccactc | gcaaatagg | tccgttgacc | gaagaggaat | 120 |
| tcacaactaa | atataaccat | tgcaaaaggt | ggtgataatg | gtcgtcttga | acaaaatttt | 180 |
| gtccacttcg | atgaaaataa | atttcgcaat | tgac | | | 214 |

<210> SEQ ID NO 174
<211> LENGTH: 411
<212> TYPE: DNA
<213> ORGANISM: Ostertagia ostertagi

<400> SEQUENCE: 174

```
cggcattacg gccggggcat agaacaattg tattgaatga taccatatcg catcaagctt      60
atacaagatt aaagaaagga cttgggacct tgaagtatcc ctgcatcgag cgcgctgtca     120
tacaggaatt tctgtactgg ctcaagatgg aaatgtcgct aaaatatat tacaccctcc      180
gcggtctcga gatgtacagg actgatatcg aggagcttcc cgaaggagcg caatatggat     240
gccaccatct ccttgctcga ggttatagct ttcagctcat gcgtattttt tgcttcttcc     300
gaacaaccct aaaaaatgat tggattatcc attaatgacc tttataaggt ctgtaaattt     360
cgctacatta tgtgctcgtt tgataaaatc tgcataaaac gattccgtac g              411
```

<210> SEQ ID NO 175
<211> LENGTH: 432
<212> TYPE: DNA
<213> ORGANISM: Ostertagia ostertagi

<400> SEQUENCE: 175

```
cggcattacg gccggggagt caaatgttgt tcgtcctcac aatcctgtcc ttcctcttgg      60
tgaatcttgg cgcctcggat cagcttaaat ataaacagtg cttggacccc ataagcatgg     120
ctgacgtgtt tgtgtggttt ttcttccggg aggctagacg agatatggaa tgggattgga     180
tagctgcaac tgcggctgag aaggcattgg ctgacccttc tctcgaaatg cgggacttct     240
ggaaagccag caatggagag acacacgtcc gtttatgggg gcgtccactc aatatggtga     300
tgaagttgac aaaaaccctt caagggtaca ggaaacgttt tccagatatc atgaagatga     360
agagtaaaat atatggatgc tggtgcaggt gcgaccttag tgaaaccgtc ctagaaacgg     420
tttgcttttt cc                                                         432
```

<210> SEQ ID NO 176
<211> LENGTH: 326
<212> TYPE: DNA
<213> ORGANISM: Ostertagia ostertagi

<400> SEQUENCE: 176

```
gggcattacg gccggggaca ctcgaaatgt tgcccatcct tggactgttc ctgctgttcc      60
ttggaaatgt caacgctcag gggaaagaac ctttgccgaa acggtgcgaa aagatctatg     120
agaggttcat taaggagcac accagaggtt tgacttggaa tgacgaactg gcgtccgaag     180
ctttggatat gctgatgcga ggatattcta tggacttttc atatgacttg aagcttctag     240
tgtcagggac gtttccgaat agtgataatt cgtcattgga ggacaaggtt tctctcacct     300
tggaaagtgc catctttaca ccagaa                                          326
```

<210> SEQ ID NO 177
<211> LENGTH: 48
<212> TYPE: DNA
<213> ORGANISM: Ostertagia ostertagi

<400> SEQUENCE: 177

```
cggcattacg gccggggtcc acttcgatga aataaatttc gcagttgt                   48
```

<210> SEQ ID NO 178
<211> LENGTH: 423
<212> TYPE: DNA

<213> ORGANISM: Ostertagia ostertagi

<400> SEQUENCE: 178

| | |
|---|---|
| tcggcttacg gccggggtgc gcaagtattt caaaggtgct gaaagcttca ctgccgatga | 60 |
| cgtccaaaaa agcgataggt ttgccgtcca aggtatggct ctgctcacat ccgtgcacat | 120 |
| tcttgccgac acctatgaca atgagatgat cttccgtgcc ttcgtccgtg atctcatgaa | 180 |
| ccgacataag gagcgaggac ttgacccctaa actctggaag gacttctggg atatcttcga | 240 |
| gaagttcctg gagaaccgca agccactaac tgctgaccag aagactgcgc ttgatgcgat | 300 |
| gggcacaaga ttcaacgatg aagctcagaa gcaactggcc gtccttggac ttccacacac | 360 |
| ataagaaact ctcttgggaa atgcctaggt cttgatgcgt cagtgaataa agtgttgtca | 420 |
| gcg | 423 |

<210> SEQ ID NO 179
<211> LENGTH: 288
<212> TYPE: DNA
<213> ORGANISM: Ostertagia ostertagi

<400> SEQUENCE: 179

| | |
|---|---|
| tcggcttacg gccgggggat gcgcggtgca ttggtgccct gacatgacat tcgccgcgtg | 60 |
| cgagtataat cccgctggaa atcttcttgg ttctgttgtt tacgaaaaag gagatccatg | 120 |
| tacaactgac gccgactgcc agtgcgaagg ttgcgtttgc agcagagatg aggcgctatg | 180 |
| cattgcccca gcacattgat ttagctgtca ttctcaaccc acttttttcaa agtttgtgtg | 240 |
| cttttgacagt ttcaaaggat tcatcaacag tcaaataaaa ggttttac | 288 |

<210> SEQ ID NO 180
<211> LENGTH: 469
<212> TYPE: DNA
<213> ORGANISM: Ostertagia ostertagi

<400> SEQUENCE: 180

| | |
|---|---|
| cggcattacg gccgggaggg agagacgaac aggatgatca ccgaattgat attataagtg | 60 |
| cagagaaagg aacagcatca acagaccgtg tgacgacacc attcatgacg aagtatgaac | 120 |
| gcgctcgagt tttaggtaca cgtgctcttc agattgctat gggcgcaccg gtgatggtcg | 180 |
| agttggaaga agaaacggat ccactggaaa ttgctcgcaa ggagctaaaa catcgacgta | 240 |
| ttccaatcat tgttcgacga tacctaccag atggctcatt tgaagattgg tccgtcgatc | 300 |
| agctgcatgt gaccgactgg tgatatggct gaccatgtaa cttctgtttc ctgttacctt | 360 |
| tcttctcata cctgttgatc ttcatgagcc tttttttta catatttggt tatatgttat | 420 |
| gtcatatttg gagctataca cacatcctcc cagcaatgaa gtgattgac | 469 |

<210> SEQ ID NO 181
<211> LENGTH: 394
<212> TYPE: DNA
<213> ORGANISM: Ostertagia ostertagi

<400> SEQUENCE: 181

| | |
|---|---|
| gcatacggcc ggggagggct ctgatgtggt ttgagcagtt ttattccggg gtcattacaa | 60 |
| tcgcgtttgt tgctggtgca tgttatatga gttatccttt caataaatgg gatgttggac | 120 |
| gagcctatcg aagggattac tgcactcctg caagaattga gctgtcgaag cgtgatcatc | 180 |
| gtttaactgg gaaccaatat gtcatctccg gtctggaatc gatcatcaaa tagattgtcg | 240 |
| gaactttga tgctctgcta ggtgttggaa gattggagtt ttctcactgt cattgtagaa | 300 |

```
gtacatttga taactttgat tgtgtcgtgt agctatagat tgatgaatat tagaatattt    360
tttggtttca tcatcggaat gaaattcgaa ccct                                394

<210> SEQ ID NO 182
<211> LENGTH: 382
<212> TYPE: DNA
<213> ORGANISM: Ostertagia ostertagi

<400> SEQUENCE: 182
agagcgatga acgcacgtta tgtgaagagc ccaagacata ctattcaagt cgattacatt     60
gaatacatgg atgaattagc cagcttagtt ggatgcaagc cgaacatcgc gcagattttc    120
aaatcagatc cgattttagc attacagctc tactttggtc catgcgttcc gtacgcgtac    180
aggctgcagg ggcctcatcc ttggtcagga gctcgagacg caataatgac agttgatgaa    240
agagtgttca aggcgacaaa ttcgaacagg tacaaggcct ccactgggta tggatacatt    300
atcattgcat cgatacttct tgttttgttg cttatcctac tcttttaatt atgtaccaca    360
accttaaaaa gaatattttt gc                                             382

<210> SEQ ID NO 183
<211> LENGTH: 438
<212> TYPE: DNA
<213> ORGANISM: Ostertagia ostertagi

<400> SEQUENCE: 183
cggcattacg gccggggttc agatgacact gaaaaagagc tcgatcttca tcggaactgt     60
ctgcgataat ggagtcgcaa agaaagctca agtaccacca gaggcatgcc atcacaagat    120
ctacccagag attggtgaca gttcttgga gatgctcagc accccggca gctacgacat      180 ggaagtgatt gagaaggagg ctcatcagtc gaacatcatc aaactgccag cgatcagcag    240
cgctttgaac aactttgtcg ttaagggtga ctggcaggca cagatcgcac tcgttcttgg    300
aggtcagaca atcgcacata tcaaggctcc atcaaatact gattggctct atgtcaacta    360
ggcctggcat tcattggag taacacctag gcagtgattc actgaaattc gcaataaaa     420 aatgaaatat gcaggaac                                                  438

<210> SEQ ID NO 184
<211> LENGTH: 219
<212> TYPE: DNA
<213> ORGANISM: Ostertagia ostertagi

<400> SEQUENCE: 184
cggcattacg gccgggtaca caaatcgtgt gccagtgatt acgtacagca gctctcttta     60
taatttcata accactgaac tcgaatatcg atacgttcct ggacgtccat ctgcctaaac    120
gatttctgca tatggacact attatggcca tcagagtgat aaagtgctga agtgacttt     180 ctgttgctaa acttcgcggt ttaataaagt ttttagttc                           219

<210> SEQ ID NO 185
<211> LENGTH: 369
<212> TYPE: DNA
<213> ORGANISM: Ostertagia ostertagi

<400> SEQUENCE: 185
cggcattacg gccggggaat ggaatgatac tatctctgaa ctagctaggc aagatgtcac     60
gcaaccagca agcttatctt cggctatatt gagaggttat gaagaagcaa gtgattgggt    120
```

```
cgatttttcca ccgaaggatg aacaaccaat ggaggataag gtgaactcga caatgcacac      180
aaagaccttc aatcaacgtc tgtcaaaagt gataagtggt ctaacatgtg acgaagctat      240
gtttggatgc tactgcgatt acggaagtgg accgttttct gacgacatgc agatcaagtg      300
tttcttccaa tgagtttttc aaatcagtaa atttgtgaaa ttttcactgc atgaatgaac      360
tagagacac                                                               369
```

<210> SEQ ID NO 186
<211> LENGTH: 281
<212> TYPE: DNA
<213> ORGANISM: Ostertagia ostertagi

<400> SEQUENCE: 186

```
tcggcattac ggccggggac gctgagggta ttgaaccaga cgatttggag gagatgtaca       60
agaaagctca cgaacgcatt cgaagtcaac cagatcatgt tgctccagct cctaagaaag      120
tcgagaaaaa gagctatcgc atccataaga tcagcttgga ggagagaaag aaacgcattg      180
aggagaagaa agcgctgctc ctgctactga gaaaacagca gacgccgca  atgtcgtgaa      240 tgcacaagct gttgatttac agcaataaag ttgttgaagt c                          281
```

<210> SEQ ID NO 187
<211> LENGTH: 237
<212> TYPE: DNA
<213> ORGANISM: Ostertagia ostertagi

<400> SEQUENCE: 187

```
tcggcattac ggccggggga tgaatggcga aaaggccctg acggcttacc aggctctcct       60
ggtcaagctg gaacccctgg tgaacccggc gagcgtggag tttgtccaaa atactgcgcc      120
attgatggag gagttttctt tgaagatgga acaaggcgtt aaattacatc agatcttgac      180
atatcagcag ttgcttctag gaaattgtac ccaccacaaa ataaatgtat tcaaacg         237
```

<210> SEQ ID NO 188
<211> LENGTH: 248
<212> TYPE: DNA
<213> ORGANISM: Ostertagia ostertagi

<400> SEQUENCE: 188

```
cggcattacg gccggggtga gtgaaaatgt actgaacaca acaataagtg tgtgaagtac       60
gtgaatctat actatatatt tgcgccctta ttcataatgt taggtggatt cgaacgggga      120
ttatgagagt tgccttaaca ttttatcgac ctcatttgtg gtcgaaatat gaaatttgtg      180
tttcaaatgt caaatgttcg ttcaaattat gcgtagatat gtcatgtaaa taaatttcat      240
gaacttct                                                               248
```

<210> SEQ ID NO 189
<211> LENGTH: 278
<212> TYPE: DNA
<213> ORGANISM: Ostertagia ostertagi

<400> SEQUENCE: 189

```
gaatcattgt ttgacgttca agttcatata actagtgttt gctgatgttt tttaaacggt       60
catttattca ttaggatgat gattattcat tgctttgtga ataaacctaa taaataatat      120
caggttcccg ctatttctag ccaattattc accgatatag gaagttgttg ttacgttact      180
agctttgtaa tctgctttgt atgtcattaa agagacttcc gtatagtggc cgttttttcaa     240 agttctcgtg ttattttcag aacaagtaaa gaattctt                              278
```

<210> SEQ ID NO 190
<211> LENGTH: 603
<212> TYPE: DNA
<213> ORGANISM: Ostertagia ostertagi

<400> SEQUENCE: 190

```
tcggcattac ggccggggac gctttcaaag aaggcgcgcg tggagacgca gcgactgata      60
caaccacagc ttctcgacct cggcgcagtt caagcatcag ttctcaaaga caatctgaac     120
gttctagagg cgaacggctt cggattcgag tttaaagatg gcgatgacgg ctgtacaatc     180
cctctgctag tctccgcacc cgttcttcat agttggcaat tgataaaag cgatattgaa      240
gagatcctaa ctgtggtttc gaatttcct ggcgtaatgt accgtccagc taagcttcgc      300
cgaatattcg cttctagagc ccgtcgaaaa tccgtgatga ttggcacaac acttaccacg     360
gcacaaatgc aaactattgt tcatcacctc ggtacactgg atcaaccttg aactgtcca     420
catggtcgcc caactcttcg acatctcgtt gacttgcaaa ataaccctt gtaatgtcta     480
atcactattt cactttctta agttgctatt ggaagtacta atgaacgata tgtttactca     540
tgattttcag ttcaacaaag caagattttg aatatttatt atgttctata aagtttcag      600
ttg                                                                    603
```

<210> SEQ ID NO 191
<211> LENGTH: 302
<212> TYPE: DNA
<213> ORGANISM: Ostertagia ostertagi

<400> SEQUENCE: 191

```
cggcattacg gccgggtcag aagacgagga tttatttacg gaatggttga aggatactgc      60
tggagtgtcc tccaatcatg ctaagagtgc gtacaattgt ctcaatgcgt gggcggagca     120
atatatctga tattgatctg ctaattgaaa tgtttagtgt gaaaattgta tgaattacta     180
cttttgattt catttgttcg tattacggtt cgtggaattc ggtgtgtacg acttaactga     240
cttgttctaa attgtgtcaa tttgtcattt cgatagggat gctcgaataa acgactattt     300
tc                                                                     302
```

<210> SEQ ID NO 192
<211> LENGTH: 113
<212> TYPE: DNA
<213> ORGANISM: Ostertagia ostertagi

<400> SEQUENCE: 192

```
tatagaaaat attgtattta tttatacctt ttatgttaat tatattaatt taatattttt      60
gttgttttat ttaagttaat tataaaaata ttatataaaa ataagtaga gct             113
```

<210> SEQ ID NO 193
<211> LENGTH: 596
<212> TYPE: DNA
<213> ORGANISM: Ostertagia ostertagi

<400> SEQUENCE: 193

```
tcggcattac ggccgggatc gcagatcaag acttgcgcaa ggattggtga gaaaaaatac      60
cggcaggtat cttccaaaag cagcgaacat gttcaaactt gtttataact gttcacttga     120
aacgtcagct agagaagcgg ctgacagatg tacgaccgcc ccatcaacat cacttccaag     180
cggtgtcaaa gaaaatatcc acagcgttgc gaagtcgatg gcccggtatc gtgtcgatgc     240
```

```
tatgaaagag gcggccaggt attggtggaa gcaagtgaga ctcgtcgatg gaattggaat      300
gaaagtcata ttcagagcga agcatgaaag cagcccgatc agatatttca ctctaatggc      360
atgggcaacc accaaaacga tagggtgtgc tgtttctgaa aattgtggaa gcgcatggtt      420
cgtggcgtgc cactactatg ggggaggaag tatggtcgac gatgccgttt acgagagagg      480
cacgccatgc tcagcttgtc ctactggcta cttctgcaat gagatgaagt tatgtcaatc      540
ggcgaattga ttgaattcgt gcacatttct tgtggtaaat gaagttcttc agctcg         596

<210> SEQ ID NO 194
<211> LENGTH: 296
<212> TYPE: DNA
<213> ORGANISM: Ostertagia ostertagi

<400> SEQUENCE: 194
cggcattacg gccgggtgat gaaggcagaa atggagcgat taggtttcaa tccatatggc       60
gaacatgctg aaaagcgatt gaacccgac  tattctaatt cgcctaagga taatcctgct      120
gctaaggcat ttgagggttt agagcaataa gaatgttatc aaatattaaa tatgcttttt      180 tgctttta tt catgagttgt taaaataggt agtgaacatt gtagcattgt tagttttgtt      240
ccagattgtt attattttt gttttgcaca catgacctgt ataaagagtt gttgat           296

<210> SEQ ID NO 195
<211> LENGTH: 503
<212> TYPE: DNA
<213> ORGANISM: Ostertagia ostertagi

<400> SEQUENCE: 195
ggatccaaag ccgactgtcc tcacatatcg actgtcctct aatcttcagt catgaagctg        60
gttgttctgg ctattctgtt gtgcgcggct tattctgtgt atgcacagaa ctgtttctta      120
atcactaatc tgagtggtgc cacatgggga agacagaat tttatcgtga cgaagaactt       180
cgtggaaaga ttgaaaggaa gctggagaag aaaatcggca tagacgatac tttcgttatg      240
tattctgtgc tggcgtttga ggcaaataat gaaattcacg aatctattgt gatggttctc      300
ataaaggatg agaagggaaa agtcagatct cactacttca gtatcaggt gataactgat       360 aggacaacaa aggaacgaag aacctggatt gacgacatgg acgcgcttaa tttcatgtta      420
acgataagaa agtgtaagct cgtcccttct agaggttaaa atccgttttg aatgaatgga      480
catggaaata aattttcgca gtc                                              503

<210> SEQ ID NO 196
<211> LENGTH: 64
<212> TYPE: DNA
<213> ORGANISM: Ostertagia ostertagi

<400> SEQUENCE: 196
ttacggccgg gcagcaagtt caacgaaata tcgtcgaagc accagcacca tgcaaagcat       60
gctc                                                                    64

<210> SEQ ID NO 197
<211> LENGTH: 250
<212> TYPE: DNA
<213> ORGANISM: Ostertagia ostertagi

<400> SEQUENCE: 197
tcggcattac ggccgggatg gagcagaagg taaacgcgac aatgcacggc actcttcacc       60
atcagcttat aacagcggtc aaaaatcaac acgccacttt tggatgctat tgcgagctcg      120
```

```
tcactgatag aagtggatgg agcgatatgt taatcaattg tttcttcaaa tgactccttt    180
ttacttcggc gactttgtca aatttactgc atctaaaatg aaaaaaaaaa tttcgcataa    240
acgttttttg                                                           250
```

<210> SEQ ID NO 198
<211> LENGTH: 751
<212> TYPE: DNA
<213> ORGANISM: Ostertagia ostertagi

<400> SEQUENCE: 198

```
ggcattacgg ccgggtggcc attggatatc aaagttgctc tgattggttc ctgcacaaat     60
tcttcatatg aggatatgac tcgagctgca tccatcgcta agcaggcact tgacaaaggg    120
tcgaaagcta aaaccctgtt cactatcaca cctggatcgg aacaagttcg cgctacaatt    180
gaaagggatg gaatttctaa aattttcagc gacttcggag gaatggtgct ggcaaatgcg    240
tgcggtcctt gcattggaca atgggatcgc aagatgtga agaaaggaga gaaaaatacc    300
attgtcacat catataaccg aaatttcact ggaagaaacg atgcgaatcc cgctacacac    360
ggttttgtca catctcctga cattgttact gcactctcca ttactggaag gctcgacttc    420
gatcccacaa aagatccgat tactgcaccg gatggctcga aattcgtgct caagcctcca    480
acgggagatg atctgccaca gaaggggtac gatcctggtg aggatacttt ccagtcgcca    540
tcacaatctg gagaggttgt ggtcgaccct aaatcggatc gtctgcaact tcttcaaccc    600
ttcgataagt gggatggcaa agacctagag gacatgatca ttctgatcaa agtcaaagga    660
aagtgcacaa ctgatcacat ttcggctgcc ggaccatggc tgaaataccg aggtcatctt    720
gacaactttt ccaacaactt attcctacca g                                   751
```

<210> SEQ ID NO 199
<211> LENGTH: 364
<212> TYPE: DNA
<213> ORGANISM: Ostertagia ostertagi

<400> SEQUENCE: 199

```
gggcattacg gccgggaagg agatcgtgac agagacaggc gagatcgacg ctactgactc     60
atgtggctgt tcggtggaat attctccgtg acatttttgtt atggtgttat ggttgttcgt    120
aatactctgc tcgattaatt attaaactca tattttgtt catgtagtat tctttcggaa     180
ttctaatgat ggttctaaga tttgttgtga aggttttccg tctgtacgtt ccaaatggta    240 ttctttttt tcgcgctgag aatcttgtct tttctgttgc cctattattt atagagattg    300
caaaggtcag tagctttctt tacagttttc gttgcaatca tgtcaataaa aacttcctct    360
gctc                                                                 364
```

<210> SEQ ID NO 200
<211> LENGTH: 21
<212> TYPE: DNA
<213> ORGANISM: Artificial
<220> FEATURE:
<223> OTHER INFORMATION: PCR primer

<400> SEQUENCE: 200

```
ctcgggaagc gcgccattgt g                                               21
```

<210> SEQ ID NO 201
<211> LENGTH: 22
<212> TYPE: DNA

```
<213> ORGANISM: Artificial
<220> FEATURE:
<223> OTHER INFORMATION: PCR primer

<400> SEQUENCE: 201
tgcggccgca tgcataagct tg                                              22
```

PARASITE VACCINE

RELATED APPLICATIONS

Figure 1:
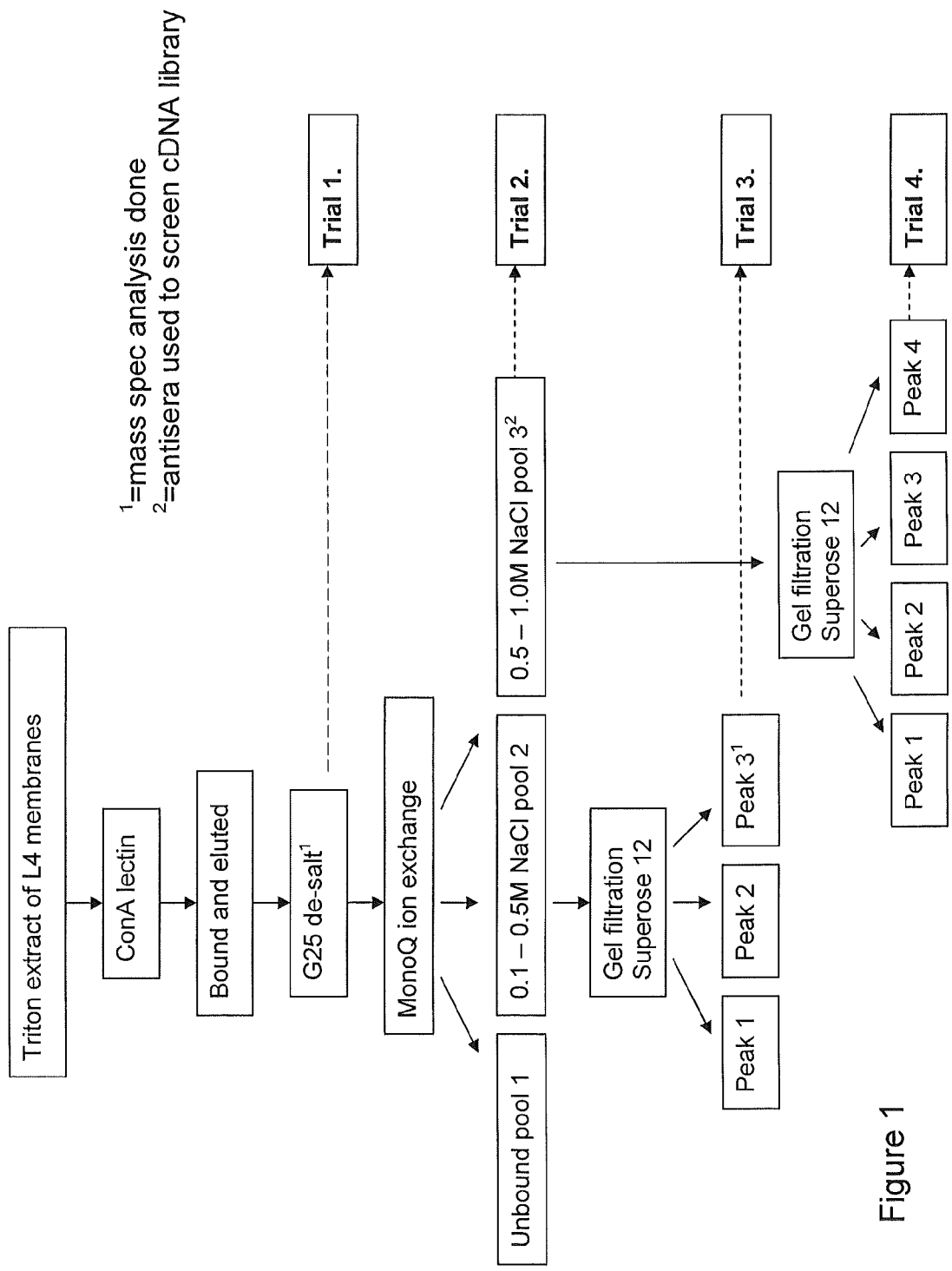

This application is a 35 U.S.C. §371 national phase entry of PCT Application PCT/GB2010/002298, filed Dec. 20, 2010, and published in English on Jun. 23, 2011, as International Publication No. WO 2011/073630, and which claims the priority to United Kingdom Application No. 0922099.7, filed Dec. 18, 2009, the disclosure of each of which is incorporated herein by reference in its entirety.

FIELD OF THE INVENTION

The present invention relates to antigens capable of raising host immune responses to nematode parasites. In particular, the invention provides vaccines for use in protecting against and/or reducing instances of non-blood feeding nematode parasite infections in bovine hosts.

BACKGROUND OF THE INVENTION

*Ostertagia ostertagi* is the most economically important helminth parasite of cattle in temperate parts of the world[1]. As with all gastrointestinal nematodiases of ruminants, ostertagiasis is controlled almost entirely by the use of anthelmintic drugs combined with pasture management. Unfortunately, reports of anthelmintic resistance in bovine gastrointestinal nematodes are becoming more frequent. For example, benzimidazole (BZ) resistance was identified in cattle in New Zealand[2] and South America [3], and macrocyclic lactone (ML) resistance in New Zealand [4,5], the Americas [6,7,8] and Europe [9,10,11,12], However, as no detailed surveys have been made, the extent of the problem remains unknown and probably underestimated. It is anticipated that anthelmintic resistance in cattle nematodes including Ostertagia is likely to follow the pattern experienced with sheep, where it has reached serious proportions [13,14,15,16] although the pace at which it develops and spreads is likely to be slower.

Alternative methods for controlling bovine ostertagiasis remain an attractive prospect, in part due to the threat of drug resistance and partly because of increasing consumer sensitivity to the possibility of chemical residues in meat and milk. One such possibility for control is by vaccination. Earlier attempts to do this, using either infection with irradiated larvae[17,18] or immunisation with crude somatic or excretory/secretory products of the parasites[19,20] were not successful. More recently promising results have been obtained using fractionated native excretory/secretory products of adult parasites, with reductions in faecal egg counts of up to 80%[21,22,23,24,25].

During the last 15 years or so substantial protection against the important blood sucking ovine nematode, *Haemonchus contortus*, has been achieved by immunising sheep with various antigens isolated from the intestinal membranes of adult parasites, a topic which has been reviewed extensively[26,27,28]. When the same gut antigen approach was tested against *Ostertagia*, some protection was conferred, but not at a level deemed to have practical potential[29]. However as the same *O. ostertagi* antigens cross-protected efficiently against *Haemonchus* in sheep, it was reasoned that the relative failure may have been because adult *Ostertagia* are not blood feeders and do not ingest sufficient antibody for the gut antigen approach to be highly effective against them.

It was hypothesised that developing fourth stage (L4) *Ostertagia* might be more vulnerable to this type of vaccination than adult parasites. Firstly, since they inhabit and damage the gastric glands, L4s are likely to be continuously exposed to inflammatory exudate which is richer in host immunoglobulin than the mucous surface inhabited by adult worms, in other words, L4s in vaccinated calves would be expected to ingest a bigger dose of antibody per unit weight than adult worms. Second, because developing *Ostertagia* L4s grow very rapidly [30], increasing their mass about 20-fold in 10 days, they may be more sensitive to digestive interference than their slower metabolizing adult counterparts.

SUMMARY OF THE INVENTION

In a first aspect, the present invention provides one or more antigens from the fourth stage (L4) larvae of non-blood feeding parasitic nematodes, for raising an immune response in an animal.

Antigens from adult nematode parasites are used as vaccines for preventing, reducing or eliminating instances of animal infection. Antigens derived from adult parasitic nematodes, and in particular gut-derived antigens, can be used to raise protective host immune responses. Strategies of this type are particularly successful where the parasite is a blood-feeding nematode as they are routinely exposed to host immunoglobulin when taking blood meals. In contrast, parasites that do not feed on blood (the so-called "non-blood" feeders) are only occasionally (or in some cases never) exposed to blood and thus host circulating (humoral) antibodies to non-blood feeding parasite antigens are often ineffective.

Without wishing to be bound by theory, the inventors hypothesise that in contrast to adult non-blood feeding nematodes, certain larval stages might be more regularly exposed to host immune factors including, for example, immunoglobulin. In particular, larvae which inhabit and damage gastric glands may frequently be exposed to host inflammatory exudate which comprises a variety of host inflammatory factors including immunoglobulin.

The life cycle of a parasitic nematode comprises seven stages—an egg, four larval and two adult stages. The larval stages are commonly referred to as LI, L2, L3 and L4 (Borgsteede [34]). In non-blood feeding parasites, L4s inhabit host gastric glands, causing damage and inducing production of host inflammatory exudate. The L4s of all species which live in the true stomach (the abomasum in ruminants) do, but many species live in the intestines which obviously don't contain gastric glands. The intestines are lined by villi with glandular crypts between them. The L4s of the intestinal species reside in these crypts also causing local damage, so again are more likely than their adult counterparts to be exposed to inflammatory exudates.

As such, antigens expressed by L4 stage nematode parasites may be used to raise protective host immune responses. Hereinafter, antigens expressed by L4 stage nematode parasites will be termed "L4 antigens".

In one embodiment, the invention relates to vaccines or vaccine compositions comprising one or more L4 antigens for raising immune responses in animals. Vaccines may be used prophylactically to prevent parasitic infection. In some cases the vaccines provided by this invention may be used to reduce infection or colonisation of a host by a nematode parasite. Animals exposed to the vaccines provided by this invention, may produce antibodies which bind to (or which exhibit affinity or specificity for) L4 antigens—such antibodies may otherwise be referred to as "protective" antibodies.

The term "non-blood feeding nematode parasite" may include, for example nematode species from each of the following genera: *Ostertagia, Teladorsagia, Trichostrongylus, Nematodirus, Cooperia, Chabertia, Oesophagostomum* and *Ascaris*. In particular, the invention relates to antigens derived from species belonging to any of the abovementioned genera and in one embodiment, the invention provides vaccines/vaccine compositions comprising antigens derived from L4 stage larvae of *Ostertagia ostertagi*.

As such, the vaccines and vaccine compositions provided by this invention may be used to treat, prevent or reduce the symptoms of, diseases such as Bovine ostertagiasis.

It should be understood that the term "antigens" may relate to, for example, proteins and/or peptides (including polypeptides and short peptide chains of one or more amino acids) including for example, glycoproteins and/or glycopeptides. In addition, the term "antigen" may relate to carbohydrate molecules. In one embodiment, the present invention relates to antigens expressed by L4 stage nematode parasites, such as, for example, antigens present in the cell membranes of L4 non-blood feeding nematode parasites. Antigens of this type may otherwise be known as "integral" membrane antigens. In one embodiment, the antigens for use in raising immune responses may comprise antigens which are specifically expressed by L4 stage parasites. Antigens specific to L4 stage larvae may not be expressed by nematodes at other lifecycle stages (for example L2, L3 and adult stages). Antigens specific to L4 stage *Ostertagia ostertagi* are shown in, for example FIG. 2. In certain embodiments, the antigens for use in this invention may comprise cell membrane antigens or antigens which are expressed by L4 stage nematodes and which are exposed to the host immune system. Such antigens may include antigens expressed on the surface or in the gut of L4 nematodes. It should also be understood that the term "antigens" relate to any fragments or immunogenic/antigenic fragments of the L4 antigens described herein. One of skill will appreciate that the term "antigens" may also encompass L4 proteins, polypeptides, peptides and/or carbohydrates which are otherwise known as "immunogens".

Antigens according to this invention may be obtained, purified or extracted from cell membrane preparations using a number of techniques. For example, cells obtained from nematodes may be subjected to lysis protocols (such as those involving Triton x-100) so as to fragment the cell membrane. Subsequent centrifugation techniques may be used to remove fragmented membrane debris and ultra-centrifugation to extract membrane proteins from supernates.

Additionally, or alternatively, chromatography techniques such as, for example, those utilising affinity binding matrices, may be used to purify and/or extract membrane proteins from solution. In one embodiment, antigens for use in this invention may be purified/extracted using affinity matrices comprising concanavalin A (ConA)—a lectin which binds to certain structures present in, for example, carbohydrates, glycoproteins, and glycolipids. As such, "antigens" according to this invention may comprise proteins capable of binding ConA (ConA binding proteins) including, for example, glycoproteins proteins and/or peptides comprising a-linked mannose.

In order to extract or purify antigens, a preparation of cell membrane proteins (for example proteins preparations prepared in accordance with the procedures outlined above), may be contacted with, for example, an affinity matrix under conditions which permit binding between the affinity matrix and antigens, for example (glycol) proteins/peptides, present in the membrane preparation. Antigens bound to an affinity matrix may be released or separated therefrom with the use of a suitable elution solution/buffer. In the case of an affinity matrix comprising ConA, antigens bound thereto may be separated or released by applying carbohydrate solutions. Additionally, material eluted from, for example, ConA affinity matrices, may be further subjected to procedures designed to remove carbohydrate. For example, material eluted from ConA affinity matrices may be contacted with Sephadex G-25 to remove carbohydrate. Antigen preparations of this type may be termed crude antigen preparations. Crude preparations of this type may be stored for prolonged periods of time at −20° C. or, more preferably at −80° C.

Crude antigen preparations of the type described above may be further processed in order to yield antigen fractions comprising fewer and more highly purified (or cleaner)/concentrated antigens. By way of example, techniques such as, for example, anion exchange and/or gel filtration may be used to prepare one or more fractions of the crude antigen preparations described above.

In one embodiment, the method of obtaining L4 antigens for use in raising animal immune responses is that shown in FIG. 1.

The various cell membrane protein preparations and fractions thereof described herein may otherwise be referred to as "antigen pools". Accordingly, the vaccines and vaccine compositions provided by this invention may comprise one or more of the antigen pools described herein. By way of example, vaccines for use in raising immune responses to the nematode parasite *Ostertagia ostertagi* may comprise one or more antigen pool(s) selected from the group consisting of (i) a pool comprising ConA binding proteins from a cell membrane preparation and (ii) fractions of ConA binding protein mixtures obtained by one or more rounds of anion exchange and/or gel filtration. In one embodiment, the vaccine or vaccine provided by this invention comprises one or more of the ConA, pool 1, pool 2 and/or pool 3 fractions described in the detailed description section (see part entitled "Preparation of Immunogens") and in FIGS. 1 and 5. In one embodiment, the vaccine or vaccine composition provided by this invention comprises the antigen pool used in Trial 1, Trial 2, Trial 3 and/or Trial 4 as shown in Table 5 and FIG. 1 and described in the detailed description section.

In one embodiment, the antigens for use in this invention are derived from the L4 stage of the non-blood feeding bovine parasite, *Ostertagia ostertagi*. As such, the invention may provide one or more antigens from a fourth stage larvae of *Ostertagia ostertagi*, for raising an immune response in a bovine. Specifically, the invention may relate to ConA binding proteins or membrane (glyco)proteins and/or peptides from L4 stage *Ostertagia ostertagi*, for raising an immune response in a bovine.

In one embodiment, the bovine is a neonatal or juvenile bovine—otherwise known as a calf.

Antigens for use in raising animal immune responses may be obtained from whole or fragmented parasites harvested from donor animals. Donor animals may be naturally infected animals or animals which have been deliberately (or experimentally) infected with a particular parasite. For example, experimentally infected animals may be administered a dose of L3 stage parasites sometime before L4 stage parasites are harvested. One of skill will appreciate that the time between administration of an L3 dose and harvesting L4 parasites will vary depending, on for example, the life cycle of the parasite to be harvested. In the case of the non-blood feeding parasite, *Ostertagia ostertagi*, L3 stage larvae may be administered approximately 7 days before L4 larvae are harvested.

In addition to providing proteins or peptide antigens from non-blood feeding L4 nematode parasites, the present invention relates to nucleic acid molecules encoding the same or fragments (preferably antigentic or immunogenic fragments)

thereof. The nucleic acid may be DNA, RNA or a combination thereof and can include any combination of naturally occurring, chemically or enzymatically modified nucleotides. Furthermore, the nucleic acid may be double or single stranded. Within the scope of this invention are nucleic acid sequences that are substantially complementary to any of the L4 antigen sequences described herein.

It should be understood that the term "substantially complementary" encompasses those nucleic acid molecules exhibiting a degree of sequence identity/homology with any of the L4 antigen nucleic acid sequences described herein—such as, for example, those presented in Tables 1 and 3 below. A sequence having a level of identity with a L4 antigen nucleic acid sequence of this invention may exhibit at least 40%, 50%, 60%, 65%, 70%, 75%, 80%, 85%, 90%, 95%, 96%, 97%, 98% or 99% identity with the full length L4 antigen nucleic acid sequence or any portion or fragment thereof. One of skill will appreciate that a level of sequence identity may be determined by comparing aligned nucleic acid sequences over a predetermined length so as to determine the number of positions at which an identical nucleic acid base occurs in both sequences to yield the number of matched positions, dividing the number of matched positions by the total number of nucleic acid bases in the length compared and multiplying the result by 100 to yield the percentage of sequence identity.

The nucleic acid molecules provided by this invention may take the form of nucleic acid constructs or vectors such as, for example a cloning or expression cassettes/vectors. Vectors provided by this invention may be capable of directing the expression of nucleic acid sequences encoding L4 stage antigens in, for example, bacterial, fungal, mammalian and/or insect cells.

Accordingly, a second aspect of this invention provides a vector, preferably an expression vector, comprising a nucleic acid sequence encoding any of the L4 antigens described herein (including, fragments, variants, analogues or derivatives thereof). Expression vectors suitable for use in this aspect of the invention may further comprise one or more promoter sequences capable of directing expression in prokaryotic or eukaryotic cells such as, for example, mammalian, fungal, bacterial, plant and/or insect cells.

A vector provided by this invention may be circular or linear, single stranded or double stranded and can include DNA, RNA or a combination or modification thereof. Furthermore, vectors of this invention may be, for example, plasmids, cosmids or viral vectors (for example retroviral or bacteriophage vectors). Vectors provided by this invention may further comprise selection or marker elements, for example antibiotic resistance genes and/or optically detectable tags. A large number of suitable vectors are known and further information may be obtained from Pouwels et al. Cloning Vectors: a Laboratory Manual (1985 and supplements), Elsevier, N.Y.; and Rodriquez, et al. (eds.) Vectors: a Survey of Molecular Cloning Vectors and their Uses, Buttersworth, Boston, Mass (1988)—both of which are incorporated herein by reference.

In addition to techniques in which L4 antigens are extracted or purified from membrane preparations from harvested parasitic organisms, antigens for use may be obtained using recombinant technology. In one embodiment, an expression vector comprising one or more nucleic acid sequences encoding L4 antigens may be used to produce recombinant L4 antigens. Accordingly, in a further aspect, the present invention provides host cells transfected or transformed with a vector as described herein. Eukaryotic or prokaryotic cells, such as, for example, plant, insect, mammalian, fungal and/or bacterial cells, may be transfected with one or more of the vectors described herein. One of skill in this field will be familiar with the techniques used to introduce heterologous or foreign nucleic acid sequences, such as expression vectors, into cells and these may include, for example, heatshock treatment, use of one or more chemicals (such as calcium phosphate) to induce transformation/transfection, the use of viral carriers, microinjection and/or techniques such as electroporation. Further information regarding transformation/transfection techniques may be found in Current Protocols in Molecular Biology, Ausuble, F.M., ed., John Wiley & Sons, N.Y. (1989) which is incorporated herein by reference.

Another aspect of this invention relates to a host cell transformed with any one the nucleic acid constructs described herein. Suitable host cells include prokaryotic and/or eukaryotic cells. For example, bacterial, fungal, mammalian, plant and/or insect cells are all capable of being transformed with any of the nucleic acid constructs described herein. A host cell transformed with a nucleic acid construct provided by this invention may be referred to as a "transformant". Where the vector comprises a selection/marker element, transformants may be selected by application of antibiotics to culture media.

In view of the above, the present invention further provides a process for the production of a recombinant L4 protein or peptide for use in raising an immune response in an animal, said method comprising the step of (a) transforming a host cell with a nucleic acid sequence according to this invention or transfecting a host cell with a nucleic acid construct of the invention; (b) culturing the cells obtained in (a) under conditions in which expression of the protein takes place; and (c) isolating the expressed recombinant protein or peptide from the cell culture or/and the culture supernatant.

Recombinant proteins/peptides produced according to the method described above may be partially purified from the host cell before being used as a vaccine. Where the polypeptide is secreted from the host cell, the cells may be separated from the media by centrifugation, the cells being pelleted and the media being the supernatant. In such a situation, the supernatant, which contains the secreted polypeptide, may be used directly as a vaccine, or in a vaccine composition. Alternatively, the polypeptide may be partially purified from this supernatant, for example using affinity chromatography.

In one embodiment, purified L4 antigens/recombinant antigens may be admixed with another component, such as another polypeptide and/or an adjuvant, diluent or excipient. Vaccines or vaccine compositions provided by this invention may contain bacterial antigens used to control other diseases. For example, the vaccine or vaccine composition may be included within a multivalent vaccine which includes antigens against other bovine diseases.

In a still further aspect, the present invention provides a bovine population treated or immunised with a vaccine or composition described herein. In one embodiment, the bovine population is a neonatal or juvenile bovine (i.e. calf) population.

One of skill will appreciate that the vaccines described in this invention may take the form of subunit-type vaccines where by one or more proteinaceous L4 antigens are used to inoculate an animal. Additionally or alternatively, the vaccine may comprise a nucleic acid molecule (known as a DNA vaccine) encoding one or more L4 antigens to be expressed by the cells of an animal to be vaccinated.

Suitable antigens for raising bovine immune responses to the non-blood feeding parasite *Ostertagia ostertagi* may include, for example, one or more antigens encoded by cDNA sequences having or comprising the following cDNA sequences (Tables 1 and 3):

TABLE 1

*O. ostertagi* L4 cDNA library screen (with antiserum from protected calves immunised with pool 3 fraction from Trial 2 - see FIG. 1)

Clone 1.1 (SEQ ID NO: 1)
CTATCNTATTCATCGCGCGCANCCCGGGTATAACGAGGACGTCATGTCCGGCTTTGTNCCGCTTTCTTC
ACCTTCTTCGTAGCGCTTTACGTCAGGAATGTGCCAACCATCGAAGACTTCGCTGTTCGATCGATCCCA
AAGGAAGCTCAGGAGCTGACTGGTGAAGCGCTAGCGGAGATATGTGAACAGGCAGCAGCCGTTTCAAGG
CCATGTATTCGCCAAATGTGGAGCGTCGTATGGCAAGTTTGATGAACACACTGGAATACCTCGAGAAAA
GCAAGCGTCAATTGAAAATGAAAATGCCAGAAAAAGCCATAAACAACGACACGCTCCCTGAAAGTTTCG
ACAGTCGGGAGCAATGGAAGGACTGCCCCTCTCTACAGTACGTTCGCGATCAGCCACACTGTGGCTCCT
GTTGGGCTGTCTCGGCTGCGAGCGCTATGTCCGATCGACTCCGTATACAGACGAACGGCAAGAATAAGG
TGATTCTCTCGGACACTGACATCCTTGCATGTTGTGGAGAATTTTGTGGACTTGGATGTGAAGGAGGAT
ACCCCTCACAAGCCTGGGAATTTGCCCAAAGGAATGGCCGTGTGCAGTGGAGGATGGTATGGTGAAAAG
GGTGTGTGTAAACCATATCCTCTCCATCCATGTGGAAAGCACGAAAATCAGACTTTCTATGGCGAATGT
CCAGACCACACGTACAGAACTCCGGCGTGCAAGAAGTACTGCCAATATGGATACGACAAGCGCTATGAT
AATGATAAAGTCTA Clone 2.1 (SEQ ID NO: 2)
CATCGGCCNTAGGCGGGGGTATGAAGAATATCGACAAAGACGATACTTGCGTTATGTATTCTGTGCTGG
CGTATGACGCAACCAGTGAAATTCACGAAACTATTGTGATGGTTCTCATAAAGAATGAGACGGGAAAAG
TCAGATCTCACTACTTCAAGTATCAGGTGATAACTGATAAGACAACAAAGAAACAAAGCACTTGGATTG
ACGACATGGACGCGCTTAATTTCATGTTAACGATAAGAAAGTGTAAGCTCGTCCCTTCTAGAGGTTAAA
ATCCGTCTTGAATGAATGGACATGGAAATAAATTTTCGCAGCTGTAAGAAGG Clone 3.1 (SEQ ID NO: 3)
ACCGGGAAATCGGCATCCGCGGGTTTAAGCTTTACACCGATTCCATCTATTGTGTCGCTGTTTGAGATT
ATTCCGAAAAATGTGCATGAGGAGCAGAACAGAAAAGAGTATCTGGAGATGGTTACCGAGAAAATGGAG
TGCTTGCTAGAAGATCTTCTTCACTGTCATGATCGAAATGTGAAAAGTCGTGGAAAGAAATCAGCCGTC
TAGGTTTTAATACCAAACTTGCTTCCCAGGGAGGTCTTCCAGAAAATGCCCAACTTTCTCGAAAAAGTT
TTTTTTTGCATGATGTANAGGTACATGCATGGAAGCCAGAATTGTGGCTCATCTTTCCTGAGCGGCCCT
GTNNAATACC Clone 4.1 (SEQ ID NO: 4)
TACAAATCGGAAGTGACCCCAGTNANTACAATGTTCTAGGCAAGCGATCATCGTCCAACTCCTCAAACA
GCCCCAGCCAGGATCCACTACCACCGAGAACTCCTCTTCCGCTTGATTTCTTGGATATTCCGGTAAAGCC
CCATGGGTATTGAANTGGACTATACAACCTGCTCACATATATGTCAACACTGTTAGAGTCTGCTATGAT
CGGTCTACTGAGGATCTATTGCCCAAAGTTATGTAATCTGTGCTATCGTCGTCTTTACATCAATTTTTA
TTTGATCACTGTATGATATGGGAGGGATGTTTGAATAGTAGAGAAAGTGTAGTAGTATAAATAAATACC
TCATACATACACAG Clone 6.1 (SEQ ID NO: 5)
GCCGGGATCTGGCACTTACGGCCGGGGTNAGGAGGAATTGTTAAAATCCTTCAAAACAAGCGAGGAGAG
CCACTAGATGATGATGAAATCAAGGCCATGTACAAGGCTAAGCCACCAATCGAGAACGGTGAAGTCGAC
TACAAGGCATTCGCACATCTCATCACTACCGGAGCTCAAGACGAACTCACTGCCGCATAAACGTTCCTT
CAATCATTTGTGTGTGTCTTTGATCGAATCGGATGAAAGAGAAATGGCCAG Clone 7.1 (SEQ ID NO: 6)
GCGGGAATTTGGGNACTGANGGCGGGATAGCTAGCTNGCAACAACATGTGGATCAAAACCGTCACCCCT
GAAGGAGAGGTTACCAAGTGTAGACTGGACAGATGTTTACCAGCAACGCCCGAAATGCTGTCGGTATTT
CTGAACCAGGATACCTTACACATGAGGCGGTTCAGTGGTCAGAAACACAGGGACATTGGTACTTCCTTC
CTAGAAAGGAGTCAAAGACTGTCTACGTAGAAGAAGAGGATGAGACGAAAGGCACGGATCTCCTGATTA
CTGGAAATCCGGACCTTGACCAATTCGAAGTCAAGAGGATAGGAATACTGCGACCCGAACGCGGATATT
CGGCATTCGATTTTATTCCTGGTACCGACGACAAGATCATCGTTGCCTTGAAGTCCAAAGAAGTGACCG
ACGAGCCAGTCGAAACCTACATCACAGTATTTACCACTGACGGTCAACTCCTACTTGATGATCAGAAAC
TCGACGGCAACTACAAATTTGAGGGACTCTACTTCATTTGAATTTTCCCTC
GTCATGAAAAGTGTCAAATGTTGGCTAACAATAAATAATTTTATAGC Clone 8.1 (SEQ ID NO: 7)
TTAAACAGCTTCTACTACTGAAGCTTCGACCACTACTGTTCCGTATGAGGAGGACAACCAGATATGCCC
ACATCACCGTGGCATGAAAGACACATTAAGAATAAGGGCATTAGTGGCTCACAATTATCGGAGGTCAAG
GCTTGCTATGGGGCTTGTCAGAAACAGGAGGAGGAAGAACACTGCCAACGGCGTCCAACATGGATCTTT
GTCCTCAAAAAGAACATTTTCCACGACGACAGCGCACCACATCCACAGAGCAGTGATACCTCCTATCAC
TGACAATTATTGAATACAATTGCACAAGTGAAGCATATGCCATACAAAATGCGGTGAGGTGCTCTGTAG
TTCCACCTTCGACAATGCCTTCTTTTGTCCAAGAAAACCGCCATATGGTTTTAAAGTCTTTAGCAAACA
CTAAGGAGAAAGCGCTTATAGTTCCGACTTCACGGCCGATCACGTCTGGTGAAATGCACTTTCACAATG
CTATTGATTATGATATCATACATTTCAACTTATTGTGCTCGAAAAGTGACAGTTTCTGAGGGGCGAGAT
GAGCTCAACTGCATAGCCACTAGTGCATCTTGCACAGCGGAAACACCACGAGTTATTCCTTCTGCCTGG
CTACCGTACCAATGTTGCAT Clone 8.2 (SEQ ID NO: 8)
GCCGGGAATTCGGNACCGCGGNTTTGCGAAGTGCTCCTGGAAGTTGCTGGTCGTGATGCCACTGAGGCC
TTTGAGGACGTCGGTCATTCTACAGATGCTCGTGAGAATGAGGGAGCAATATCTTGTCGGAGATATTGC
TGACGAGGAGAAGCAGCAATATTCGTATGATAAGAAGGAATGGGTGACCAGCCCCAGCGATAATAAACA
AAGGGACTCGAACCCGTGGGCAGCATTGGACAAATACATCTATCCTGCTCTGTTCGCCATCGTCTTCGC
CCTTATTTACTACCTTATCACAAACTAGATTTCTGCTTTTTGAAGTAGATTTGGGTTTTATTTCTTCAT
GTTCCGATTTGTTGGATTGTCACTTAAATGTTTCACATTTGCATGTACCGGTATATCAGTTTTTATCCG
TTGCACGATATATTATAGTTAAGGTTTGTGGTCTAACATTGTTAGGAATAAAAGT TABLE 1-continued

*O. ostertagi* L4 cDNA library screen (with antiserum from protected calves immunised with pool 3 fraction from Trial 2 - see FIG. 1)

Clone 9.1 (SEQ ID NO: 9)
CGATCGGCATTACGGCGGGTATATGGAACGAGGACTTGACCCCAAGCTGTGGAAGGACTTCTGGGATAT
CTTCGAGAAGTTCCTGGAGAACCGCAAGCCACTAACTGCTGACCAGAAGGCTGCGCTTGATGCGATGGG
CACAAGATTCAACGATGAAGCTCAGGAAGCGAACTGGCCGTCCTTGGACTTCCACACACATAAGAAACT
CTCTTGGGAAATGCCTAGGTCTTGATGCGTCAGTGAATAAAGTATG Clone 10.2 (SEQ ID NO: 10)
GCCGGGAATCGGCACTACGGCCGGGTTAGCGATGAAGAAAATCGAAGATCACAACACGCTTGTCTTCAT
CGTTGATGTGCGAGCGAACAAGCACCAAATTCGGGCAGCTGTGAAGAAGTTGTACAAGTATTGAGGTGC
AAAAGATTAACACACTTATCACTCCCCGTTATGGAGAAAAAGGCCTACATTCGCGTGTGACGACGGATT
ATGATGCCTTAGATTGCGCCAATAAGATCGGAATCATATGAATTCTTGTTGTTTTGTTATGAATGGTTG
ATAAATTTGGGTTAATTGAACAAGG Clone 11.2 (SEQ ID NO: 11)
GGCCGGGGGTATCGGAAGGAAAGCATATTCAGACAAAAGCACGAGTCTAGCCCAATCAGACACTTCACT
CTGATGGCATGGGCAACCACCGAATACATTGGATGCGCTGTGTCGCTCGCTCGTGCCCCAGGCGAGTGG
TATATTGTATGTCACTACAGAAACGGAGGTAATACTTGTAAACGAACACGTTTACATGCCAGGGTCCCA
CATGTTCAGACTGATCCCACAAGCTACCACTGTGGCGCGGACAAGTAGTAGCACGAAATCTTAAACAGC
CTCCATGCTTATATANAGCTAATAAAAGGAAAATAAAGTTATAACGAGC Clone 12.2 (SEQ ID NO: 12)
GCCGGGAATTGGCATTACNGCGGGTTGGGATTAGTTTGTGATGAAGTTTCATAACAGTGTCTATGTTTA
TGATAAGTTGATGATGAGTGCTGTGTTTTTTTAATATTTTTGGTGTTAATTTGACTTTTTTTCCTTT
GCATTTTGCTGGTTTGCACGGTTTTCCTCGTAAGTATATAGATTATCCGGATGTTTATTCTGTGTGAAA
TGTTATATCTTCGTATGGTTCAATAGTAAGTGTTTTTGCTTTGTTTTGGTTTTTGTATGTGTTGTTAG
AATCTTTTTTAGTTATCGCTTAGTGTTGGTTGATAATTTTGGTAAACAGCAGACCCGAGTATAGTTAT
AGCAGTTATGTTTTGGGTCACAGTTATCAGAGTGATATTTATTTTAGAAGTGCTGTGTTAAAAAATT Clone 14.1 (SEQ ID NO: 13)
CCGGGATCATCAATGAGCAATCCAGACGTTCTCAACTCGATCACTTCCAATCGCGTAAAGCAAGTGGTC
AATGCTGGTGCGTCAGTGGCGCGTTGCATCAAAATGTGTTTCATCGAGAAAGAATAAAGACGGGTTTTG
CTTCGACAAGAAAGGTTGTGAACCGAACATTGCGGACCGAAACGCAAAGCTTGCGATCAAACAGTGTCC
ACGTTTGATTAATTGGAAGAAGGAGATCAGCGACTTGTGCATGTGTTCCAGTCAAGCAGGTGTTCATGG
AATTTCGGACTACTGCGGAATGCTGAGCATAATGGGATAGAAGGAACATCTTGGTGATCATTTCGCGAT
TGTTGCATGATTTGTACATTTATTGTATTTATACGACAGCGTAATCATCAAGAAACTAACTTCACTCGA
TTTTCCTGATAAAATTTAACGAC Clone 14.2 (SEQ ID NO: 14)
TTCAGCGTCGTGCTTTCGTTCGCGTCATTGGTGGCAGCCACTTGGGTACTCTTCAGCGACTATGTCCTT
CTCACCGGTGATCATCCAGTGTGGCCTGGAGTAGCACTTTTCCTTACCAA
TTTCATAATTTTTGCCTCATCTTGTGTTTACAAATTTGGCCGTACCGAAGAAATGTGGGGATAAATGTA
ATATAATTTCAGTTGGTCCCCTATTTATTCCAGGATTTCGCTTTTTCTTTCCATCGGAGGCAGACACAG
GCCATAATTTCTACTTACTTTTGTGAGGACATGTTCATACTTGTATTGGACTAAAGTATATTACG Clone 16.1 (SEQ ID NO: 15)
GATCGATTCGATTCCGATTCCGATTCCGATTCCGATTCCGATTCCGATTCCGATTCCGATTCCGATTCG
ATTCGATTCGATCGATCGATCGATCGATCGATCGATCATCATC Clone 17.1 (SEQ ID NO: 16)
CATCGATCCGATCCGATCCGATCCGATCCGATCCGATCCGATCCGATCGATCGATCGATCGATC
GTCGTCGTCTCTCCCC Clone 18.1 (SEQ ID NO: 17)
GATCGGATCGATCGGATCGGATCGATCGATCGATCGATCGATCGATCGACGTCGCGACGCGCGCGCG
GGGCG Clone 18.2 (SEQ ID NO: 18)
ATCAGCGACTGGGGCGAAGACGGTTACTTCCGTATCGTACGAGGAGTGGACAACTGCGGTTTCCAGTCG
GACGTCATCGCTGGGGACTTCCTTTGACGGTGTGATCGATCACCATAAATCTCATATGCATGAAATAAA
TTGT Clone 19.1 (SEQ ID NO: 19)
GATCGATTCCGATTCGATTCGGATTTCGGATTCGATTCGGATTCGGATTCGGATTGATTGGATTGAATT
GAATTCGAATTGAATTTGAATTTGAATTTGAATTTGAATTTCGAATTTGAAATTTGAAATTGAAAAAT
TGAAAAA Clone 20.1 (SEQ ID NO: 20)
TCGATCCGATCCGATCCGATCCGATCCGATCGATCGTCTCTCTCTCCCCC Clone 21.1 (SEQ ID NO: 21)
GATCCGATCCGATCCGATCCGATCCGATCCGATCCGATTCCGATCCGATTCCGAATTCCCGATTCCCGA
TTCCCGAATTCCCGATTCCGGATTCCGGATTCCGAATTCCGAATTCCGAATTCCGAATTCCCGAATTCCC
GAATTCCCGAATTTCCCCGAAA TABLE 1-continued O. ostertagi L4 cDNA library screen (with antiserum from protected calves immunised with pool 3 fraction from Trial 2 - see FIG. 1)

Clone 21.2 (SEQ ID NO: 22)
CTCACGGACGGGAAGCCGCAGCACATTTCACTTCACCTCATCGATCAGCGTTGTACAGAATACTCTCAT
CACCACTCAGAGTCTTTAATAAAACAATATTTC Clone 22.1 (SEQ ID NO: 23)
CATCGATCCGATCCGATCCGATCCGATCCGATCCGATCCGATCCGATCCGATCCGATCCGATCCGATCC
GATCGATCGATCGATCGATCGTCGTCGTCGTCG Clone 22.2 (SEQ ID NO: 24)
AAATCATGTTATACTTCAGCAGAGCCGCAAACGATGAACGAGGATCACGCCGGCAGTATGGCTCGGATA
GGATTGGAGCGTTATAGGAAAGATGGATGGTGTAATAAATACTATTACTCATGTCGTGCGATACTTGGC
TTACCGCCAAAGGAACGAGCTCCTATCGGACCTAATGGCAAACGTCTGTGCCGCAAAAAACCGCTGTGA
TTCGTCCCCTATTTGCGTATTTGTAGTGAAATACGAGCTGATTTTCGCTCCATAATGACTAGTTCGTTG
AATATTTGTCATCGCTTTGCAGAATTTCACAGAATTTTTGCTTGCGCAGAAATAAATATTCCGCTCC Clone 23.1 (SEQ ID NO: 25)
ATCCGATCCGATTCCGATCCGATCCGATCCGATCCGATCCGATCCGATCCGATCCGATCCGTCGTCGAT
CGTCGTCGTCGTCGTCGTCGATCGATCGATCGA Clone 23.2 (SEQ ID NO: 26)
AACCAGGGCGCTCTTGGCCTACGGACTGTTTGCAAGGCGTTCCGACAGTTCAAAGGATGC
ATGGGAAAGGGATACTCGGCTTGCATAAACGCTGGTCACTTTGTTACCGCTTCAGTTCCG
ATTTTCGAGTCCTATCAGTTTGTCAGCATCTTCAATCAAATGCATTATGTTTGTAGAGGA
GGATTTCAGATTTATATGAGTAATGATGACTGCATGTCAAAAGCTTGGAGTGGGAGCACT
GGAGATCAGCTGAACGCCTGTCGGTACAAGTTTGAAAAGAGTAGCGATGATGTCAGCGCAGAA
GACGCTCAGTCCGTGAAGTACTTGGCCAACACTTACCTGACGTGTTTCGAAGACCAATTC
AAGGAGGCTTGTGGTCTAAACTCCCGCGACACGCAATTCTGGGGTTGTGAATACGCGCGC
GTCAATGTTTTCACTCGCTTTCCTCAGACTGACGTGGACTGTGTCTTACCCTACGCAGGC
GGCATGATTGGATGAGAGCGAAGCCAATACTATTGTAAATGTTACTGTGTCAAGATATTG
TGATAAGATTTGAAATAT Clone 24.1 (SEQ ID NO: 27)
CGATCGATCCGATCCGATTCCGATCCGATCCGATCCGATCCGATCCGATCCGATCCGATCCGATCCGAT
CGATCGATCGATCGTCGTCGTCGCGCC Clone 25.1 (SEQ ID NO: 28)
CATCGATCGATCCGATCCGATCCGATCCGATCCGATCCGATCCGATCCGATCCGATCGATCGATCGATC
GATCGTCGTCGTCGTCCCC Clone 26.1 (SEQ ID NO: 29)
GATCCGATTCCGATTCCGATTCCGATTCCGATTCCGATCCGATTCCGATTCCGATTCGATTCCGATTCG
ATTCGATTCGATTCCGATTCCGATTCCGATCCGATCCGATCCGATCCGGAATCCGGAATCCGGAATCCG
GAA Clone 27.1 (SEQ ID NO: 30)
GATCCGATTCCGGATTCCGGATTCCGGATTCCGGATTCCGGATTCCGATCCGGATCCGGATCCGGATCC
GATCCGATCCGATCCGATCCGATCCGATCCGATCCGATCCCGATCCGGATCCCGGATCCCGGATCCC
GGATCCCGGA Clone 28.1 (SEQ ID NO: 31)
GATCGATCCGATCCGATCCGATCCGATCCGATCGATCCGATCCGATCCATCCGATCGATCCGTCCGATC
GATCGATCGATCGAATCGATCGATCGAATCGATCGATCGA Clone 29.1 (SEQ ID NO: 32)
CGATCGATCCGATCCGATCCGATTCCGATCCGATCCGATCCGATCCGATCCGATCCGATCCGATCCGAT
CCGATCGATCGATCGATCGATCGATCGATCGTCGATCG Clone 29.2 (SEQ ID NO: 33)
GTGTAAGTCTGGTGGTAAATCATGTTATACTTCAGCAGAGCCGCAAACGATGAACGAGGATCACGCCGG
CAGTATGGCTCGGATAGGATTGGAGCGTTATAGGAAAGATGGATGGTGTAATAAATACTATTACTCATG
TCGTGCGATACTTGGCTTACCGCCAAAGGAACGAGCTCCTATCGGACCTAATGGCAAACGTCTGTGCCG
CAAAAAACCGCTGTGATTCGTCCCCTATTTGCGTATTTGTAGTGAAATACGAGCTGATTTTCGCTCCAT
AATGACTAGTTCGTTGAATATTTGTCATCGCTTTGCAGAATTTCACAGAATTTTTGCTTGCGCAGAAAT
AAATATTCCGCTCCG Clone 30.1 (SEQ ID NO: 34)
CGATCGATCCGATCCGATCCGATCCGATCCGATTCCGATCCGATCCGATCCGATCCGATCCGATCCGAT
CGATCCGATCGATCGATCGATCGTCGATCGTCGTCG Clone 30.2 (SEQ ID NO: 35)
GCCGCAAACGATGAACGAGGATCACGCCGGCAGTATGGCTCGGATAGGATTGGAGCGTTATAGGAAAGA
TGGATGGTGTAATAAATACTATTACTCATGTCGTGCGATACTTGGCTTACCGCCAAAGGAACGAGCTCC
TATCGGACCTAATGGCAAACGTCTGTGCCGCAAAAAACCGCTGTGATTCGTCCCCTATTTGCGTATTTG
TAGTGAAATACGAGCTGATTTTCGCTCCATAATGACTAGTTCGTTGAATATTTGTCATCGCTTTGCAGA
ATTTCACAGAATTTTTGCTTGCGCAGAAATAAATATTCCGCTCC TABLE 1-continued

*O. ostertagi* L4 cDNA library screen (with antiserum from protected calves immunised with pool 3 fraction from Trial 2 - see FIG. 1)

Clone 31.1 (SEQ ID NO: 36)
GATCGATTCCGATTCCGATTCCGATTCGATTCGATTCGATTCGATTCGTTCGTTCGATTCGAT
TCGATGATTGATTGATTGATGATGATTGATTGATTGATTGA Clone 31.2 (SEQ ID NO: 37)
TTTGTGTAAAGATGTTATTTAATAGTTAGAATTATATAGGTAGCGAATAACTGTGAACTG
TGTTAAAGTTAATTATTGATGACTCGGTGTTTCGGTGGTATTTATTTGTTTAGAAGTTTA
TTTATCAAAAATTTGTTATAATTAGATTTTGTTTGTTGATTTGTGGGAATTAAAATTAAT
AACACTGTGCTGTGTGTTTTTTGATATTTATTGTAAATGTTTTGTAACTTTGTGCAGGTG
GGTTTTGGTGGTAAGTCAG Clone 32.1 (SEQ ID NO: 38)
CGATCGATCGATCCGATCCGATCCGATCCGATCCGATCCGATCCGATCCGATCCGATCCGATCG
ATCGATCGATCGATCGTCTCGCCTCG Clone 32.2 (SEQ ID NO: 39)
GATGTTGAGTGTAAGTCTGGTGGTAAATCATGTTATACTTCAGCAGAGCCGCAAACGATG
AACGAGGATCACGCCGGCAGTATGGCTCGGATAGGATTGGAGCGTTATAGGAAAGATGGATGGTGTAAT
AAATACTATTACTCATGTCGTGCGATACTTGGCTTACCGCCAAAGGAACGAGCTCCTATCGGACCTAAT
GGCAAACGTCTGTGCCGCAAAAAACCGCTGTGATTCGTCCCTATTTGCGTATTTGTAGTGAAATACGA
GCTGATTTTCGCTCCATAATGACTAGTTCGTTGAATATTTGTCATCGCTTTGCAGAATTTCACAGAATT
TTTGCTTGCGCAGAAATAAATATTCCGCTCCG Clone 33.1 (SEQ ID NO: 40)
GATCGATCCGATCCGATCCGATCCGATCCGATCCGATCCGATCCGATCGATCGATCCGA
TCGATCGATCGTCGTCGTCGTCGTCGTCGATCGA Clone 34.1 (SEQ ID NO: 41)
GGCGATCGATCGATCGATCGATCGATCGATCGATCGATCGATCGTCGTCGACGCGTCGCGACGACGACG
ACGCGC Clone 35.1 (SEQ ID NO: 42)
GATCGATTCCGGATCCGGATCCGATCGATCGATCGTCGTCGCGCGACGACGCGCCCCCCCC Clone 35.2 (SEQ ID NO: 43)
ACCTCCCCTTCTGCTCAAAAGCGAAGCCGTCAACATTCAGAGCTGCTGATTGAACTCTCG
TTCTCTTCTGCAAAGCATCTTACAGTGTATTTTCATACGCACCTACTGCGTAATTCTTCC
TTCTTCTTATGTAAACTTGGTACCTATATAATCCATTCTCTTTCCCCGAATAAATATTAC Clone 36.1 (SEQ ID NO: 44)
GTCGATCGATCGATCGATCGTCGTCGTCGTCGTCGTCGTCGTCGTCTCTCTCTCTCTCTC Clone 36.2 (SEQ ID NO: 45)
TTATATCCATAATCTGTTTATTCGTGTCTGTGCCCCTGTGAGTTCTTTTTTTGAGGTGAA
ACATCTGGATTTGATCTGTCGTGTTCCTTCTATTGATGCGTTAACGCGACACAGAAATGA
AATGTCACG Clone 37.1 (SEQ ID NO: 46)
GGCGTCGTCGTCGTCGTCGTCGTCGTCTCTCTCTCTCTCTCTCCCCC Clone 37.2 (SEQ ID NO: 47)
CATTACGGCCGGGGAGCTGTGGGCGCTTTTTTGGACACTCATTCTTGAGTGCCATATCCATCGAAATT
CACTATGCCCAGACCAATTGTAGCCACCCATCGTTTGTTAGTCGGTGCGACGGTGGCTCTTGAAACCAA
ACGTTGTTTCTGAGCTAGATGCCTGCATGCGATGTACGTTCGTCTTACGGATGCCCATCATCTCTCTGT
ATAAAATTCCATGATGCT Clone 38.1 (SEQ ID NO: 48)
GTCGATCGATCGATCGATCGATCGATCGATCGTCGATCGATCGATCGATCGATCGATCGATCGATCGAT
CGTCGTCGTCGATCGATCGTCG Clone 38.2 (SEQ ID NO: 49)
CGGCATTACGGCCGGGGTGGAAGAAGGGCGTGGTTCTCGACCTAACCATTTCAAGAAAGGGTCCGGCTC
CGTAGTGCGCAAGGCCTTGCAGACCCTCGAAGCTATCAAATGGGTTGAGAAACATGCAGATGGCAAGGG
TCGAGTCTTGTCAAAGCAGGGAAGAAAGGATTTGGATCGAATTGCAACCGACTTCGTCAGCACGTTAA
ACCGATTGAGCTCTAAGTTGTTTTCAGTGCATGTTGTTTTGTTATAAATGTTGCAATG Clone 39.1 (SEQ ID NO: 50)
GGATCCGGGATTCCCGGGATTCCGGATTCCGGATTCCGGATTCCGGATTCCGGATTCGATTCG
ATTTCGATTCGATTCGATTCGATTCGATTCATTCATTCGTTCTTCATTCATTCGATTCGTTG Clone 39.2 (SEQ ID NO: 51)
ATTACGGCCGGGGCGTGTAGTCATTGACGTGTATCTTTTGAAACTTAACTTGTTATCTTT
TGCTACATTGTTGTGCTGAATAATAAAGTAGTTTGAATTTTG Clone 42.1 (SEQ ID NO: 52)
TCGGCATTACGGCCGGGGTCCGTCGTCGACTCCAAAGCTACTAAGACTGGTCCAACCCTTCATGGAATT
ATTGGTCGCAAATCCGGAACCGTTGATGGTTTTGATTACTCTGCTGCCAATAAAAACAAGGGAGTGGTA

TABLE 1-continued

*O. ostertagi* L4 cDNA library screen (with antiserum from protected calves immunised with pool 3 fraction from Trial 2 - see FIG. 1)

TGGACGCGAGAGACATTGTTTGAATACCTTCTGAACCCTAAGAAGTACATCCCTGGAACAAAGATGGTC
TTCGCTGGATTGAAGAAAGTCGATGAACGAGCTGATCTCATAAAATACATTGAAGTTGAATCGGCGAAA
CCTGTCAGTTAACCATAATGATTATTTAATTTGAGATATGTTCGTATAGGTTTTAGTGAAAGTTTTATA
AAGATCTTGATATTTGCGCTGTTGCAGAAACGTTAGCGCTCGACTTAACCATTCGTTCATTATCTCATC
TCAGCT
GCCCTTTACCCGTATTGTAATACCAATTTTATAGTAGCAATGTCTCATTGAAGTGAATCT
TCCACCGCG

Clone 45.1 (SEQ ID NO: 53)
GTGCTCGGGAGCGCGCCATTGTGCTCGGGAAGCAGCGCCATTGTGCTCGCGCAAATGCATCGTCATGTG
GGCCCGAAAAAGGACGATTGTGGGGTGCAATACAAGCCAACCGGGAACTACTTTGGAGCTCCGATCTA
CGAAGTAGGAGAACCGTGCTCGAAGTGCGACTGTGAGGGCTGCAAATGTAACAAGGACGATGGTCTTTG
CGTTACACCGTAAATCCAGCTGGAAAGTCTTCCAAATAAACTTGAAAAG Clone 48.1 (SEQ ID NO: 54)
CATCGATCCGATCCGATCCGATCCGATCCGATCCGATCCGATCCGATCGATCGATCGAT
CGTCGTCGTCGTCGTCGTCGTCG Clone 49.1 (SEQ ID NO: 55)
GATCCGATCCGATCCGATCCGATTCCGATTCCGATCCGATCCGATCCGATCCCGATCCCGATCCGATCC
GATCCCGATCCCGATCCCCGATTCCCGATTCCCGATTCCCGATTCCGGATTCCCGGATTTCCCGGATTT
CCCGGATTTCCCGGA Clone 50.1 (SEQ ID NO: 56)
GATCGATCCGATCCGATCCGATCCGATCCGATCCGATCCGATCCGATCCGATCCGATCCGATCCGATCC
GATCGATCGATCGATCGATCCGATCCGATCCGATCGATCGATCGA Clone 51.1 (SEQ ID NO: 57)
GATCGATCCGATTCCGATCCGATCCGATCCGATCCGATCCGATCCGATCGATCGATCGATCGATCGATC
GTCGTCGTCGTCGTCGTCCGCGCG Clone 51.2 (SEQ ID NO: 58)
GTTACAAAGGGAGTACAATATTTGAATGAAATCAAGGATTCGGTCGTTGCTGGATTCCAA
TGGGCAACAAGAGAAGGAGTTCTGGCTGACGAACACATGCGCGGAATTCGTTTTGACATCCAAGATGTA
ACACTTCACGCTGACGCTATCCACAGAGGTGGTGGCCAAATCATCCCAACTGCTCGTCGTGTAATTTAT
GCATCTGTACTCACTGCTGCACCACGACTTCTGGAACCCGTTTACCTCGTTGAAATTCAATGTCCTGAG
GTTGCCGTTGGTGGTATCTATGGTGTGCTCAATCGTCGAAGAGGACACGTGTTCGAAGAGTCACAGGTC
ACCGGAACTCCTATGTTTGTTGTCAAAGCCTACCTTCCCGTCAACGAATCATTTGGTTTCACTGCCGAT
CTTCGTTCGAATACCGGTGGTCAAGCTTTCCCTCAATGTGTTTGATCACTGGCAAGTTCTACCAGGA
GACCCACTGGAGCCCGGTACTAAGCCTAACCAAGTTGTTCTGGAGACAAGGAAGCGTAAAGGACTCAAG
GAGGGCGTGCCCGCTCTTGACAACTACCTTGACAAAATGTAAATCTATTGTTCCGGCTTGTTGTTACCG
AAGTTATCTAATAAAAAGGTTGTTGATGGAGCTGTTTCGCAGTTATTCGAAATTCCCGTTGTTTTATT
TATGCAAGAGCTAAATAAAGTTGTATAGCT Clone 52.1 (SEQ ID NO: 59)
GATCCGATCCCGATTCCCGGATTCCGGATTCCGGATTCCGGATCCGGATTCCGGATTCCGGATCCGGAT
TCCGATTCCGATCCGGAATCCGGATCCGGATCCGGAATCGGAATCGGAAATCGGAATTCGGAATTCGGA
ATTCGGAATTCGGAATTTCGGAA Clone 54.1 (SEQ ID NO: 60)
ATCGATCCGATCCGATCCGATCCGATCCGATCCGATCCGATCCGATCCGATCGATCGATCGATCGATCG
ATCGATCGATCGTCGTCGTCGATCGTCGTCG Clone 54.2 (SEQ ID NO: 61)
TATTCCTTAATTCTGGACCCGGAAACACTACCAGCCCCTTCAAATGCGAGTGGATGACCA
TTAAGGATGACGTGCTCTATGTTGGCGGTCACGGCAATGTGTTCAGAAATAGAGCAGGAGAAATTGTGC
ACAGCAACAACATGTGGATCAAAACCGTCACCCCGGAAGGAGAGGTTACCAATGTAGACTGGACAGATG
TTTACAACAACGCCCGAAATGCTGTCGGTATTTCTGAACCAGGATACCTTACACATGAAGCGGTTCAGT
GGTCAGAAACACAGGGACATTGGTACTTCCTTCCTAGAAAAGGAGTCAAAGACTGTCTACGTAGAAGAAG
AGGATGAGACAAAAGGCACGGATCTCCTGATTACTGGAAATCCGGACCTTGATCAATTCGAAGTCAAGA
GGATAGGAATACTGCGACCCGAACGCGGATATTCGGCATTCGATTTTATTCCTGGTACCGACGACAAGA
TCATCGTTGCCTTGAAGTCCAAAG Clone 55.1 (SEQ ID NO: 62)
GCGTCGATCATCATCGATCACATCATCACACACAAAAAAAAAACCCCC Clone 56.1 (SEQ ID NO: 63)
ATCGATCGATCCGATCCGATCCGATCCGATCCGATCCGATCCGATCCGATCCGATCCGATCGATCCGA
TCCGATCCGATCCGATCCGATCCGATCCGATCCGATCCGATCGA Clone 57.1 (SEQ ID NO: 64)
GATCGGATCGGATCGATCGATCGACGAACGACGACGACACGAGATGTCGTCGCGCCGGA Clone 58.1 (SEQ ID NO: 65)
GATCCGATTCCGATCCGATCCGATCCGATCGATCGTCGTCGTCGTCGTCC

TABLE 1-continued

*O. ostertagi* L4 cDNA library screen (with antiserum from protected calves immunised with pool 3 fraction from Trial 2 - see FIG. 1)

Clone 58.2 (SEQ ID NO: 66)
TTACGGCCGGGCTTCGGAGGTGCGATGAAGGGCATCTTGGGTTATACTGAAGACCAAGTTGTGTCGACT
GACTTCTTGTCTGACACACGCTCATCCATTTTCGACGCGGGAGCGTGCATCTCTCTTAACCCGAACTTT
GTCAAGCTCATTTCATGGTATGACAACGAGTACGGATACTCGCACCGTGTCGTCGATCTGCTTACCTAC
ATTGCCAGCAAGGCCTAAAATGTTTGCCGTGTTTGCTGGTTTGCGCTCTCAATCAAAGTTGTGGTTCCC
TAATGTTTCATAGAGTTAGTCACCACTATGAGCGTACATTTTTTCTGTAGTCTTGTAGGTTTCCTTTTT
TCTTTGGTAGCATGTAATTTATGTAGAGCTTTTATGTAATAAAATTTTGTGATGTAAAAC Clone 59.1 (SEQ ID NO: 67)
GATCCGATCCGATTCCGATTCCGATCCGATCCGATCCGATCCGATCGATCGATCGATCGTCGAT
CGTCTCTCGTCGATCGATCGACGACACA Clone 59.2 (SEQ ID NO: 68)
GGCATTACGGCCGGGGATCTGATTCGGAGGACCACAATGCCGAGACACTGGATCATCAATTCACTTTGG
TGAAGAAAAGAACGAAACAATCCCACGTGATGCGTTACGGTAGTCTGGATATAGCCAAAGAGCCACCCC
AAGAAGAGAAGGTGTCATGGCCATCAAGAGACGTCCAACTCATGCATCTGCAGATGCAGAAACTGTTCA
ATCCTCAAGCAGCCGCTGTCGACATCGAAATCAACAGAATCCAGACGGATCGACAAAACATTGAGGCAG
TTTTCACAAGTCTGATCAACCACCTCGTCGAAGATGGTAGCGAAAGGCGTCGTTTATTTGAGCAAAGGA
GCGATATTGAAAATCTCGACTGCCATGACGATGTCGTGAGGGTATTCGATATGATTTGCATTGACGTAA
ATAAGTATGACTATGCCCTGAAGTATGTGTATGTTCTGAACAACCTATGCACAAAGTTCAACGATTCGG
CGAAGATCATCAAGGCAATGTGGACTATCTGCTCAAAGACGCGCTCAAAGTTCCTCTGAAGCATCTTCT
TAATGAGCTCTGTCGATATTATTTCAGAATAAATATTCATGAAG Clone 60.1 (SEQ ID NO: 69)
GATCCGATTCCGATCCGATCCGATCCGATCCGATCCGATCCGATCGATCGATCGAATCCGATCGAATC
GAATCGATCGATCGATCGATCGGATCGGATCGGATCGGATCGATCGA Clone 61.1 (SEQ ID NO: 70)
GTCGTCCGATCCGATCCGATCCGATCCGATCCGATCCGATCGATCGATCGATCGAATCGATCGA
TCGAATCGAACGGAACGAACGACGGACGGATCCGGATCGGA Clone 61.2 (SEQ ID NO: 71)
CTCACGGCCGGGGGTTGCCAGCCAACCGATGATATCCCTAGAGCGAAGAAAGAGTCGAAGAGAAAGCAG
AGGCGCCAATTGGCTCGTGGAGAGTATTGAACATGATTGTTGTTGTTGTTCAGTAAATATTTTGTTG Clone 62.1 (SEQ ID NO: 72)
GTCGATCCGATCCGATTCGATCGTCGTCGTCGTCGTCGATCGACGATCGATCGATCGTCGATCGATCGT
CGTCGTCGTCGTCGATCGA Clone 62.2 (SEQ ID NO: 73)
TCGGCATTACGGCCGGGGGGAGTACAGTTCGGAGCAGTAGCAGTACAATATGCTGTTCTGCTTCGTATG
CCTTTCTCTCATCCTTAGCTCCGTATCCAGAGTGGAGTCAATTCTATGTTTGCATCAGTGCCGCCTGG
AGCTTCGGTAATGCAAGAATGCCGAGATCGGCTTCTCACATGCGAACACGATGCTAAAAATGGTTTCTG
TGAAGACCTGAGCGACTACTACATATATTATTGCTGTAAAAGTTGTAGCCAACTTGAGTCAGTTGAAAA
AAAAATGAAACAAGTTTCAATTCTATTCATCGATTTCAATAAACATTTCGCTTAC Clone 63.1 (SEQ ID NO: 74)
GGATCCGATCCGATTCCGATTCCGATTCCGATCCGATCCGATCCGATTCCGATCCGATCCGATCCGATT
CCGATCGATCGTTCGTTCGTTCGTCGTCGTCGTTCCGTTCCATTCCGA Clone 63.2 (SEQ ID NO: 75)
GCTTACGGCCGGGGGGCTCATCATTAATCCAGCACATTTCGCCATGATCTTCTACTTTGT
CTGTGCACTTTTCCTTCTCAACGCATTCACAGCTGAGGGTGCTGCCACCGCGCCATGTGAGGATCAAGG
AGGCGAGTCGTTCTGCCTTGGCCCAAAGCACGCCGGCCAGTGCAGCAGTCCGGACTTCCAGCCCATTGC
ACAGCAGTTCTGTGCTAAAACTTGTGGTATTTGTCACTGAATAATCTGGAGGATATTCACTAATAAAGT
TTCTCGGG Clone 64.1 (SEQ ID NO: 76)
GGATCGGATCGGATCGGATCGGATCGATCGATCGATCGATCGATCGAATCGATCCGATCGATCGGATTC
GGATTCGATTCGATTCGATCGATTCGAATTCGAAAATTCGAAAAATCGAAAAAATCGAAAAA Clone 65.1 (SEQ ID NO: 77)
GATCGATCCGATTCCGATCCGAATCCGAATCCGAATCCGATCCGAATCCGAATCCGAATCCGAATCCGA
ATCCGAATCCGGAATCCGGAATCCGAATCCGAATCCGAATCCGGAATCCGGAATCCGGAATCCGGAAAT
CCGGAAATCCGGAAA Clone 66.1 (SEQ ID NO: 78)
GTCGATCCGATCCGATCCGATCCGATCCGATCCGATCCGATTCCGATTCCGATTCCGGATTCCGGATTC
CGATTCCGATTCCGATTTCCCGATTTCCCGAATTTCCCCGAATTTCCCCGGAATTTCCCCCGGAATTTC
CCCCGGAATTTCCCCCGGGAAATTTCCCCCCGGGAAATTTCCCCCGGGAAAA Clone 66.2 (SEQ ID NO: 79)
GGGACAACAATGCTCGTCTATCTGTTGGTCGCTCTAATATTCCTCAACACCGTCACTGCA
CAAGCTGATGCAACCGCGTGCAAAGACGCCGACCCAGGGGATCTCGCCACGCCCTGTGAAAACCTCAAG
GACCAAGGTTTTTGCGACGATCTCGACATGCGCGACTACATGAACGACTACTGCAAAAGACGTGCAAG TABLE 1-continued

*O. ostertagi* L4 cDNA library screen (with antiserum from protected calves immunised with pool 3 fraction from Trial 2 - see FIG. 1)

TTTTGTATGCCTTAATGTGACTCTATCAAGTAAATTTCGGAGGGCTCATATCACTATGTCTTAAGTATC
GGATAAATGTCTAGCAAT

Clone 67.1 (SEQ ID NO: 80)
GCGATCGATCGATCCGATCCGATCCGATCCGATCCGATCCGATCCGATCCGATCCGATCCGATCCGATCG
ATCGATCGATCGATCGATCGATCGATCGATCG Clone 67.2 (SEQ ID NO: 81)
CGGGGACCAAACGATCCATTCGGCAATTATAAGGTTCTCTCATACAAGGAAGGACGCCGATTCGAATAC
GTCCATTACCCTTTCTTCGTTCTGCAATACGATGAGAGGAGGCAAACTTACAAAGCACACTACTTTGGA
TACATAGAGGAGGAGGACAAGCAAACAAAGAAGTTCACTCGCAAAATAGGTCCGTTGACCGCTGAGGAA
TTCACAACTAAATATAATCATTGCAACAAGTGGTGATAATGGTCGTCTACAACAAAACTTTGTCCACTT
CGATGAAAATAAATTTCGCAGTTGAAT Clone 68.1 (SEQ ID NO: 82)
GTCGATCGATCCGAATCGAATCGATCGATCGTCGTCTCTCATCTCCCACCTCCATCATATAT Clone 69.1 (SEQ ID NO: 83)
GTCGTCCGATCCGATCCGATCCGATCCGATCCGATCCGATCGATCGATCGATCGAATCGATCGA
TCGAATCGAACGGAACGAACGACGGACGGATCCGGATCGGA Clone 69.2 (SEQ ID NO: 84)
GCATTACGGCCGGGGTGTATTTAATAGTTAGAATTATAAAGGTAGAGTAAATAACTGTGA
ACTGTGTTAAAGTTAATTATTAATGACTCGGTGTTTCGGTGATATTTATTTGTTTAGAAG
TTTATTTATTTAAAAATTTATTATAATTAGATTTTGTTTGTTGATTTGTCGGAATTAAAA
TTAACAATACTGTGCTGTGTGCTTTTTGATATTTATTGTAAATGTTTTGTAAACGTTTTG
TAATTTTGTGTAGGTGGGTTTTGGTGGTAAGTTAC Clone 70.1 (SEQ ID NO: 85)
TCGATCCGATCGATCCGATCCGATCCGATCGATCGATCGATCGATCGATCGATCGATCGATCGATCGA
TCGATCGATCGATCGTCGTCGATCGTCGA Clone 70.2 (SEQ ID NO: 86)
TCGGCTTACGGCCGGGGTCCGGGTCGCAGTCGAAGGTGTCAGATGAGGACCTGGGAAGAGTGATGGGAA
TTTGCCGATGTCTTAACCTTTCCTTCACTGAAGAACAAGTGTTGGCGATAATCGCGGTAATCGAAGCAG
GAGCGAATCCATCTACGCTGGTGGATTGGTTGGCCGATATGGAAGAAGCAAAAGCGGGAGAGACAACTA
GCTTGAATTTTTGAAAAACGATTGATCGTAGAAGGATATTATTTGTTTTATTTATGTTCACGATTATTT
AAGAGAATATGTTGTGGCAGACGGGATGATCCTCTTTGATATTTATTGAGGGTCAATTATGTGAAGCAT
ATTGTTGTTTGCGGATTTTTCGCAAATAAATGTCATTTC Clone 71.1 (SEQ ID NO: 87)
GATCGATCCGATCCGATCCGATCCGATCCGATCCGATCCGATCGATCCGATCGATCGATCCGATCCGAT
CCGATTCCGATTCCGATTCCGGATTCCGGATTCCGGATTTCCGGATTTCCGGATTTCCCGGA Clone 72.1 (SEQ ID NO: 88)
GATCGATCGATCGATCGATCGATCGATCATCATCATCGATCGACGACGACGACGACGACGATCGATCGA
TCGATCGATCGATCGATCGA Clone 73.1 (SEQ ID NO: 89)
GATTCGATTCGATCGATCGTCGTCTCTCTCTTTTTTTTTTTTTTT Clone 74.1 (SEQ ID NO: 90)
GATCGATCCGATCCGATCCGATCGATCGATCGATCGATCGATCGATCGATCGATCGATCGATCGATCGA
TCGATCGATCGTCGTCGTCGTCGTCGA Clone 75.1 (SEQ ID NO: 91)
GATCGATCCGATCCGATCCGATCGATCGATCGATCGATCGATCGATCGATCGATCGATCGATCGATCTC
ATCTCATCGATCGATCATCATCA Clone 76.1 (SEQ ID NO: 92)
GATCGATCCGATCCGATCCGATCCGATCCGATCCGATCCGATCCGATCGATCGATCGATCGATCGATCG
ATCGATCGATCGATCCGATCCGATTCCGAATTCCGAATTCCGAATTCCGAA Clone 77.1 (SEQ ID NO: 93)
ATCGATCCGATCCGATCCGATCCGATCCGATCCGATCCGATCCGATCCGATCCGATCCGATCCGATCCG
ATCCGATCCGATCGATCCGATCGATCGATCCGATCCGATCGATCCGATCGA Clone 78.1 (SEQ ID NO: 94)
CGATCGATCCGATCCGATCCGATCCGATCCGATCCGATCCGATCCGATCCGATCCGATCCGATCCGATC
CGATCGATCGATCGATCGATCGTCGTCGTCGTCG Clone 78.2 (SEQ ID NO: 95)
GGCCGGGGACTTTACGATGTATATCGCATTGATTGCGGGGCAAACGTGACATTCAACCTGACTATCGGT
GATCATGTCTACACTCTCGAGTCGGAAAATCTTATTGTCAAATTTGATGTT
GATTTCTGTGCATTGGCAATATTCCCGATGCGCTCCGGCGGCTATGGACCCCAGTGGATTCTTGGCGAT TABLE 1-continued

*O. ostertagi* L4 cDNA library screen (with antiserum from protected calves immunised with pool 3 fraction from Trial 2 - see FIG. 1)

CCGTTCATACGCCAGTACTGCAACATTCATGACATCGGCAAACAGCGAATTGGCTTTGCAAAACCAGTC
AAGAAATAGCGATTTTGTGATGTTCTGATTAGATGGTATAAA
TGCTTCAC

Clone 79.1 (SEQ ID NO: 96)
GTCGATCGATCGATCGATCGATCGATCGATCGATCGATCGATCGATCGATCGATCGATCGATCGATCGA
TCCGATCGGATCCGGATTCGGATTCGGGATTCCGGGATTCCGGGA Clone 79.2 (SEQ ID NO: 97)
TCGGCTTACGGCCGGGGTAGAAGGAAGTGAATTAGCTAAGGCTGAAGCACTTATACGAGCTGAGGTTGC
TGACGCGTTGCTGAAGGCTGCCACTGGACAACAATAAATGTAACATAGGCCAATTTAGGATGGATTCTT
TGCAAATTCAAAAACCACTCTTAATGGCAATTTTCTAAAATTTAATAGTGTTAACTTCATACTCGCCCT
TGGTTATCGTACTATAGACTGATTGACGTTGAT
GTAGTGAGAATAAATATCCTTCTATTATATAAAGCGCTAACTTTGT Clone 80.1 (SEQ ID NO: 98)
ATCGATCCGATCCGATTCCGATTCCGATTCCGATTCCGATTCCGATTCCGATTCCGATTCCGATTCCGA
TTCCGATTCCGATTCCGATTCCGATTTCCGATTTCCGATTTCCGATTTCCGGATTTCCGGAAT
TTCCGGAATTTTCCCGGAA Clone 81.1 (SEQ ID NO: 99)
GTCGATCGATCCGATCCGATCCGATCCGATCCGATCGATCCGATCCGATCGATCCGATCCGATCCGATC
GATCGATCGATCCGATCCGATCCGATCCGATCCGATCCGATCCGA Clone 82.1 (SEQ ID NO: 100)
GATCCGATTCCGATTCCGATTCCGGATTCCGATCCGATCCGATCCGATCCGATCCGATCCGTCGATCG
ATCGATCGATCGATCGATTCGATTCGATTCGATTCGATTCGATTTCGA Clone 83.1 (SEQ ID NO: 101)
GATCGATCCGATCCGATCCGATCCGATCCGATCCGATCCGATCCGATCCGATCCGATCCGATCCGATCG
ATCGATCGATCGATTCGATCGATCGATCGATCGATCGATCGA Clone 83.2 (SEQ ID NO: 102)
AGGGCGTAAACGACGTGTAGACATGTAGATTATTTCGATTCCTTCTCCACGATGACCCCA
TGTGAAATAAGCCCCTGTGCGATTCCATGTGCCTCTAGATTCTCATACTTGCAAGCCTTA
CCAATTTCGGCGACCTAGGCGCCTTCTGACGGCGTCCGCTCTTCGATGTTGCTTTTTCCCAACTCCGTA
AAACCAGCAACATCAGTGAACAGCTCGTGGGCGCTCTGCCTAGCTGCCACGCGCCGTCGATTACTTGTA
TATGTCTTGTGAATATTACATTATTTACGGATATCATGTGGAAATAAATTATTG Clone 84.1 (SEQ ID NO: 103)
ATCGATCCGATCCGATCCGATCCGATCCGATCCGATCCGATCCGATCCGATCCGATCCGATCGATCCGA
TCGATCGATCGATCGATCGATCGATCGATCCGATCGA Clone 85.1 (SEQ ID NO: 104)
GGTCGATCGAATTCGAATTCGAATTCGAATTCGAATTCCGAATTCGAAAATTCGAAAATCGAAAAATC
GAAAAATCGAAAAATCGAAAATCCGGAAATCCGGAATCCCGGAATCCCGGAATCCCCGGAATCCCCGGA
ATCCCGGAATTCCCGGAATTCCCGGAATTCCCGGAATCCCGGAA Clone 86.1 (SEQ ID NO: 105)
ATCGATCCGATCCGATTCCGATCCGATCCGATCCGATCCGATCCGATCGATCGATCGTCGATCGATCGT
CGTCGTCGTCGTCGTCGTCTC Clone 87.1 (SEQ ID NO: 106)
ATCGATCCGATCCGATCCGATCCGATTCCGATTCCGATCCGATCCGATCCGATCCGATCCGATCCGATC
CGATCCGATCCGATCCGATCCGATCCGATTCCGATTCCGGAATTCCGGAATTCCGGAATTCCGGAA Clone 88.1 (SEQ ID NO: 107)
GATCGATCCGATCCGATCCGATCCGATCGATCGATCGTCGTCGTCGTCGTCGTCTCGTCGACGCCCTCC
CCG Clone 89.1 (SEQ ID NO: 108)
GATCGATTCCGATCCGATCCGATCGATCCGATCGATCGATCGATCGATCGATCGATCGATCGATCGATC
GATCGATCGATCGATCGATCCGATCCGATCCGATCCGA Clone 90.1 (SEQ ID NO: 109)
GATCGATCCGATCCGATCCGATCCGATTCCGATTCCGATCCGATCCGATCCGATCCGATCCGATCCGAT
CCGATTCCGATTCCGATTCCGATTTCCCGAATTCCCGAATTCCCGAATTCCCCGAATTCCCCGGAATTC
CCCGGAATTCCCCGGAAA Clone 91.1 (SEQ ID NO: 110)
GATCGATCCGATCCGATCCGATCCGATCCGATCCGATCCGATCCGATCCGATCGATCGATCGATCGATC
GTCGTCGTCGTCGTCGTCGCC Clone 92.1 (SEQ ID NO: 111)
CATCGATCGATCCGATCCGATTCCGATCCGATCCGATCCGATCCGATCCGATCCGATCCGATCCGATCC
GATCCGATCCGATCCGATCCGATCCGATCCGATCCGATCCGATCCGA

TABLE 1-continued

*O. ostertagi* L4 cDNA library screen (with antiserum from protected calves immunised with pool 3 fraction from Trial 2 - see FIG. 1)

Clone 93.1 (SEQ ID NO: 112)
GGATCGGATCCGGATCCGATCCGATCCGGAATCCGGAATCCGAAATCCGAAATCCGAAATCCGAAAAT
CGAAAACAAAACAAAACGAAATCGAATCGAATCCGAACCGACCGACCGACCGACGAC Clone 94.1 (SEQ ID NO: 113)
GATCGATCGATCGATCGATCGATCGATCGATCGATCGTCGATCGATCGTCCGTCCTCTCGATCGTCGCG
TCGTCGTCGTCGATCGA Clone 94.2 (SEQ ID NO: 114)
CGGCATTACGGCCGGGGAGAGAGGGTGATTCAACAGCTGTCAGAGTCCCCTCCTATACGCGCACTCGCT
CGAGCAATGGTACGTGGAGGAAAAACAGTCCAGGACAAGCTCGGTAACACGGAGGTTGCTTCGCGACTG
GAGAAGTTTACAAAGCTCTACCAAGAAGAATTCCAGAAAGCACTGAAAAAATAGCTCGAGTGAGGTGTA
TGCAGTCATAGAATAATATGGGTAGTAATAAAGAATTCTGATT Clone 95.1 (SEQ ID NO: 115)
TCGTCGTCGTCGATCGTCGTCGTCGACCCCACACGACCCTCACACA Clone 95.2 (SEQ ID NO: 116)
TGATCCATGCGGTTGATGGCGACTGTCGTCTTGCCGTGCTCGCTGCGGTAGCCCACCCCATGGGTGTCC
GGCATGAAATAGCTGTCCATCTCCACGAGGGTAAGGCGGCCCCGTACCATCTGTGCGGCCACGTGGCTT
TCCACCGTGTCAAAGATGGCAAGCTCGCCGACGCGAATGCCATAAAGCGTCTCCAGATCCTCCAGCGGC
ACCTTGAAAAAGGTAAACTGATCACCTTCAAAGTCCTGGTTCAGGGTGAAGCCCAGCATTGCTTCCGGC
GGCAGGTTCTGTGCAGCAAGAACCTCGATCCACAGATCAACGTAGCAGTTTGTCTCCGGCCAAATCCGG
TCCTGCGCATGCAGGGCATGCGGCCGGTAGGTCTGCGGATCGATATGGGGGAAAACAGCTTGCATGCCG
CCGGTCAGCCCCACAATTCCTGGCGAACCTGTTCCGGCCAGGCTTCGATATCGAGGCCATGATGGTGGA
ACAGGGCAAGCGCAATCCGCTCCAGGCCAAATCCGACACAGGCAGTATGGGCGGTCGTGCCATCAGCGA
ATTGAATGCCCCATTTCGTGCCGAAATGATCCTGATGATAGTTGAAGCTTATGCATGCGGCCGCAAG Clone 96.1 (SEQ ID NO: 117)
ATCGATCCGATCCGATCCGATCCGATCCGATCCGATCCGATCCGATCCGATCCGATCCGATCCGATCCG
ATCCGATCGATCCGATCGATCCGATCCGATCCGATCCGATCCGA Clone 96.2 (SEQ ID NO: 118)
ACTTGAGGGGAGGCGCCAAGAAGGTTGTCATCTCCGCACCATCAGCAGATGCCCCGATGTTTGTTATGG
GTGTAAACAACGAGACTTACAACGCTGCCAACAACCACATTATCAGGAACCCG Clone 97.1 (SEQ ID NO: 119)
CATCGATCGATCCGATCCGATCCGATCCGATCCGATCCGATCCGATCCGATCGATCGATCGATCGATCG
ATCGATCGATCGATCGTCGATCGTCGTCG Clone 98.1 (SEQ ID NO: 120)
GATCCGATCCGATTCCGATCCGATCCGATCCGATCGTCGTCGTCTCTCCC Clone 98.2 (SEQ ID NO: 121)
GACCAGAACGCCACCACTACACAATGTTGGAGTACAAATGAGTACACCGCATTTTACTGA
CAGGTATCCCTATGTGCGTTATAGCTACGGAAATACGGACACCTCCTTAGGCATCGCTACTCAATCCGA
GTCTGTATACGCTAGAAGTACTGCCGTTCGAGATATTGGTACGAAACGGTGGTTGGAAGGCAAGTTGAC
CGCGTACAACCCATCTCAATTTCAACATCGAGCGGACTATAGACCAACATACGAACGTCCACATGTGCC
ACAGAGAAGCTACATAAGGTACATGCCTGTTGACGACGCCGTCGATATGTATAAGAAGAGATGCATGAC
TGTTGGGACCCTGTCAAAGTACTGGCTATCCCTGCCACGTGGGCCTCTCGAAGAGACAAGGAATTGAA
TCTGTCATCGTCGCTGAGTCGTGGAAATTACACCTACACCAACAAATATAACAGATTCAGCAGCCGTCT
ATACTAACTGCAGAAACACTGCCCTTACATCATTTGGTCTATCAGCTATCAAACGTTTCCGACCTTTCA
TTATGTTCGATCGTTTGCTCATATCTTAACGGAGGAATACTATTGAATGAATCTTTTAT Clone 99.1 (SEQ ID NO: 122)
ATCGATCGATCGATCGATCGATCGATCGATCGATCGATCGATCGATCGATCGATCGATCGATCGATCGA
TCGATCGATCGATCGATCGATCGATCCGGA Clone 99.2 (SEQ ID NO: 123)
GGAAGAAGTGCGGTGAAGAAGGTGGAGCGAAATGCTGCGAAGGAAAACCATGCTGCAAGTAATTTCGCC
CGAGATGTCGAACGGTGGACGTGGTCATCATGGTCGCCTAGCTATCTGCGATCTACACCACTGATCAAC
AGCGATAATTCCCTTGTGCAGCTGTAATTTCGTATTTAAATTTCCATATTTGTCCGTTTGTTTGTGTTC
AGTGTGAGTGTGAAAGCGCGATAATTGTGTTTTTAAGTGTGTATTCCTCATCGGCATAGTCGAATAAAA
TTTTCTGC Clone 100.1 (SEQ ID NO: 124)
GATCCGATTCCGATTCCGATTCCGATCCGATCCGATCCGATCCGATCCGATCCGATCGATCCGATCGAT
CGATCGATCGATCGATCGATCGATCGATCGATCCGATCCGA Clone 101.1 (SEQ ID NO: 125)
ATCGATCCGATCCGATCCGATCCGATCCGATCCGATCCGATCCGATCCGATCCGATCGATCCGATCGATCGATC
GATCGTCGTCGATCGTCGTCGTCGTCGATCG Clone 102.1 (SEQ ID NO: 126)
ATCGATCGATCCGATCCGATCCGATCCGATCCGATCCGATCCGATCCGATCCGATCGATCGATCGATCG
ATCGATCGTCGTCTCGTCGTCC TABLE 1-continued

*O. ostertagi* L4 cDNA library screen (with antiserum from protected calves immunised with pool 3 fraction from Trial 2 - see FIG. 1)

Clone 103.1 (SEQ ID NO: 127)
GATTCGATTCCGATTCCGATTCCGATTCCGATTCCGATTCCGATTCCGATTCCGATTCCGATT
CCCGATTTCCGATTTCCGATTTCCGGATTTTCCGGAATTTCCGGATTTTCCGGAATTTCCGGAATTTCC
CGGGAATTTTCCCGGGAAATTTTCCCGGGAATTTTTTCCCGGGGAAATTTTTCCCGGGGAAA Clone 104.1 (SEQ ID NO: 128)
CGATCGATCCGATCCGATCCGATCCGATCCGATCCGATCCGATCCGATCCGATCCGATCCGATC
CGATCGATCGATCGATCGATCGATCGATCGTCGTCG Clone 105.1 (SEQ ID NO: 129)
GGGACGTTTCGATCCATCGAATTCGATTCGTCTCGACGAACACGCGTCTCATCACGTCTTCATAGTCTT
GAGA Clone 106.1 (SEQ ID NO: 130)
GGGCAATTTTCAAATTCAAATTCAAATTCAAATCGGATTCGGTTTCGATCATCGATTTCATTCATTTCG
TCTCATTTGTTATGTTGATTGGTCGAGTGTTA Clone 106.2 (SEQ ID NO: 131)
TATTTTGTTAAGTTGATTGGGTCAGTGTTTAGTGGAAGAGCCTTTTACTACACTAAGTCC
TATTTTTTCGTTTATTTATTTTTTATTATTTTTATTATGATATTAATATTTAATTTTAG
TAAAAAATTGTTTATT Clone 107.1 (SEQ ID NO: 132)
GGGGGATCCGGATTCCGATTTCCCGGAAATTCCGGATTTCCGAATTTCCCGGATTCCCGATTCCCGATT
CCGGATTCCGATTCCGGATTCCGATCCGATTCCGATTCCGATCCGATCCGATCGATCCGGTCCGATCCG
AATCGATCGTCG Clone 108.1 (SEQ ID NO: 133)
GAAAAAAAAAAAAAAAAA Clone 109.1 (SEQ ID NO: 134)
GGGACTTCATCCGGATCGATTCATCCTCATCCTCGGATTCGATCGTCCATCCGAACGACCACATCGACG
ATCGAATCACGTCGATCGATCCGA Clone 109.2 (SEQ ID NO: 135)
GACGGGGATTTACGGAATGTTACTACTGGATTGAGTCTCCAAAAGGAACCACAATCGAAGTGAAATTAG
CGGATTACCCATGGGGTTATGTTGGTTCAGGATGCAGTGTTGCTGGTTTCGAGCTCAAAACCAACAAGA
ACCAAACACTTACTGGCTACAGGTTCTGCACTCCTGAGGGTGTTGGACATGTGTTTCAATCTTACACAA
ATCGTGTGCCAGTGATTACGTACAGCAGCTCTCTTTATAATTTCATAACCACTGAACTCGAATATCGAT
ACGTTCCTGGACGTCCATCTGCCTAAACGATTTCTGCATATGGACACTATTATGGCCATCAGAGTGATA
AAGTGCTGAAGTGACTTTTCTGTTGCTAAACTTCGCGGTTTAATAAAGTTTTCGC Clone 110.1 (SEQ ID NO: 136)
GCATCGATCGATCCGATCCGATCCGATCCGATCCGATCGATCCGATCCGATCCGATCCGATCGATCGAT
CGATCGATCGATCGATCGATCGTCTCGTCG Clone 111.1 (SEQ ID NO: 137)
GATCGATCGATCCGATCCGATCCGATCCGATCCGATCCGATCCGATCCGATCCGATCGATCGATCGATC
GATCGATCGATCGATCGATCGTCGATCGTCG Clone 112.1 (SEQ ID NO: 138)
GGGGGAATCGGATTTTCCGAAAATTTCCCCCGAATTTTTCCGGGATTCCGGATTCCGGATCCCCGGATT
TCGGATTTCGAAATTCGATCCGAATTCGATTTTCGATTCAATCGAACGCGGTCGTCACAGTACGTCG Clone 113.1 (SEQ ID NO: 139)
GGGACGATCGATCCGATTTCCGATTCCGGATCCCGGATCCCGATTCCCGATTCCGGATCCCGGAATTCC
GAATCCCGGAATCCGGAATTTCCGGATTTCCGGATTCCCGATTTCCGAAATTTTCCGGATTTTCCGGAT
TTCCGGATTTTCCGGATTTTTCCGAATTTCCGAAAATTTTTCCGGA Clone 114.1 (SEQ ID NO: 140)
GCCTCATCGATCGATCATCATCATCATCATCGTCTCATCTCTCGTCGTCTCTC Clone 115.1 (SEQ ID NO: 141)
GGAATTATCTTTGGAAAAAAAAAAAAAACAAATCGATCGTCCGTCCGTCCGTCCGCCGTCGATCGTCTC
ATCGATCGATCGATCGACGACGATCGA Clone 116.1 (SEQ ID NO: 142)
GGGCCGTCACGTCGATCATCGACGCAACGTCGCTGTCGTGTCATCAGTCGTGACACG Clone 117.1 (SEQ ID NO: 143)
GGGCTGGCACGGAATTCCTTCACTCACGATCGTGTTGTTTGGAGATAGCTGTGAGTGCTGCG Clone 117.2 (SEQ ID NO: 144)
AAATACTAGAATGTGTTGTTTTGGGAGAATAGCTGGTGGAAGTGCTGCGTCTATTAATT
ATGGCCATGAAGAACTTTGAGTTTCCAGCACTTACAATTTCAAAATGTGATCTGTCACGA
GTTTTTACGTAGCCGGTTGTTTCATAATCAGGCCATTATAATTGTTTGGGCAGCATAGTA TABLE 1-continued O. ostertagi L4 cDNA library screen (with antiserum from protected calves immunised with pool 3 fraction from Trial 2 - see FIG. 1)

TTTTATTGTTCACTTTTTGACATGTTTGGCTTTGTGTGTTGTGAATACTGACAATAAAGT
AATTCGTAC

Clone 118.1 (SEQ ID NO: 145)
GGGAATGTTGACAGTGAAGAGTAATTGTTCTTGTTATCATAATGTGTTTAAAAAAAAACGCG Clone 119.1 (SEQ ID NO: 146)
GGGTATACCTGTGGCGGATTCATTTTGATATTTGGCAAACTAATACAATTATGCAAAAAAAAAAAAAAA
AATG Clone 120.1 (SEQ ID NO: 147)
GGGATTCACGTCGGCTCATCCAGCTTGGCTCGACAGTGAATCGACCACGACAGTGTCATCCAACACA Clone 120.2 (SEQ ID NO: 148)
GGGCACAAGAATCGACCACGACAGTGTCATCCAACACAGTGCCGGTAACTATCCCGATCAAGGTACCCC
GGGCGTTTCCAGAAACTGGATCGTTCGGATCATTCGGATCTTATGGAAAGGCTGGTCTTGCATGCTAAT
CAAATAAAGCATTTGGTTTAC Clone 121.1 (SEQ ID NO: 149)
GCTCATCTCGATCGTCATCATCATCATCGCATCCCTCCTTA Clone 122.1 (SEQ ID NO: 150)
GGCCCTTCACTCGATGTCACACATCATCGCATAGCTTATGTTATATTTGATAAGTTAGAAG Clone 123.1 (SEQ ID NO: 151)
GGCATTCGATCCGATCGATCCGGGATCCGATCCGATCCGATTCCGGATTCCGATCCGATTCCGGGATCC
GATCCGGATCCCGGGAATTCCGAATTCCGGGATTTCCGGGATTCCGGAATCCCGAAAAATTCCCGGATT
TCCCCCCCGGATTTCCCGGGGATTTCCCGGGGGGGGGAA Clone 124.1 (SEQ ID NO: 152)
GATCATCGATCGATCCGATCCGATCCGATCCGATCCGATCCGATCCGATCGATCGATCGATCGA
TCGATCGATCGATCGATCGATCGATC Clone 125.1 (SEQ ID NO: 153)
GGGATACTGGATCAGACAGCACACCATTCCTCTGTCTTCAGTAACCTATAGAGATATAA Clone 125.2 (SEQ ID NO: 154)
AGGCACATCCCATTTCCTCTGTTCTTAAGTAAAACCCTATAGAGAATATAACTAACTTGA
TAAAAGACAGTGCTTCTTATTCAAGA Clone 126.1 (SEQ ID NO: 155)
GGTACGAAAGGAGAACCATCGCAACAACGAACGACTCGTAGTGTTCCGGTCGTCGCACTGCAGTG Clone 126.2 (SEQ ID NO: 156)
GCAAAACATACGAAGACTGTAAGTGTTCCGGCTGCACTTGCAGTGTAGAAGAAGCGCTCT
GTGTTGCTCCTTAACACCTATGTCAATAAATTTTCATCAATAAAAAAAAAAAAAAAAAAA
AAAAAAAAAATTG Clone 127.1 (SEQ ID NO: 157)
GGGCGAATCATCGAATCGCGACCGCGCAATTCGTCACGTCGACTTCGTGACGCGTAGTACTGCACG Clone 127.2 (SEQ ID NO: 158)
CAATGTGAGCGTAGTACTTGCAAGCGCCCATTTGCTATCATAGCACTGATTTCTCTCGTC
TTTTTCTCAGTTATTGAAGGTTTATATTCTATCCGTGTGGTTTCCTTAATATTTAGTCAA
CCAAAAGAGTGTTATGCTCAACACAGTCGTTGACGGATTGGTGGTTGTTCATTCTTCGCT
GCCGACCTCGCGAATGTCTCGAGAAGAACCAACTGCTTCCGTTCATCCCCTCATGCAAGTCATATGTCA
TACAGTGTGTTATGAGATTATTGTGATGAATAAAGAGTTG Clone 128.1 (SEQ ID NO: 159)
GGGGGGATCCAAAATCGGAATCCGGAAATCCCGAATCCGGGAATCCCGAAATCCGGATCCCGAATCGG
AATCCCGATTCGGGATTCCGGAAATCGGAAATCGGTCCCGATTCGGTCCCGGATCCCGAATCGGAATCG
GAAATCGGAAATCGGGAATCGGGAAACGGGAA Clone 128.2 (SEQ ID NO: 160)
GTAAATCTGACATCCAAAACAACGATCGATCACTCTCATCTCTCATCATCTACATGTTCT
TCTCCTCGCTTTCGACACTTCTTGAACAATTTCGCTATTGTGTGAGTGTGTAAAACGTGG
CT Clone 129.1 (SEQ ID NO: 161)
GGGACGATCGGATCCTCGATCCGATTCGGATCCATCGTCCATCCAATCACACCATCCGGTCGTCGGATC
GATCGTCGTTCGTCGCCAACCACCGA Clone 130.1 (SEQ ID NO: 162)
GGATCGTCCGTCGTCCGTCATCGATCACGCTCGCGTGTGCGTACACAC

TABLE 1-continued

*O. ostertagi* L4 cDNA library screen (with antiserum from protected calves immunised with pool 3 fraction from Trial 2 - see FIG. 1)

Clone 131.1 (SEQ ID NO: 163)
GGGGGAGTCATCCGAACGATCGGTCGTCGACGTCGTCGGACATTCGGTTCACGCTATTGATGCTGATCA
CGATCGTC Clone 132.1 (SEQ ID NO: 164)
GGTGTCCATCGTCCGATCATCGCACGATCGACGTCGCTCTCCTCCGTGC Clone 133.1 (SEQ ID NO: 165)
GCTCATCGATCGAATCGAATCGATCCGATCCGATTCCGATCCGATCCGAATTCCGAATCCGAATCCCGA
TTCCCGATTCCGAATTCCGGATTTCCCGGGGATTCCCGGAATTTTTCCCGGAATTCCCGGGGAATTCCC
GGAATTTCCCGGGAATTCCCCGGAA Clone 134.1 (SEQ ID NO: 166)
GGTAACGATCGATCGATCGATCATCCGTCCATCGATCATCGTCTCATCGTCGATCACGACGTCGATCTC
GACATCATCG Clone 134.2 (SEQ ID NO: 167)
GGCGGCATGCGGCGTGTCCTTGTTTAACGGAACGGAATGAAGAAGAGAAAAAGCTTTCTTAAAGTAACG
AGGCCAATAACGGATCGCAATGAAGATCTAATAGAGCTGTACGGCTACTTCTCTGATTTCCTTCAGTAT
ACAAAAAATGTTGTTAGTATCCGCAATCGTCTAGGGGAAACGATCTTATTAAGAAAGTAGAAAGAAATA
GCTAACACCTATTTCGTTTCTTGATTTTTTGAA
CCACTGGCGTAAATGCTCTTACACATGTTTCCCATGAAACCAGGGTTTTCCGTTATCCTA
GTCTTCCTCATAATCAAATGATCTGGTAXTTCCTGGATGXCGTTTCCTCTTTCTACCAAG
ACCXTCATCXTCXXATXACXACAACGCC Clone 135.1 (SEQ ID NO: 168)
ATCGATCGATCCGATCCGATCCGATCCGATCCGATCCGATCCGATCCGATCGATCGATCGATCG
ATCGATCGATCGATCGATCGATCGTC In a further embodiment, the antigens and/or vaccine/vaccine compositions provided by this invention may comprise proteins and/or peptides comprising sequences encoded by any one of the nucleic acid sequences shown in Table 1.

Table 2, below, identifies some specific proteins/peptides encoded by cDNA sequences comprising the nucleic acid sequences detailed in Table 1.

| *O. ostertagi* L4 cDNA library screen | |
|---|---|
| Clone I.D. | |
| 1.1 | Cathepsin B6 |
| 2.1 | Ser/Thr protein phosphatase (Wormbase) |
| 3.1 | GAL-1 |
| 4.1 | no hit |
| 6.1 | Myosin |
| 7.1 | ?apyrase (T. circ. 40.3 kDa protein) ?thrombospondin (wormbase) |
| 8.1 | ASP-like protein ? |
| 8.2 | ? Cytochrome b5 |
| 9.1 | Globin-like host-protective protein |
| 10.2 | T. circ similar to Cadherin |
| 11.2 | ASP-like protein ? |
| 12.2 | NADH dehydrogenase ND4L |
| 14.1 | G-protein coupled receptor (Wormbase) |
| 14.2 | *Haemonchus* est contains THR repeat element |
| 18.1 | Cathepsin B |
| 18.2 | Cysteine PRotease related family member (cpr-6) |
| 19.1 | NADH ubiquinone oxidoreductase |
| 21.2 | Unknown |
| 22.2 | Putative amino acid permease |
| 23.1 | unknown |
| 29.1 | Unknown |
| 30.2 | Unknown |
| 31.1 | *O. ostertagi* est |
| 31.2 | Unknown |
| 32.2 | Unknown |
| 35.2 | Prolyl Carboxy Peptidase like family member (pcp-4) |
| 36.2 | Amine transmembrane transporter activity |
| 37.2 | Unknown |
| 38.1 | Ribosomal protein |
| 38.2 | Ribosomal protein S19S |

| *O. ostertagi* L4 cDNA library screen | |
|---|---|
| Clone I.D. | |
| 42.1 | Putative cytochrome c |
| 45.1 | C-type single domain activation associated secreted protein ASP3 precursor |
| 51.2 | Putative Elongation Factor |
| 52.1 | ubiquitin |
| 54.2 | APYrase family member (apy-1) |
| 58.2 | Glyceraldehyde-3-phosphate dehydrogenase |
| 59.2 | Legumain |
| 60.1 | T. circ adult cDNA |
| 61.1 | O. ost L4 est |
| 61.2 | 60S ribosomal protein |
| 62.1 | metallo panstimulin |
| 62.2 | Unknown |
| 63.1 | T. circ est |
| 63.2 | Unknown |
| 65.1 | Ribosomal protein |
| 66.2 | Formate dehydrogenase |
| 67.2 | 17 kDa ES antigen protein |
| 68.1 | *O. ostertagi* putative ES protein |
| 69.1 | *H. sapiens* chromosome 4 |
| 69.2 | Unknown |
| 70.1 | unknown |
| 70.2 | Unknown |
| 75.1 | *O. ostertagi* library |
| 77.1 | T. circ est |
| 78.2 | Aspartyl protease precursor |
| 79.1 | *O. ostertagi* similar to ATP synthase |
| 79.2 | ATPase, F1 complex, epsilon/delta subunit |
| 80.1 | *O. ostertagi* cytochrome c oxidase |
| 81.1 | unknown |
| 83.2 | Neuropeptide-Like Protein family member (nlp-42) |
| 87.1 | Antigenic glycoprotein precursor 30kDa |
| 89.1 | unknown |
| 91.1 | unknown |
| 92.1 | lumen protein? Receptor |
| 94.2 | Unknown |
| 95.1 | unknown |
| 95.2 | Isoleucyl tRNA Synthetase family member (irs-2) |

*O. ostertagi* L4 cDNA library screen

| Clone | I.D. |
|---|---|
| 96.2 | Glyceraldehyde-3-phosphate dehydrogenase |
| 98.1 | unknown |
| 98.2 | Unknown |
| 99.1 | Cadherin metallothionin |
| 99.2 | Unknown |
| 100.1 | Protein disulphide isomerase |
| 103.1 | Ribosomal protein |
| 106.2 | Cytochrome b |
| 109.1 | unknown |
| 109.2 | Metalloprotease ] |
| 112.1 | Cytochrome c oxidase |
| 113.1 | Ribosomal protein |
| 116.1 | Elongation factor |
| 117.2 | Unknown |
| 118.1 | unknown |
| 120.1 | *O. ostertagia* |
| 120.2 | Unknown |
| 125.2 | Rab3 GTPase-activating protein |
| 126.1 | ASP3 precursor (ES protein) |
| 126.2 | C-type single domain activation associated secreted protein ASP3 precursor |
| 127.2 | Alpha-ketoglutarate-dependent sulfonate dioxygenase |
| 128.1 | Troponin |
| 128.2 | Troponin family protein |
| 129.1 | Aspartyl protease |
| 134.2 | NADH dehydrogenase subunit 4 |

TABLE 3

*O. ostertagi* L4 cDNA library screen (with antiserum from protected calves immunised with pool 3 fraction from Trial 3 - see FIG. 1)

Clone 1.1 (SEQ ID NO: 169)
CGGCTTACGGCCGGGGACGTGAACAGGCAGCCAAGGCCGCAAAAGAGGCGAACAAAGCAGCTCGAGCAG
CCAAAGCTGCCATGAACAAGGAAAAGAAGCCCGCTGCACAAAAAATGAAACCACCGAAGCCAGTGAAGA
CTGCTGCACCCCGAGTCGGAGGAAAACGTTAAGCTTGGATAGCATGTTGTTTGTTATTGCAAATAAATA
TTGTTATCGT Clone 2.1 (SEQ ID NO: 170)
CATCGGCCNTAGGCGGGGGTATGAAGAATATCGACAAAGACGATACTTGCGTTATGTATTCTGTGCTGG
CGTATGACGCAACCAGTGAAATTCACGAAACTATTGTGATGGTTCTCATAAAGAATGAGACGGGAAAAG
TCAGATCTCACTACTTCAAGTATCAGGTGATAACTGATAAGACAACAAAGAAACAAAGCACTTGGATTG
ACGACATGGACGCGCTTAATTTCATGTTAACGATAAGAAAGTGTAAGCTCGTCCCTTCTAGAGGTTAAA
ATCCGTCTTGAATGAATGGACATGAAATAAATTTTCGCAGCTGTAAGAAGG Clone 4.1 (SEQ ID NO: 171)
ACGGATATCAAGGTCGATTACAAGTCACATAACAAAGCTGGTGAATACCAGTTAGTTAGC
TGTAGAAGGCCAATAAGTGACGAGGAATTGGAGGATCCAGACGTTGCTATGAAGCAACTGGAACTGCAA
ATCAAAAAGGAAATGCTGATCTCGGATTTAATGAAGTCTAAGCGAAAGCTTACAAAAGAAGAGCTGAGT
ATTCTCAATGAGGAACTGCCTGTTGGACAAGCGAAAAAGTCATGACCGATCACTCAGTTGTAGTATAGC
TAGGTTTTCAATTAAC Clone 5.1 (SEQ ID NO: 172)
CGGCTTACGGCCGGGGTGGAACAAGATTTTCCGCATCCTTAAGGCCAAGGGCATGGCTCCGGAAATCCC
TGAGGATCTCTACCATCTGATCAAGAAGGCGGTATCCATCCGAAAGCACCTTGAGCACTCGCGCAAGGA
CATTGACAGCAAATACAGATTGATTCTTGTTGAGTCTCGAATCCATCGTTTGGCTCGCTACTACAAAAC
CAGCCGTCAACTCCCAGCGACCTGGAAGTATGAGTCGGCGACCGCTGCCTCACTCATCTCATAAAGTTG
TTTTGTGATTATTTGTTATAAATTGTTG Clone 6.1 (SEQ ID NO: 173)
GGCATTACGGCCGGGAGAGGAGGGAAGTTTACAAACCATACTACTTTGAATACATAGAGGAGGAAGACA
AGATAACAAAGAAGTCCACTCGCAAAATAGGTCCGTTGACCGAAGAGGAATTCACAACTAAATATAACC
ATTGCAAAAGGTGGTGATAATGGTCGTCTTGAACAAAATTTTGTCCACTTCGATGAAAATAAATTTCGC
AATTGAC Clone 7.1 (SEQ ID NO: 174)
CGGCATTACGGCCGGGGCATAGAACAATTGTATTGAATGATACCATATCGCATCAAGCTT
ATACAAGATTAAAGAAAGGACTTGGGACCTTGAAGTATCCCTGCATCGAGCGCGCTGTCATACAGGAAT
TTCTGTACTGGCTCAAGATGGAAATGTCGCTAAAAATATATTACACCCTCCGCGGTCTCGAGATGTACA
GGACTGATATCGAGGAGCTTCCCGAAGGAGCGCAATATGGATGCCACCATCTCCTTGCTCGAGGTTATA
GCTTTCAGCTCATGCGTATTTTTGCTTCTTCCGAACAACCCTAAAAAATGATTGGATTATCCATTAAT
GACCTTTATAAGGTCTGTAAATTTCGCTACATTATGTGCTCGTTTGATAAAATCTGCATAAAACGATTC
CGTACG Clone 8.1 (SEQ ID NO: 175)
CGGCATTACGGCCGGGGAGTCAAATGTTGTTCGTCCTCACAATCCTGTCCTTCCTCTTGGTGAATCTTG
GCGCCTCGGATCAGCTTAAATATAAACAGTGCTTGGACCCCATAAGCATGGCTGACGTGTTTGTGTGGT
TTTTCTTCCGGGAGGCTAGACGAGATATGGAATGGGATTGGATAGCTGCAACTGCGGCTGAGAAGGCAT
TGGCTGACCCTTCTCTCGAAATGCGGGACTTCTGGAAAGCCAGCAATGGAGAGACACACGTCCGTTTAT
GGGGGCGTCCACTCAATATGGTGATGAAGTTGACAAAAACCCTTCAAGGGTACAGGAAACGTTTTCCAG
ATATCATGAAGATGAAGAGTAAAATATATGGATGCTGGTGCAGGTGCGACCTTAGTGAAACCGTCCTAG
AAACGGTTTGCTTTTTCC Clone 9.1 (SEQ ID NO: 176)
GGGCATTACGGCCGGGGACACTCGAAATGTTGCCCATCCTTGGACTGTTCCTGCTGTTCCTTGGAAATG
TCAACGCTCAGGGGAAAGAACCTTTGCCGAAACGGTGCGAAAAGATCTATGAGAGGTTCATTAAGGAGC TABLE 3-continued

*O. ostertagi* L4 cDNA library screen (with antiserum from protected calves immunised with pool 3 fraction from Trial 3 - see FIG. 1)

ACACCAGAGGTTTGACTTGGAATGACGAACTGGCGTCCGAAGCTTTGGATATGCTGATGCGAGGATATT
CTATGGACTTTTCATATGACTTGAAGCTTCTAGTGTCAGGGACGTTTCCGAATAGTGATAATTCGTCAT
TGGAGGACAAGGTTTCTCTCACCTTGGAAAGTGCCATCTTTACACCAGAA

Clone 10.1 (SEQ ID NO: 177)
CGGCATTACGGCCGGGGTCCACTTCGATGAAATAAATTTCGCAGTTGT

Clone 12.1 (SEQ ID NO: 178)
TCGGCTTACGGCCGGGGTGCGCAAGTATTTCAAAGGTGCTGAAAGCTTCACTGCCGATGACGTCCAAAA
AAGCGATAGGTTTGCCGTCCAAGGTATGGCTCTGCTCACATCCGTGCACATTCTTGCCGACACCTATGA
CAATGAGATGATCTTCCGTGCCTTCGTCCGTGATCTCATGAACCGACATAAGGAGCGAGGACTTGACCC
TAAACTCTGGAAGGACTTCTGGGATATCTTCGAGAAGTTCCTGGAGAACCGCAAGCCACTAACTGCTGA
CCAGAAGACTGCGCTTGATGCGATGGGCACAAGATTCAACGATGAAGCTCAGAAGCAACTGGCCGTCCT
TGGACTTCCACACACATAAGAAACTCTCTTGGGAAATGCCTAGGTCTTGATGCGTCAGTGAATAAAGTG
TTGTCAGCG Clone 13.1 (SEQ ID NO: 179)
TCGGCTTACGGCCGGGGGATGCGCGGTGCATTGGTGCCCTGACATGACATTCGCCGCGTGCGAGTATAA
TCCCGCTGGAAATCTTCTTGGTTCTGTTGTTTACGAAAAAGGAGATCCATGTACAACTGACGCCGACTG
CCAGTGCGAAGGTTGCGTTTGCAGCAGAGATGAGGCGCTATGCATTGCCCCAGCACATTGATTTAGCTG
TCATTCTCAACCCACTTTTTCAAAGTTTGTGTGCTTTGACAGTTTCAAAGGATTCATCAACAGTCAAAT
AAAAGGTTTTAC Clone 14.1 (SEQ ID NO: 180)
CGGCATTACGGCCGGGAGGGAGAGACGAACAGGATGATCACCGAATTGATATTATAAGTGCAGAGAAAG
GAACAGCATCAACAGACCGTGTGACGACACCATTCATGACGAAGTATGAACGCGCTCGAGTTTTAGGTA
CACGTGCTCTTCAGATTGCTATGGGCGCACCGGTGATGGTCGAGTTGGAAGGAGAAACGGATCCACTGG
AAATTGCTCGCAAGGAGCTAAAACATCGACGTATTCCAATCATTGTTCGACGATACCTACCAGATGGCT
CATTTGAAGATTGGTCCGTCGATCAGCTGCATGTGACCGACTGGTGATATGGCTGACCATGTAACTTCT
GTTTCCTGTTACCTTTCTTCTCATACCTGTTGATCTTCATGAGCCTTTTTTTTTACATATTTGGTTATA
TGTTATGTCATATTTGGAGCTATACACACATCCTCCCAGCAATGAAGTGATTGAC Clone 19.1 (SEQ ID NO: 181)
GCATACGGCCGGGGAGGGCTCTGATGTGGTTTGAGCAGTTTTATTCCGGGGTCATTACAATCGCGTTTG
TTGCTGGTGCATGTTATATGAGTTATCCTTTCAATAAATGGGATGTTGGACGAGCCTATCGAAGGGATT
ACTGCACTCCTGCAAGAATTGAGCTGTCGAAGCGTGATCATCGTTTAACTGGGAACCAATATGTCATCT
CCGGTCTGGAATCGATCATCAAATAGATTGTCGGAACTTTTTGATGCTCTGCTAGGTGTTGGAAGATTGG
AGTTTTCTCACTGTCATTGTAGAAGTACATTTGATAACTTTGATTGTGTCGTGTAGCTATAGATTGATG
AATATTAGAATATTT
TTTGGTTTCATCATCGGAATGAAATTCGAACCCT Clone 20.1 (SEQ ID NO: 182)
AGAGCGATGAACGCACGTTATGTGAAGAGCCCAAGACATACTATTCAAGTCGATTACATT
GAATACATGGATGAATTAGCCAGCTTAGTTGGATGCAAGCCGAACATCGCGCAGATTTTC
AAATCAGATCCGATTTTAGCATTACAGCTCTACTTTGGTCCATGCGTTCCGTACGCGTAC
AGGCTGCAGGGGCCTCATCCTTGGTCAGGAGCTCGAGACGCAATAATGACAGTTGATGAAAGAGTGTTC
AAGGCGACAAATTCGAACAGGTACAAGGCCTCCACTGGGTATGGATACATTATCATTGCATCGATACTT
CTTGTTTTGTTGCTTATCCTACTCTTTTAATTATGTACCACA
ACCTTAAAAAGAATATTTTTGC Clone 21.1 (SEQ ID NO: 183)
CGGCATTACGGCCGGGGTTCAGATGACACTGAAAAAGAGCTCGATCTTCATCGGAACTGTCTGCGATAA
TGGAGTCGCAAAGAAAGCTCAAGTACCACCAGAGGCATGCCATCACAAGATCTACCCAGAGATTGGTGA
CAAGTTCTTGGAGATGCTCAGCACCCCCGGCAGCTACGACATGGAAGTGATTGAGAAGGAGGCTCATCA
GTCGAACATCATCAAACTGCCAGCGATCAGCAGCGCTTTGAACAACTTTGTCGTTAAGGGTGACTGGCA
GGCACAGATCGCACTCGTTCTTGGAGGTCAGACAATCGCACATATCAAGGCTCCATCAAATACTGATTG
GCTCTATGTCAACTAGGCCTGGCATTTCATTGGAGTAACACCTAGGCAGTGATTCACTGAAATTCCGCA
ATAAAAAATGAAATATGCAGGAAC Clone 23.1 (SEQ ID NO: 184)
CGGCATTACGGCCGGGTACACAAATCGTGTGCCAGTGATTACGTACAGCAGCTCTCTTTATAATTTCAT
AACCACTGAACTCGAATATCGATACGTTCCTGGACGTCCATCTGCCTAAACGATTTCTGCATATGGACA
CTATTATGGCCATCAGAGTGATAAAGTGCTGAAGTGACTTTTCTGTTGCTAAACTTCGCGGTTTAATAA
AGTTTTTAGTTC Clone 24.1 (SEQ ID NO: 185)
CGGCATTACGGCCGGGGAATGGAATGATACTATCTCTGAACTAGCTAGGCAAGATGTCACGCAACCAGC
AAGCTTATCTTCGGCTATATTGAGAGGTTATGAAGAAGCAAGTGATTGGGTCGATTTTCCACCGAAGGA
TGAACAACCAATGGAGGATAAGGTGAACTCGACAATGCACACAAAGACCTTCAATCAACGTCTGTCAAA
AGTGATAAGTGGTCTAACATGTGACGAAGCTATGTTTGGATGCTACTGCGATTACGGAAGTGGACCGTT
TTCTGACGACATGCAGATCAAGTGTTTCTTCCAATGAGTTTTTCAAATCAGTAAATTTGTGAAATTTTC
ACTGCATGAATGAACTAGAGACAC Clone 25.1 (SEQ ID NO: 186)
TCGGCATTACGGCCGGGGACGCTGAGGGTATTGAACCAGACGATTTGGAGGAGATGTACAAGAAAGCTC
ACGAACGCATTCGAAGTCAACCAGATCATGTTGCTCCAGCTCCTAAGAAAGTCGAGAAAAGAGCTATC
GCATCCATAAGATCAGCTTGGAGGAGAGAAAGAAACGCATTGAGGAGAAGAAAGCGCTGCTCCTGCTAC TABLE 3-continued

*O. ostertagi* L4 cDNA library screen (with antiserum from protected calves immunised with pool 3 fraction from Trial 3 - see FIG. 1)

TGAAGAAACAGCAAGACGCCGCAATGTCGTGAATGCACAAGCTGTTGATTTACAGCAATAAAGTTGTTG
AAGTC

Clone 26.1 (SEQ ID NO: 187)
TCGGCATTACGGCCGGGGGATGAATGGCGAAAAGGCCCTGACGGCTTACCAGGCTCTCCTGGTCAAGCT
GGAACCCCTGGTGAACCCGGCGAGCGTGGAGTTTGTCCAAAATACTGCGCCATTGATGGAGGAGTTTTC
TTTGAAGATGGAACAAGGCGTTAAATTACATCAGATCTTGACATATCAGCAGTTGCTTCTAGGAAATTG
TACCCACCACAAAATAAATGTATTCAAACG Clone 28.1 (SEQ ID NO: 188)
CGGCATTACGGCCGGGGTGAGTGAAAATGTACTGAACACAACAATAAGTGTGTGAAGTACGTGAATCTA
TACTATATATTTTGCGCCTTATTCATAATGTTAGGTGGATTTCGAACGGGA
TTATGAGAGTTGCCTTAACATTTTATCGACCTCATTTGTGGTCGAAATATGAAATTTGTG
TTTCAAATGTCAAATGTTCGTTCAAATTATGCGTAGATATGTCATGTAAATAAATTTCAT
GAACTTCT Clone 30.1 (SEQ ID NO: 189)
GAATCATTGTTTGACGTTCAAGTTCATATAACTAGTGTTTGCTGATGTTTTTTAAACGGT
CATTTATTCATTAGGATGATGATTATTCATTGCTTTGTGAATAAACCTAATAAATAATAT
CAGGTTCCCGCTATTTCTAGCCAATTATTCACCGATATAGGAAGTTGTTGTTACGTTACT
AGCTTTGTAATCTGCTTTGTATGTCATTAAAGAGACTTCCGTATAGTGGCCGTTTTTCAA
AGTTCTCGTGTTATTTTCAGAACAAGTAAAGAATTCTT Clone 32.1 (SEQ ID NO: 190)
TCGGCATTACGGCCGGGACGCTTTCAAAGAAGGCGCGCGTGGAGACGCAGCGACTGATACAACCACAG
CTTCTCGACCTCGGCGCAGTTCAAGCATCAGTTCTCAAAGACAATCTGAACGTTCTAGAGGCGAACGGC
TTCGGATTCGAGTTTAAAGATGGCGATGACGGCTGTACAATCCCTCTGCTAGTCTCCGCACCCGTTCTT
CATAGTTGGCAATTTGATAAAAGCGATATTGAAGAGATCCTAACTGTGGTTTCCGAATTTCCTGGCGTA
ATGTACCGTCCAGCTAAGCTTCGCCGAATATTCGCTTCTAGAGCCCGTCGAAAATCCGTGATGATTGGC
ACAACACTTACCACGGCACAAATGCAAACTATTGTTCATCACCTCGGTACACTGGATCAACCTTGGAAC
TGTCCACATGGTCGCCCAACTCTTCGACATCTCGTTGACTTGCAAAACATAACCTTGTAATGTCTAATC
ACTATTTCACTTCTTAAGTTGCTATTGGAAGTACTAATGAACGATATGTTTACTCATGATTTTCAGTT
CAACAAAGCAAGATTTTGAATATTTATTATGTTCTATAAAAGTTTCAG
TTG Clone 33.1 (SEQ ID NO: 191)
CGGCATTACGGCCGGGTCAGAAGACGAGGATTTATTTACGGAATGGTTGAAGGATACTGCTGGAGTGTC
CTCCAATCATGCTAAGAGTGCGTACAATTGTCTCAATGCGTGGGCGGAGCAATATATCTGATATTGATC
TGCTAATTGAAATGTTTAGTGTGAAAATTGTATGAATTACTA
CTTTTGATTTCATTTGTTCGTATTACGGTTCGTGGAATTCGGTGTGTACGACTTAACTGA
CTTGTTCTAAATTGTGTCAATTTGTCATTTCGATAGGGATGCTCGAATAAACGACTATTT
TC Clone 37.1 (SEQ ID NO: 192)
TATAGAAAATATTGTATTTATTTATACCTTTTATGTTAATTATATTAATTTAATATTTTGTTGTTTTA
TTTAAGTTAATTATAAAAATATTATATAAAAAATAAGTAGAGCT Clone 38.1 (SEQ ID NO: 193)
TCGGCATTACGGCCGGGATCGCAGATCAAGCTTGCGCAAGGATTGGTGAGAAAAAATACCGGCAGGTA
TCTTCCAAAAGCAGCGAACATGTTCAAACTTGTTTATAACTGTTCACTTGAAACGTCAGCTAGAGAAGC
GGCTGACAGATGTACGACCGCCCCATCAACATCACTTCCAAGCGGTGTCAAAGAAAATATCCACAGCGT
TGCGAAGTCGATGGCCCGGTATCGTGTCGATGCTATGAAAGAGGCGGCCAGGTATTGGTGGAAGCAAGT
GAGACTCGTCGATGGAATTGGAATGAAAGTCATATTCAGAGCGAACATGAAAGCAGCCCGATCAGATA
TTTCACTCTAATGGCATGGGCAACCACCAAAACGATAGGGTGTGCTGTTTCTGAAAATTGTGGAAGCGC
ATGGTTCGTGGCGTGCCACTACTATGGGGGAGGAAGTATGGTCGACGATGCCGTTTACGAGAGAGGCAC
GCCATGCTCAGCTTGTCCTACTGGCTACTTCTGCAATGAGATGAAGTTATGTCAATCGGCGAATTGATT
GAATTCGTGCACATTTCTTGTGGTAAATGAAGTTCTTCAGCTCG Clone 39.1 (SEQ ID NO: 194)
CGGCATTACGGCCGGGTGATGAAGGCAGAAATGGAGCGATTAGGTTTCAATCCATATGGCGAACATGCT
GAAAAGCGATTGAAACCCGACTATTCTAATTCGCCTAAGGATAATCCTGCTGCTAAGGCATTTGAGGGT
TTAGAGCAATAAGAATGTTATCAAATATTAAATATGCTTTTT
TGCTTTTATTCATGAGTTGTTAAAATAGGTAGTGAACATTGTAGCATTGTTAGTTTTGTT
CCAGATTGTTATTATTTTTTGTTTTGCACACATGACCTGTATAAAGAGTTGTTGAT Clone 41.1 (SEQ ID NO: 195)
GGATCCAAAGCCGACTGTCCTCACATATCGACTGTCCTCTAATCTTCAGTCATGAAGCTG
GTTGTTCTGGCTATTCTGTTGTGCGCGGCTTATTCTGTGTATGCACAGAACTGTTTCTTA
ATCACTAATCTGAGTGGTGCCACATGGGGAAAGACAGAATTTTATCGTGACGAAGAACTT
CGTGGAAAGATTGAAAGGAAGCTGGAGAAGAAATCGGCATAGACGATACTTTCGTTATGTATTCTGTG
CTGGCGTTTGAGGCAAATAATGAAATTCACGAATCTATTGTGATGGTTCTCATAAAGGATGAGAAGGGA
AAAGTCGATATCTCACTACTTCAAGTATCAGGTGATAACTGATAGGACAACAAAGGAACGAAGAACCTGG
ATTGACGACATGGACGCGCTTAATTTCATGTTAACGATAAGAAAGTGTAAGCTCGTCCCTTCTAGAGGT
TAAAATCCGTTTTGAATGAATGGACATGGAAATAAATTTTCGCAGTC

TABLE 3-continued

O. ostertagi L4 cDNA library screen (with antiserum from protected calves immunised with pool 3 fraction from Trial 3 - see FIG. 1)

Clone 42.1 (SEQ ID NO: 196)
TTACGGCCGGGCAGCAAGTTCAACGAAATATCGTCGAAGCACCAGCACCATGCAAAGCATGCTC Clone 44.1 (SEQ ID NO: 197)
TCGGCATTACGGCCGGGATGGAGCAGAAGGTAAACGCGACAATGCACGGCACTCTTCACCATCAGCTTA
TAACAGCGGTCAAAAATCAACACGCCACTTTTGGATGCTATTGCGAGCTCGTCACTGATAGAAGTGGAT
GGAGCGATATGTTAATCAATTGTTTCTTCAAATGACTCCTTTTTACTTCGGCGACTTTGTCAAATTTAC
TGCATCTAAAATGAAAAAAAAATTTCGCATAA
ACGTTTTTG Clone 45.1 (SEQ ID NO: 198)
GGCATTACGGCCGGGTGGCCATTGGATATCAAAGTTGCTCTGATTGGTTCCTGCACAAATTCTTCATAT
GAGGATATGACTCGAGCTGCATCCATCGCTAAGCAGGCACTTGACAAAGGGTCGAAAGCTAAAACCCTG
TTCACTATCACACCTGGATCGGAACAAGTTCGCGCTACAATTGAAAGGGATGGAATTTCTAAAATTTTC
AGCGACTTCGGAGGAATGGTGCTGGCAAATGCGTGCGGTCCTTGCATTGGACAATGGGATCGCCAAGAT
GTGAAGAAAGGAGAGAAAAATACCATTGTCACATCATATAACCGAAATTTCACTGGAAGAAACGATGCG
AATCCCGCTACACACGGTTTTGTCACATCTCCTGACATTGTTACTGCACTCTCCATTACTGGAAGGCTC
GACTTCGATCCCACAAAAGATCCGATTACTGCACCGGATGGCTCGAAATTCGTGCTCAAGCCTCCAACG
GGAGATGATCTGCCACAGAAGGGGTACGATCCTGGTGAGGATACTTTCCAGTCGCCATCACAATCTGGA
GAGGTTGTGGTCGACCCTAAATCGGATCGTCTGCAACTTCTTCAACCCTTCGATAAGTGGGATGGCAAA
GACCTAGAGGACATGATCATTCTGATCAAAGTCAAAGGAAAGTGCACAACTGATCACATTTCGGCTGCC
GGACCATGGCTGAAATACCGAGGTCATCTTGACAACTTTTCCAACAACTTATTCCTACCAG Clone 46.1 (SEQ ID NO: 199)
GGGCATTACGGCCGGGAAGGAGATCGTGACAGAGACAGGCGAGATCGACGCTACTGACTCATGTGGCTG
TTCGGTGGAATATTCTCCGTGACATTTTGTTATGGTGTTATGGTTGTTCGTAATACTCTGCTCGATTAA
TTATTAAACTCATATTTTTGTTCATGTAGTATTCTTTCGGAA
TTCTAATGATGGTTCTAAGATTTGTTGTGAAGGTTTTCCGTCTGTACGTTCCAAATGGTA
TTCTTTTTTTCGCGCTGAGAATCTTGTCTTTTCTGTTGCCCTATTATTTATAGAGATTG
CAAAGGTCAGTAGCTTTCTTTACAGTTTTCGTTGCAATCATGTCAATAAAAACTTCCTCT
GCTC In a further embodiment, the antigens and/or vaccines/vaccine compositions provided by this invention may comprise proteins and/or peptides comprising sequences encoded by any one of the nucleic acid sequences shown in Table 3.

Table 4, below, identifies some specific proteins/peptides encoded by cDNA sequences comprising the nucleic acid sequences detailed in Table 3.

O. ostertagi L4 cDNA library screen

| Clone | I.D. |
|---|---|
| 1.1 | Chain A, Cekdm7a From *C. elegans*, Complex With H3k4me3 Peptide And Nog |
| 2.1 | Serpentine Receptor, class H family member (srh-214) |
| 4.1 | Unknown |
| 5.1 | Ribosomal Protein, Small subunit family member (rps-13) |
| 6.1 | 17 kDa ES antigen protein |
| 7.1 | putative L3 ES protein |
| 8.1 | AIDA-1b, putative |
| 9.1 | Putative L3 ES protein |
| 12.1 | Globin-like ES protein F6 |
| 13.1 | C-type single domain activation associated secreted protein ASP3 precursor |
| 14.1 | DNA-directed RNA polymerases I, II, and III 14.4 kDa polypeptide |
| 19.1 | Unknown |
| 20.1 | Flavin-containing MonoOxygenase family member (fmo-1) |
| 21.1 | Unknown |
| 23.1 | Metalloprotease I |
| 24.1 | Putative L3 ES protein |
| 25.1 | 60S ribosomal protein L5 |
| 26.1 | Collagen col-34 |
| 28.1 | Nuclear Hormone Receptor family member (nhr-9) |
| 30.1 | Seven TM Receptor family member (str-66) |
| 32.1 | *C. briggsae* CBR-PMS-2 protein |
| 33.1 | Barrier to Autointegration Factor family member (baf-1) |
| 38.1 | Secreted protein 4 precursor |
| 39.1 | Elongation factor Tu homologue precursor |

O. ostertagi L4 cDNA library screen

| Clone | I.D. |
|---|---|
| 41.1 | 17 kDa ES antigen protein |
| 44.1 | *C. briggsae* CBR-CDH-4 protein |
| 45.1 | ACOnitase family member (aco-2) |
| 46.1 | INneXin family member (inx-14) |

Figure 6:
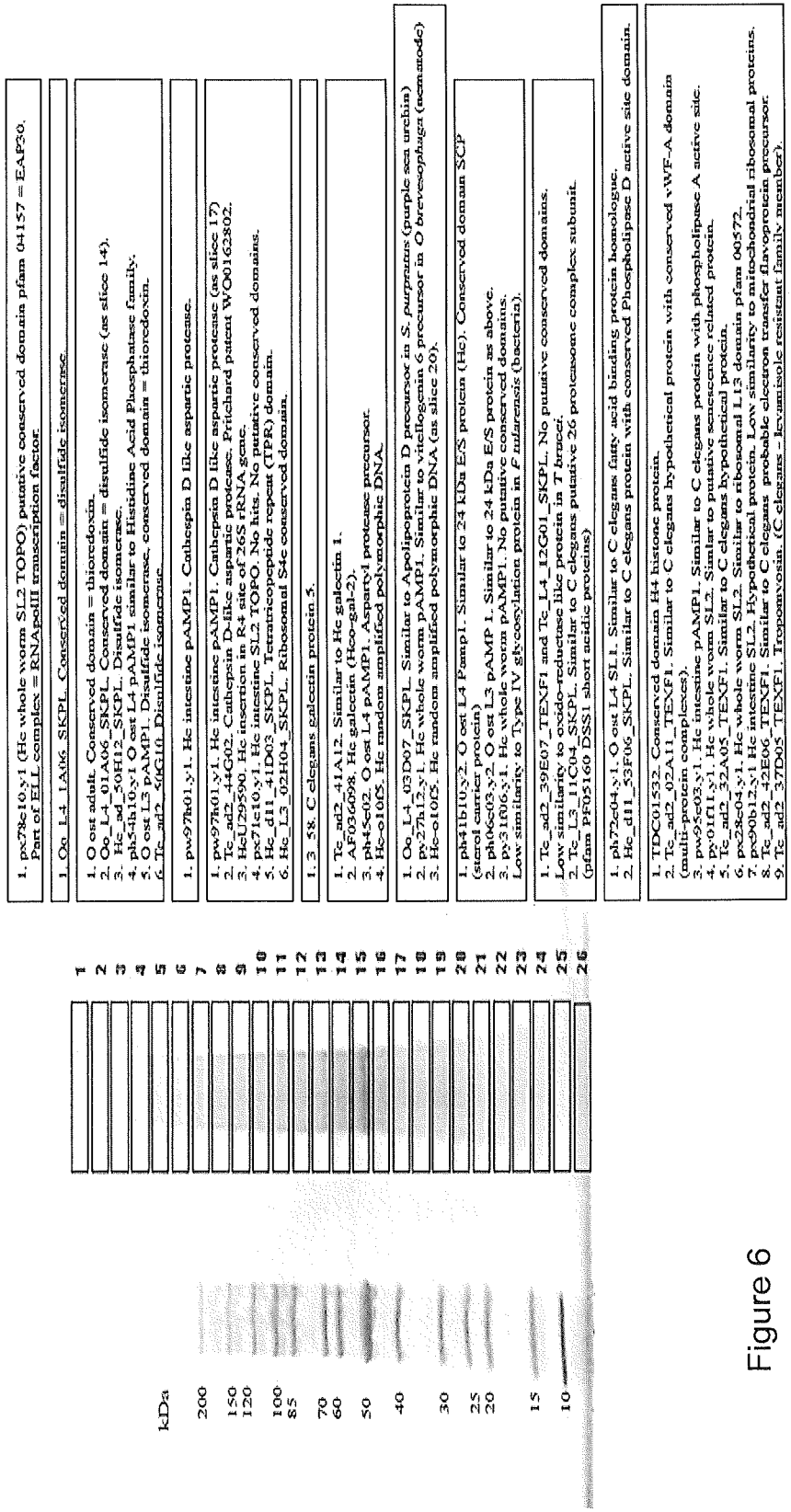
Figure 14:
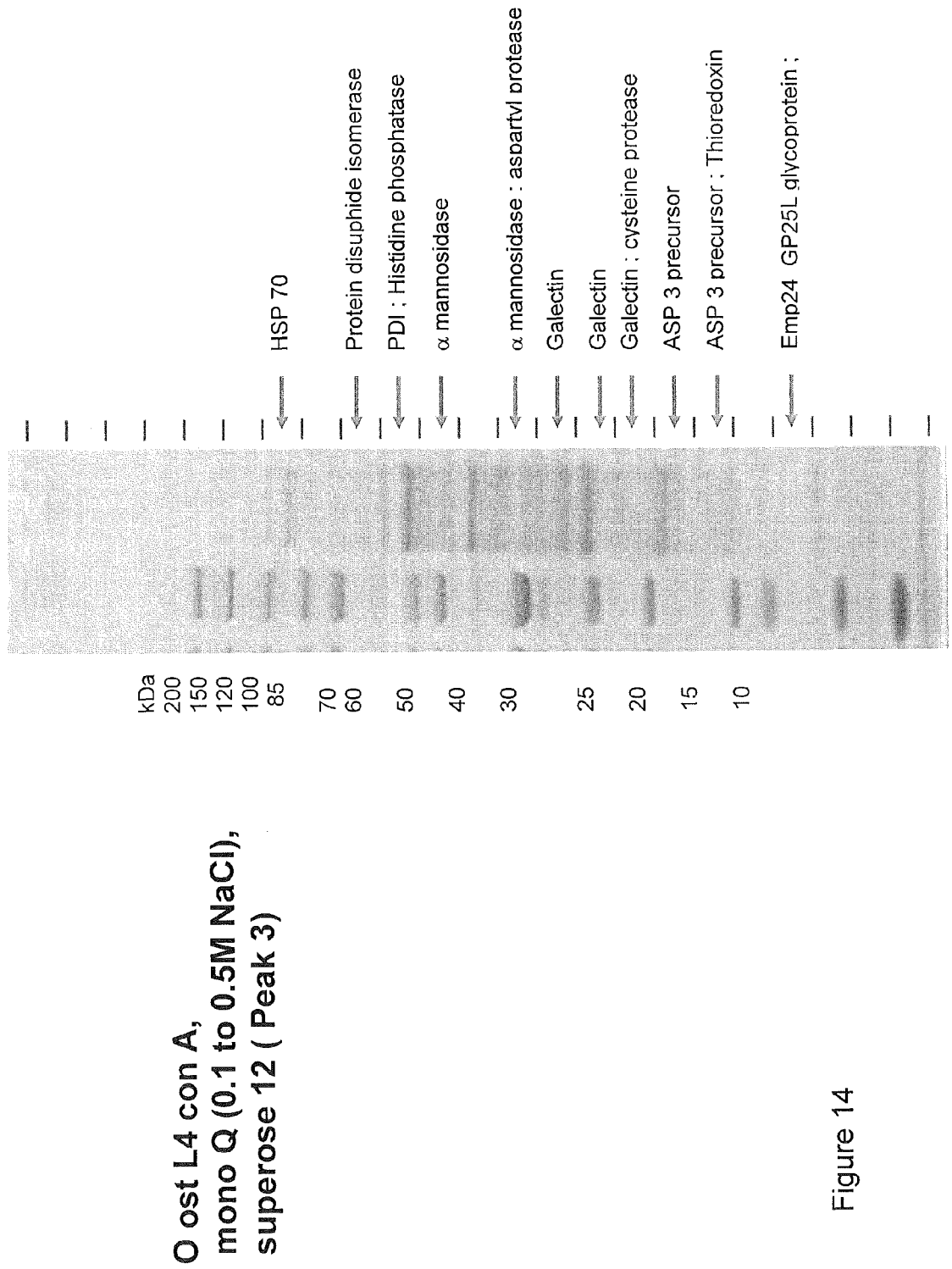

In a further embodiment, the invention relates to one or more of the *Ostertagia ostertagi* antigens identified in FIGS. 6 and 14. These antigens have been identified by mass spectrometry analysis of gel slices obtained from PAGE analysis of L4 antigen preparations obtained in accordance with this invention.

In addition to providing L4 antigens for use in raising immune responses in animals, the present invention may also provide polyclonal and/or monoclonal antibodies (or antigen binding fragments thereof) that bind (or have affinity or specificity for) any of the L4 antigens described herein—including those comprising sequences encoded by the cDNA sequences of Table 1. Production and isolation of polyclonal/monoclonal antibodies specific for protein/peptide sequences is routine in the art, and further information can be found in, for example "Basic methods in Antibody production and characterisation" Howard & Bethell, 2000, Taylor & Francis Ltd. Such antibodies may be used in diagnostic procedures, as well as for passive immunisation.

The present invention further provides a vaccine for use in preventing or controlling disease in bovine hosts caused by non-blood feeding nematode parasites. The vaccine may be a polypeptide or polynucleotide vaccine.

The invention further provides a method for immunising bovine animals against non-blood feeding nematode parasites, said method comprising the step of administering to the bovine a vaccine of the invention.

DETAILED DESCRIPTION OF THE INVENTION

The present invention will now be described in detail with reference to the following figures which show:

FIGURE LEGENDS

FIG. 1. Flow chart of the methods used to prepare the antigen fractions for the calf vaccination trials.

Figure 2:
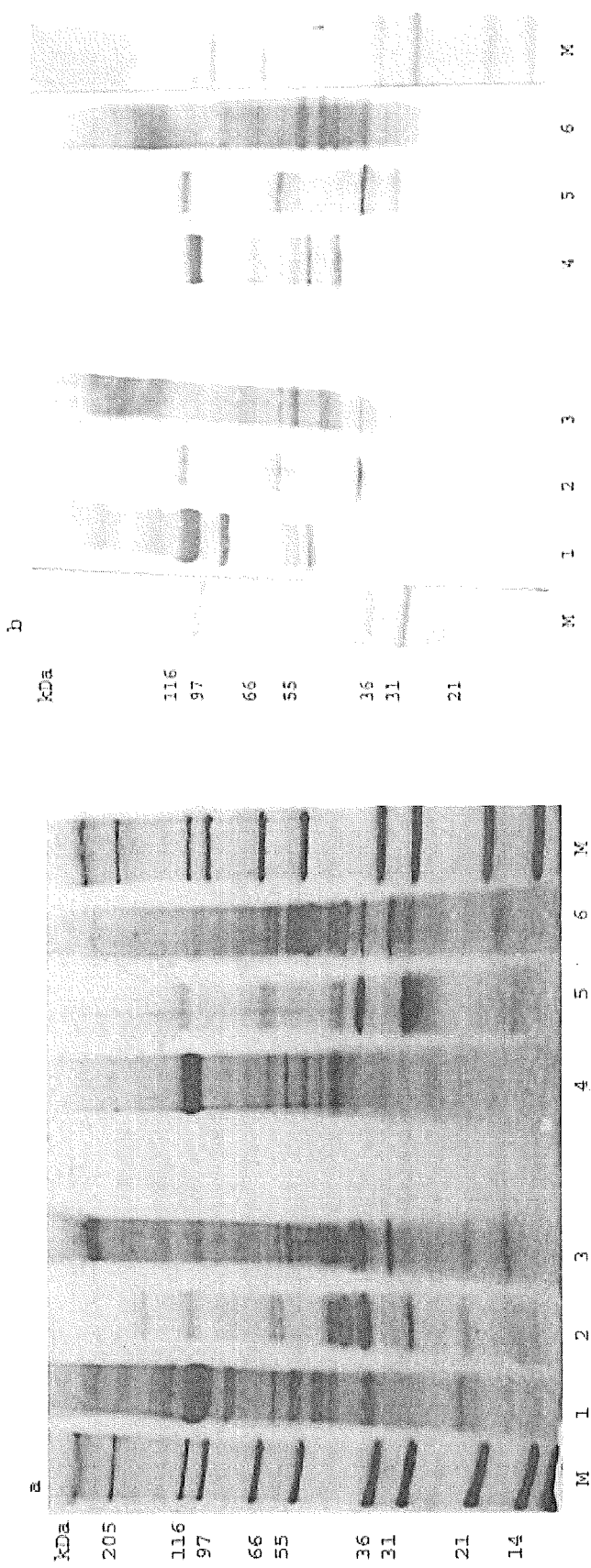

FIG. 2. SDS-PAGE and immunoblot analysis of ConA binding membrane proteins from *H. contortus* and *O. ostertagi*. a, coomassie blue stained. b, Immunoblot probed with sera from calves immunised with ConA binding membrane proteins from adult *O. ostertagi* (Smith [29]). M. molecular weight markers. Lanes 1 and 4, adult *H contortus*; lanes 2 and 5, adult *O. ostertagi*; lanes 3 and 6, L4 *O. ostertagi*. Lanes 1-3, non reducing SDS-PAGE. Lanes 4-6 reducing SDS-PAGE.

Figure 3:
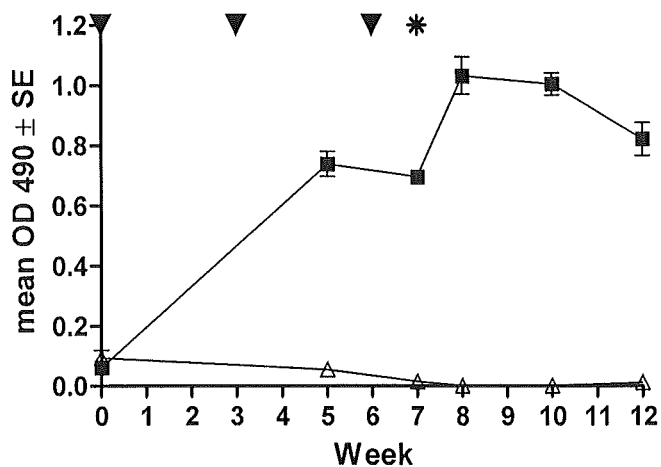

FIG. 3. Kinetics of the antibody response following vaccination of calves with *O. ostertagi* L4 antigens or adjuvant alone in Experiment I. Closed squares=vaccinates; open triangles=controls.

Figure 4:
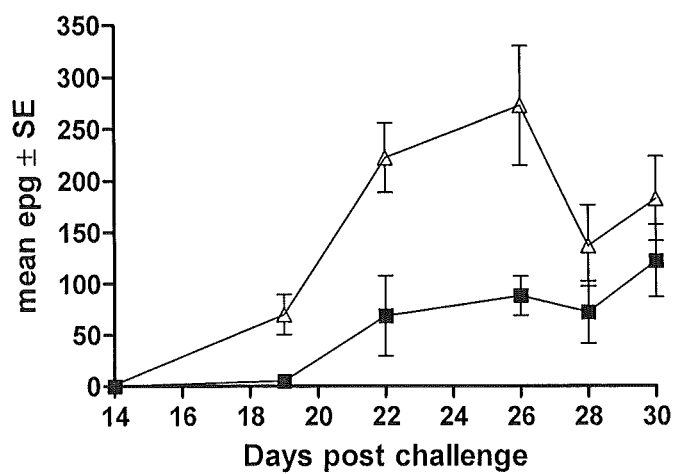

FIG. 4. Group mean faecal egg counts of vaccinated and control calves in Experiment 1. Closed squares=vaccinated animals; open triangles controls. epg=eggs per gram.

Figure 5:
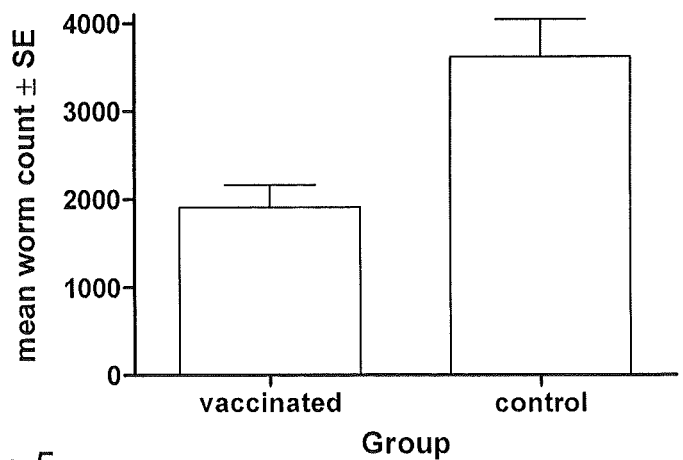

FIG. 5. Group mean worm counts of vaccinated and control calves in Experiment 1.

FIG. 6. Mass spectrometry fingerprint analysis of the protective ConA binding fraction used in Trial 1.

Figure 7:
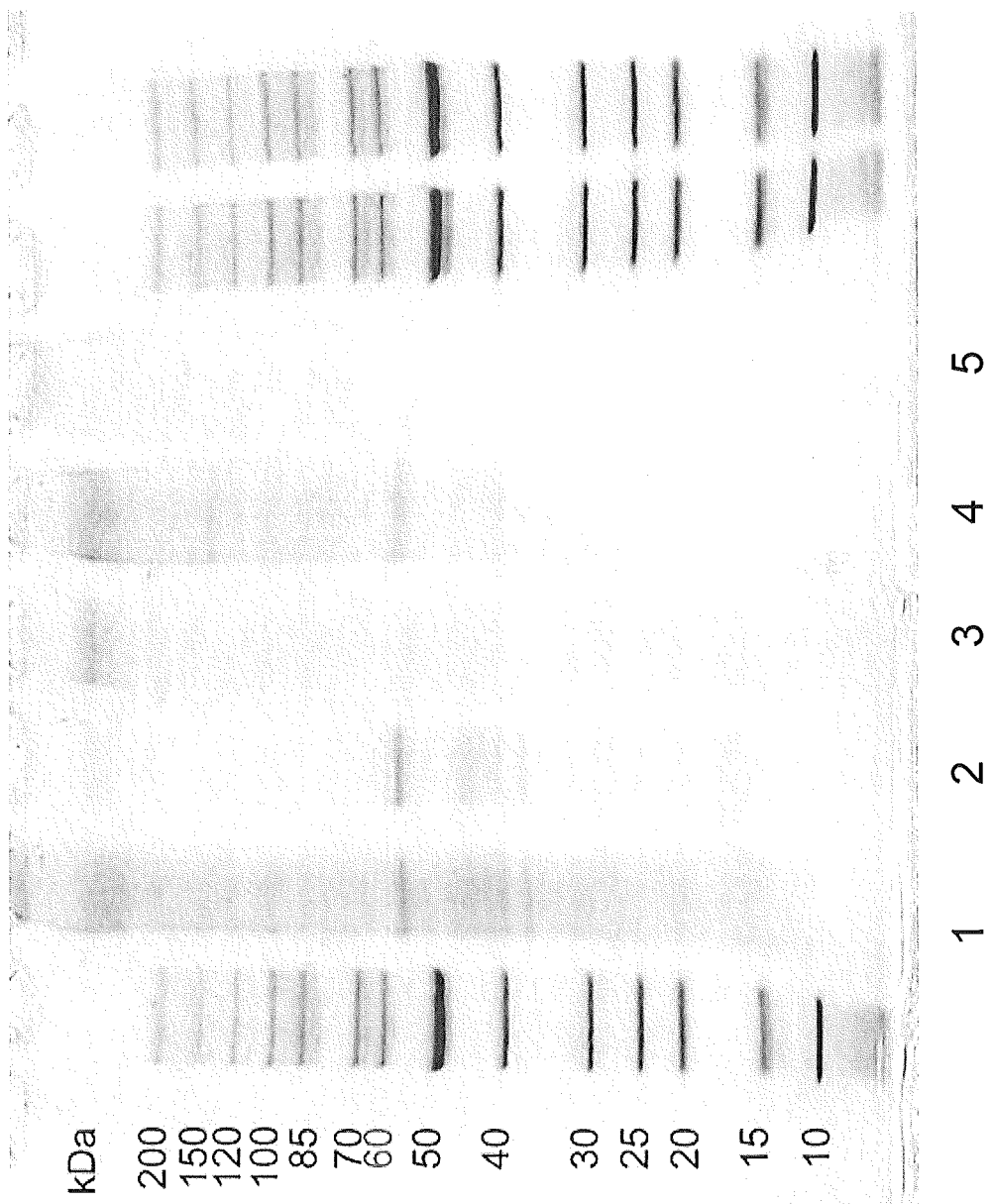

FIG. 7. SDS-PAGE of the preparations used as antigens in Trial 2. Lane 1=ConA binding fraction; lane 2=Pool 1; lanes 3 and 4 were combined to provide Pool 2 and lane 5=Pool 3. The remaining lanes contain molecular weight markers.

Figure 8:
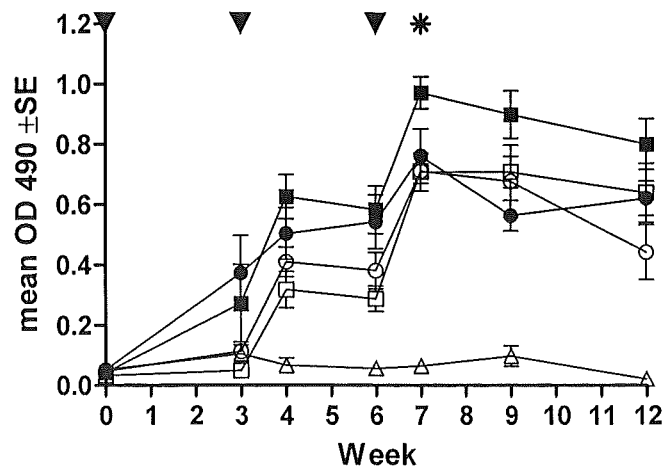

FIG. 8. Kinetics of the antibody response following vaccination of calves with *O. ostertagi* L4 fractions or adjuvant alone in Trial 2. Closed squares=group 2.1. Open squares group 2.2. Closed circles=group 2.3. Open circles=group 2.4. Open triangles=group 2.5 (controls).

Figure 9:
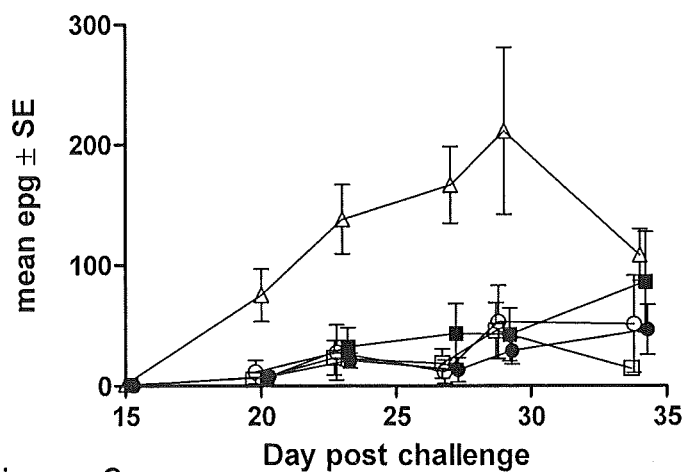

FIG. 9. Group mean faecal egg counts of vaccinated and control calves in Trial 2. Closed squares=group 2.1. Open squares=group 2.2. Closed circles=group 2.3. Open circles=group 2.4. Open triangles group 2.5 (controls). epg=eggs per gram.

Figure 10:
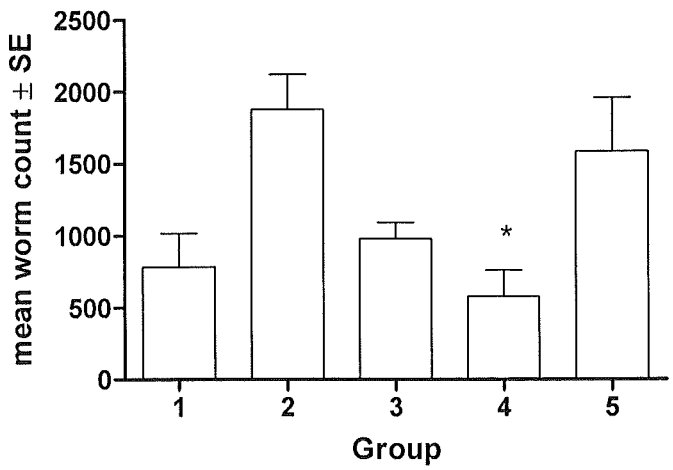

FIG. 10. Group mean worm counts of the calves in Trial 2. *, P<0.05.

Figure 11:
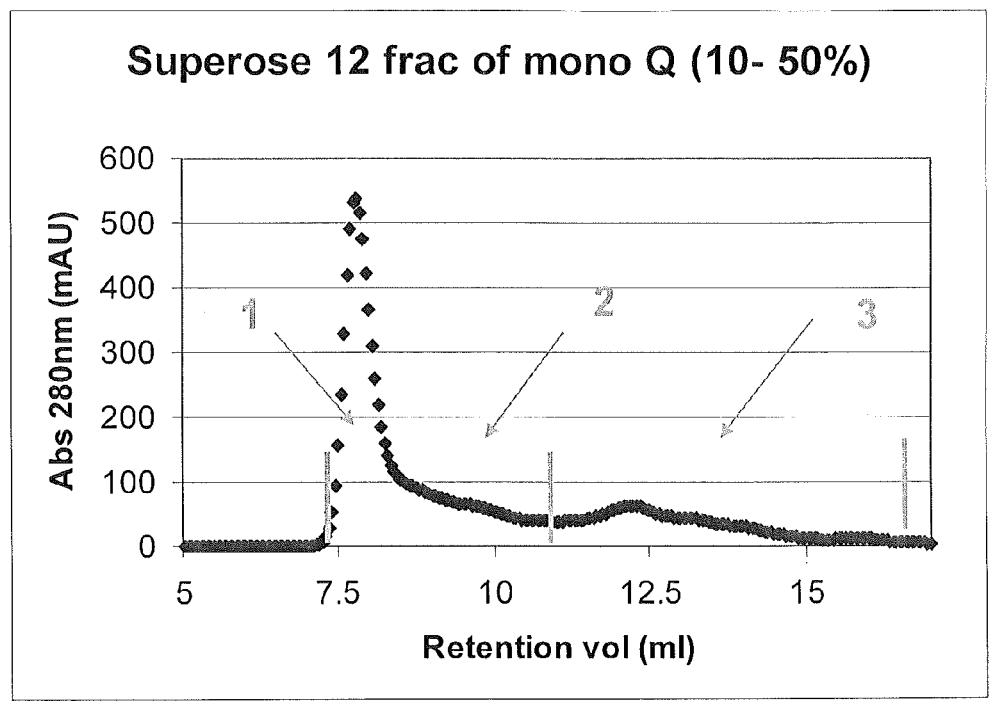
Figure 11:
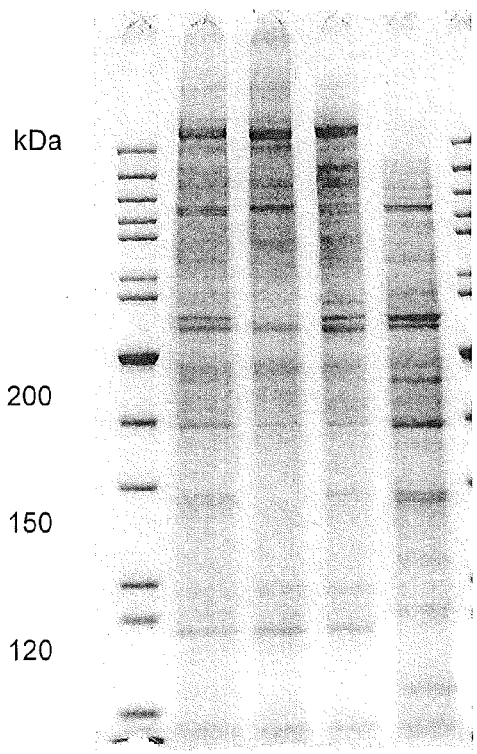

FIG. 11. Chromatography and gel profiles of the preparations used as antigens in Trial 3.

Figure 12:
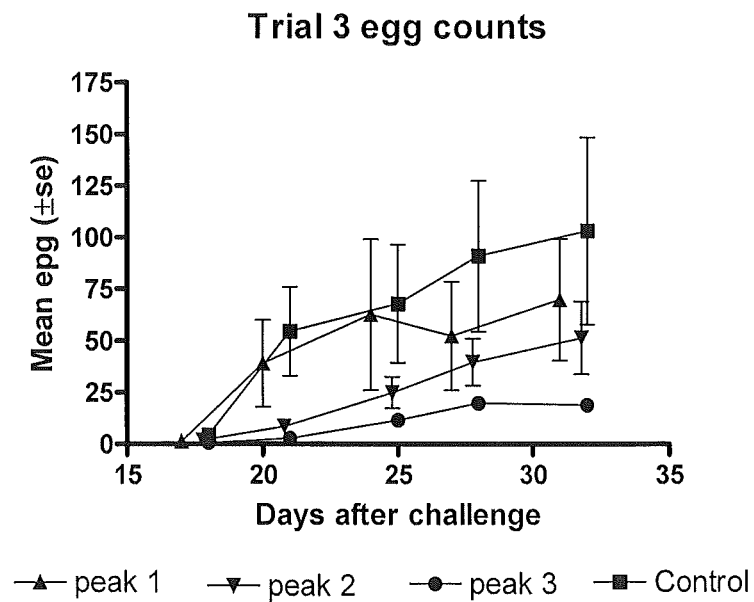
Figure 13:
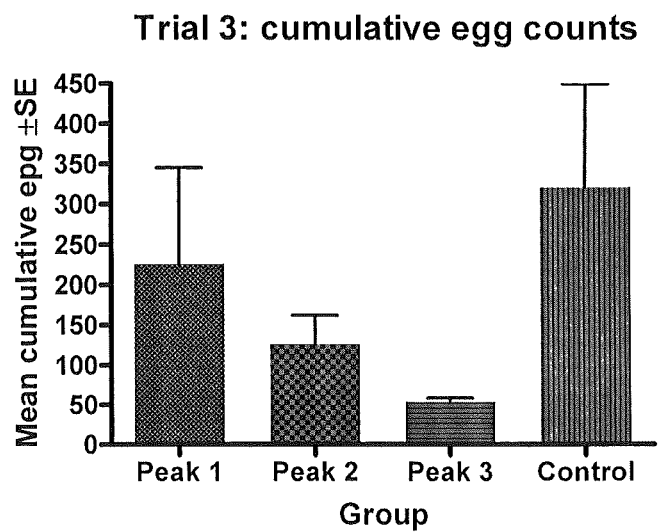

FIG. 12. Group mean faecal egg counts of vaccinated and control calves in Trial 3. epg=eggs per gram. FIG. 13. Group mean cumulative faecal egg counts of vaccinated and control calves in Trial 3. epg=eggs per gram.

FIG. 14. Mass spectrometry fingerprint analysis of the protective Peak 3 fraction used in Trial 3.

Figure 15:
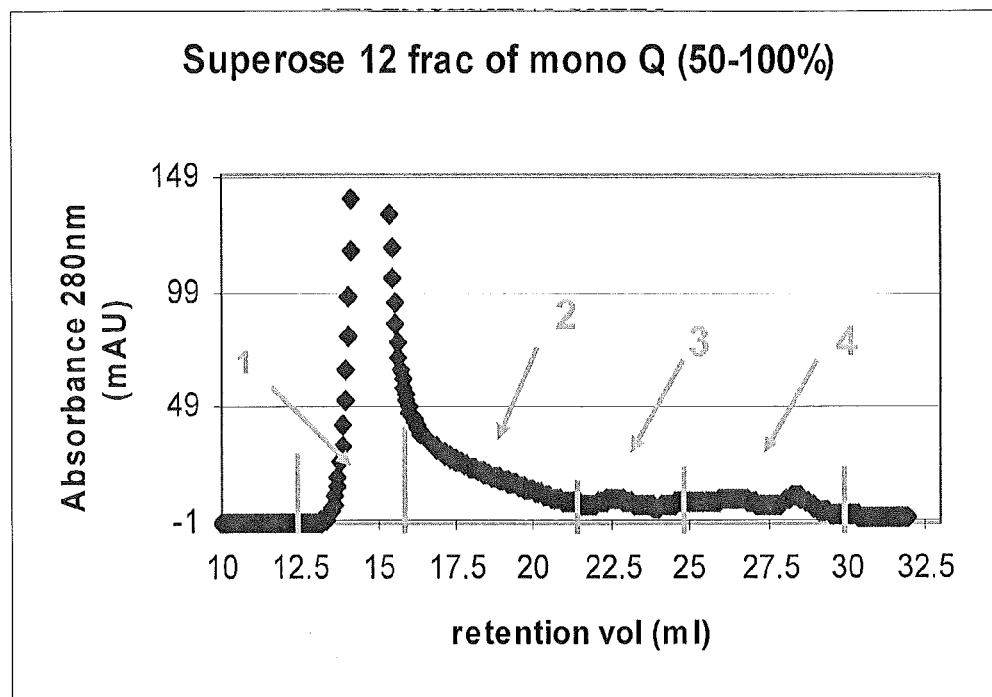
Figure 15:
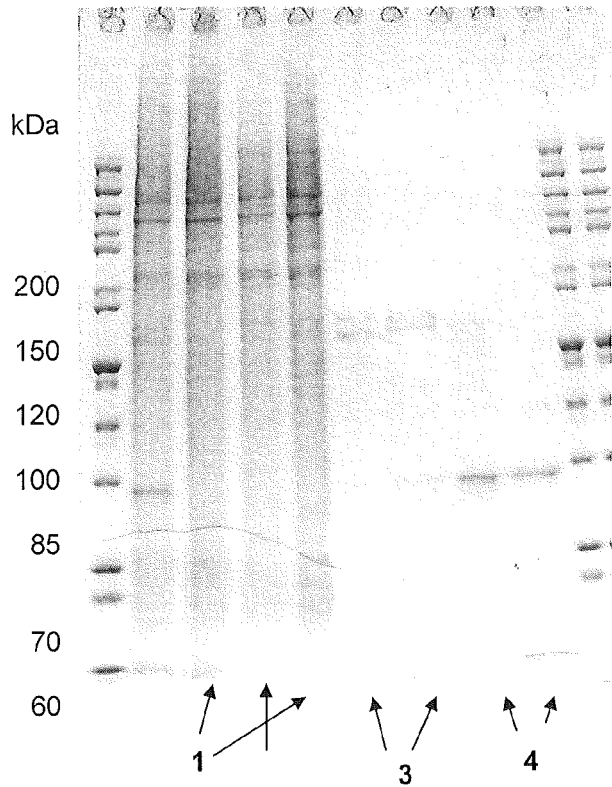

FIG. 15. Chromatography and gel profiles of the preparations used as antigens in Trial 4.

Figure 16:
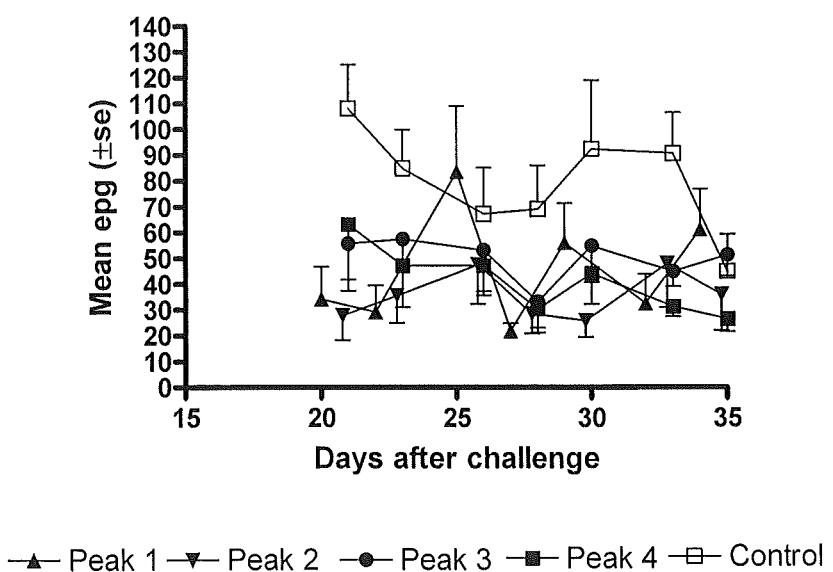

FIG. 16, Group mean faecal egg counts of vaccinated and control calves in Trial 4. epg=eggs per gram.

MATERIALS AND METHODS

Animals

All calves were reared and housed indoors in conditions designed to exclude accidental infection with nematode parasites. Those used as donors for *O. ostertagi* eggs or fourth stage larvae were of various breeds and aged between 3 and 12 months at the time of infection. Those used in the vaccine trials were castrated Holstein-Fresian crosses aged between 6 and 12 months at the start of each trial.

Parasites

Infective larvae were from strains of *O. ostertagi* which have been maintained at Moredun Research Institute for several years.

Parasitological Techniques

The methods for faecal egg counting and enumeration of worm burdens have been described before[31,32]. Fourth stage *O. ostertagi* larvae were harvested from donor calves which had been infected with a single dose of approximately 200,000 L3 seven days earlier. Soon after the animals had been killed by captive bolt and pithing, the abomasums were removed and the contents discarded. After a brief rinse in warm saline, each abomasum was pinned mucosal surface uppermost to a block of polystyrene which was then inverted and floated in a large Baermann funnel containing warm saline. Following four hours at 37° C., fourth stage larvae were drained from the base of the funnel. The funnels were then incubated at 4° C. overnight by which time any larvae still in suspension had settled out and could be drawn off. All larvae were frozen at −70° C. until required for antigen extraction.

SDS-PAGE

Prior to SDS-PAGE samples were heated at 100° C. for 3 min in an equal volume of 63 mM Tris-HCl pH6.8 containing 5% (w/v) SDS, ±10 mM DTT under non-reducing or reducing (10 mM DTT) conditions and separated on 4-12% gradient acrylamide gels (BIORAD, Hercules, Calif., USA). Molecular weight markers (Fermentas, Burlington, Ontario, Canada) were run on each gel and the gels were either stained with coomassie blue R250 (SIGMA, St. Louis, Mo., USA) (0.025% in 40% methanol/10% acetic acid) and destained in 20% methanol/10% acetic acid, or silver stained as follows. After SDS-PAGE the gels were washed 3 times in distilled water, and then fixed overnight in 40% methanol/10% glacial acetic acid. This was followed by incubation for 20 min in 20% methanol/5% acetic acid then 4×15 min washes in distilled water. Gels were then incubated in 50 ml 5 mg/L DTT for 45 min, then for 40 min in 50 ml 0.1% w/v $AgNO_3$, followed by 2 rapid washes in water and 2 washes in 25 ml 3% $Na_2CO_3$. The gels were then developed in 50 ml 3% $Na_2CO_3$ with the addition of 25 µl formalin, and the development stopped after 15 min by adding 20 ml 2.3 M citric acid.

Immunoblotting

SDS-PAGE separated proteins were transferred to PVDF membrane (Millipore, Billerica, Mass., USA) using a semi-dry apparatus. Membranes were blocked in 10% Marvel (Premier Foods International, Spalding, Lincs., UK) in 10 mM Tris, 0.5M NaCl, 0.05% (v/v) Tween-20, 0.02% (w/v) thimerosal (TNTT), the assay diluent and wash buffer, overnight at 4° C. Periodate treatment was carried out by washing the membrane twice, for 20 minutes, in 50 mM NaAc pH 4.5, then incubating for 1 h in 50 mM $NalO_4$/50 mM NaAc, in the dark at room temperature. After further washes of 2×10 minutes in 50 mM NaAc, then 2×10 minutes in TNTT, the membrane was incubated for 30 minutes in 50 mM $NaBH_4$, after which it was washed for 3×10 minutes in TNTT. Membrane strips were incubated with pooled serum samples from each group, diluted 1/300 in TNTT, for 2 h at room temperature. They were then washed 3×5 minutes in TNTT, then incubated with rabbit anti-bovine immunoglobulin horseradish peroxidise conjugated antibody diluted 1/1000 in TNTT (P0159, DAKOcytomation, Glostrup, Denmark).

Protein Concentrations

These were estimated by the bicinchoninic protein assay reagent according to the manufacturer's instructions (Pierce, Thermo Fisher Scientific Inc., Waltham, Mass., USA).

Preparation of Immunogens

Triton X-100 extracts of *Ostertagia* L4 membranes were prepared as detailed for *Haemonchus*[33], and diluted fourfold with 10mM Tris-HC1, 0.5M NaCl, 0.05% $NaN_3$, 10μM $MnCl_2$, 100μM $CaCl_2$, pH 7.4 (Lectin Wash Buffer, LWB). The solution was pumped (8ml/h) at 4° C. through ConcanavalinA (ConA) lectin cross linked to agarose beads (Vector Laboratories, Burlingame, CA, USA) contained in a column. After thorough washing in LWB / 0.5% reduced Triton X-100 the column was eluted with LWB / 0.25% CHAPS / 0.2M methylmannopyranoside / 0.2M methylglucopyranoside (FIG. 1 flow chart). For elution, sufficient sugar solution was pumped onto each column to cover the beads, then the flow was stopped for approximately one hour. The pump was re-started and the peak monitored at $OD_{280}$ was retained as the "1 hour eluate". The elution process was then repeated exactly, except that the flow was stopped overnight to produce an "overnight eluate". The eluates were pooled and passed through a column of Sephadex G-25 to remove the sugar and exchange the buffer to 10mM Tris-HC1, 0.1% CHAPS , pH 7.4 and stored at -70° C. before use as immunogens.

The ConA eluate was fractionated on a MonoQ anion exchange column, 1 ml bed volume (Pharmacia, Pfizer, Kent, UK) equilibrated in 10 mM Tris/0.1% CHAPS pH7.4. The ConA eluate was applied to the column (1 ml/min), and unbound proteins were collected. The bound proteins were eluted by a linear gradient increase in NaCl from 0 M to 1 M over 20 ml, with 10×2 ml fractions being collected. The fractions were then pooled as follows:—Pool 1=unbound material and proteins eluted with up to 0.1M NaCl; Pool 2=fractions eluted between 0.1 and 0.5M NaCl and Pool 3=fractions eluted between 0.5 and 1.0M NaCl (Fig flow chart). Further batches of Pool 2 and 3 material were prepared and fractionated by gel filtration using a Superose 12 column equilibrated with 10 mM Tris, 0.1% CHAPS , 0.5M NaCl pH 7.4 and flowing at 0.5 ml/min. Two hundred ul of Pool 2 containing 0.75 μg of protein was separated in 2 runs was fractionated on a single 30 cm column. Pool 3 was fractionated under identical conditions except two 30 cm columns were coupled in series to improve the resolution.

ELISA for Antibodies to Immunogens

Microtitre plates were coated overnight at 4° C. with 50 μl coating protein per well (ConA eluate), at 0.5 μg/ml in 50 mM sodium bicarbonate buffer, pH 9.6. The plates were washed six times with wash buffer (PBS, 0.05% v/v Tween-20), then incubated with 200 μl 10% (w/v) infasoy (Cow and Gate, Trowbridge, Wiltshire, UK) in TNTT overnight at 4° C. After washing, 50 μl serum per well, diluted 1:2000 in TNTT, were added for 1 h at room temperature. The wells were re-washed and 50 μl peroxidase conjugated rabbit anti-bovine immunoglobulin diluted 1:1000 in TNTT added for 1 h at room temperature. After a final wash, 50 μl o-phenylenediamine dihydrochloride substrate (Sigma) were added to each well. After 10 min in the dark, the colour reaction was stopped by addition of 25 μl 2.5 M sulphuric acid per well and OD values read at 490 nm. Each test sample was assayed in triplicate. Pooled serum taken at the time of challenge from the group of calves in Experiment 2 immunised with the unfractionated ConA eluate was included on each plate as a reference sample, and OD values expressed relative to this value.

Mass Spectrometry Analysis of Protein Fractions

The ConA binding fraction used in Trial 1 and Peak 3 employed in Trial 3 were fractionated by 1-dimensional SDS-PAGE under reducing conditions. Each sample (approximately 10 μg) was mixed with 10 μL, SDS-PAGE sample buffer (0.05 M Tris, pH 6.8 , containing 5% (w/v) SDS, 20% (v/v) glycerol, 0.01% (w/v) bromophenol blue and 10 mm DTT), boiled for 5 mm before loading onto 10% gels with a 3% stacking gel. After protein separation, gels were stained with colloidal Coomassie Blue (SimplyBlue™ SafeStain, Invitrogen), destained in water and the image of each track captured. Mass spectrometry analysis was performed at the Moredun Research Institute's Proteomics Facility. Each gel track was sliced horizontally into about 27 equal gel slices of approximately 2.5 mm each and individual slices were finely chopped (approximately 1 mm3), transferred to clean 0.5 mL Eppendorf tubes and processed using standard in-gel reduction, alkylation and trypsinolysis steps [15]. Digest supernatants of 20 μL final volume were transferred to HPLC sample vials and stored at 4° C. until required for liquid chromatography-electrospray ionization-tandem mass spectrometry (LC-ESI-MS/MS) analysis. Liquid chromatography was performed using an Ultimate 3000 nano-HPLC system (Dionex) comprising a WPS3000 well-plate micro auto-sampler, a FLM-3000flow manager and column compartment, a UVD-3000 UV detector, an LPG-3600 dual-gradient micropump and an SRD-3600 solvent rack controlled by Chromeleon chromatography software. Samples of 4 μL were applied to the column by direct injection. Peptides were eluted by the application of a 15-mm linear gradient from 8% to 45% solvent B (80% acetonitrile, 01% formic acid) and directed through a 3-nL UV detector flow cell. LC was interfaced directly with a 3-D high capacity ion trap mass spectrometer (Esquire HCTplus™, Bruker Daltonics) utilizing a low-volume (50 μL/min maximum) stainless steel nebuliser (Agilent, catalogue number G1946-20260) and ESI. MS/MS analysis was performed as previously described[16]. A peak list file was generated from the resultant data and submitted to a local database server using the MASCOT search engine for protein database searching against NCBInr and Nembase databases. The modifications used in these searches were a global modification of carbamidomethyl (C) and a variable modification of oxidation (M). The tolerances used were; for MS data, 1.5 Da, and for MS/MS data, 0.5 Da.

Matches achieving a significant molecular weight search (MOWSE) score were considered significant if two peptides matched for each protein, each of which had to contain an unbroken b or y ion series of a minimum of four amino acid residues. The other criterion considered in assigning a positive identification for each protein was a concordance between the calculated theoretical molecular mass value of the protein and the observed position of the peptide on 1-D gel electrophoresis. *Ostertagia ostertagi* L4 cDNA library construction and validation This was made in Lambda TriplEX (Clontech) and amplified x 1 according to the manufacturer's instructions. Tenfold dilutions of the unamplified primary library were made in SM buffer over the dilution range $10^{-1}$-$10^{-5}$. A 10 μl aliquot of each dilution was mixed with 200 μl of XL 1-Blue plating cells ($OD_{.600}$=0.5) and incubated for 30 min at 37° C. to allow the phagemids to bind to the cells. After incubation, 4 ml of NZY top agarose at 48° C. was added and the mixture was plated onto pre-warmed 100 mm diameter LB-agar plates. After the top agarose solidified the plates were incubated overnight at 37° C. The $10^{-1}$ dilution plate had 293 plaques, therefore the primary library contained $2.93 \times 10^5$ pfu/ml.

The amplified cDNA library was titrated as above except that the top NZY agarose was supplemented with 100 μl of 100 mM IPTG and 80 μl of 50 mg/ml X-gal to allow the selection of a blue "wild type" phagemid plaque. Several blue plaques were identified and agar plugs containing individual plaques taken into 0.5 ml SM buffer containing 20 µl CHCl₃, to prevent bacterial growth, and stored at +4° C.

The SM buffer supernatant, prepared as above, containing a wild type Lambda TriplEx phagemid was titrated and a dilution that gave near confluent plaques was selected. This clone was plated as above and grown overnight at 37° C. After overnight incubation the plates were flooded with 5 ml of SM buffer and agitated gently on an orbital rocker for 5 h. The resulting suspension of E. coli/phagemid was divided into 1 ml aliquots and subjected to 3 rounds of freezing and thawing (−80° C. for 30 min followed by 37° C. for 5 min) to lyse both the E. coli and phagemid. The resulting lysate was stored at −80° C. until required.

Immunoscreening of cDNA Library

The unamplified primary library was diluted $10^{-1}$ in SM buffer and plated in NZY top agarose onto LB agar plates as above and incubated at 42° C. for 6 h. A nitrocellulose filter, pre-treated with 10 mM IPTG, was placed on top of the top agarose of each plate and incubated at 37° C. overnight. After overnight incubation the plates were transferred to +4° C. for 1 h. The filters were marked to ensure correct orientation later and carefully lifted off the plates. The filters were washed extensively (several changes of TNTT buffer over ~6 h) and blocked overnight in a solution of 1% w/v gelatine in TNTT at +4° C. When immunoscreening using sera from Trial 3 the filters were blocked in TNTT alone, as this was shown to give a lower level of background staining when the blots were developed.

Filters were probed for 1 h at room temperature with pooled serum from the best protected groups (Groups 2.4 and 3.3 see Table 5 and FIG. 1) in trial2 and 3 (diluted to 1/400 in TNTT buffer). The serum had been pre-absorbed as follows:—500 µl was mixed with 500 µl of E. coli/lambda TriplEx freeze/thaw lysate at +4° C. overnight, centrifuged and the supernatant retained for subsequent use. Bovine IgG was detected with a biotin-labelled monoclonal antibody to bovine IgG (Dako) diluted to 1/4000 in TNTT for 1 h at room temperature. In Trial 3 Bovine IgG was detected with a similar antibody (Sigma) diluted to 1/2000

Biotin was detected with Streptavidin-HRPO conjugate (Sigma) diluted 1/2000 or 1/5000 in TNTT for 1 h at room temperature. The filters were washed between each step with 3×5 min washes in TNTT Finally, HRPO activity was revealed with 3,3-diaminobenzidine (SigmaFast, Sigma) prepared as per the manufacturer's instructions.

Immuno-positive plaques were picked into 0.5 ml SM buffer with 20 µl CHCl₃ and subjected to a second round of screening to obtain clones of each positive plaque.

PCR of Insert DNA from Immuno-Positive Clones

The O. ostertagi DNA encoded in the immuno positive clones was amplified by per using primers directed at the pTriplEx vector sequence flanking the cloning site. The primer sequences were;

```
TriplEx Forward:              (SEQ ID NO: 200)
5'-CTC GGG AAG CGC GCC ATT GTG-3'

TriplEx Reverse:              (SEQ ID NO: 201)
5'-TGC GGC CGC ATG CAT AAG CTT G-3'
```

The PCR reaction mixture contained 2 µl of a freeze/thaw lysate prepared from individual immuno-positive clones, as template and 23 µl of a reaction mix containing 1× reaction buffer (Bioline), 5 mM MgCl2, 200 µM dNTPs, 1 µM of each primer and 1 U Taq polymerase per reaction.

The PCR protocol was as follows;

94° 5 min, denaturation

Then 30 cycles of:—

| | |
|---|---|
| 94° | 1 min |
| 64° | 1 min or 54° 2 min |
| 72° | 1 min or 3 min |

Followed by

72° 7 min, sequence extension

PCR products were purified, using a proprietary clean up kit (Qiagen) and sequenced using the Pyrosequencer or sent to Eurofins (MWG) for sequencing Design of Protection Experiments Four immunisation-challenge trials were conducted with weight balanced groups of calves. The number of animals assigned to each group and the dose of antigen each group received is laid out in Table 5.

TABLE 5

Age and weight of the vaccinated calves, the type and dose of antigen administered to each group and summary protection data

| Trial | Age (m) | Wt range (kg) | Group | N | Antigen | Dose/ shot (ug) | mean % Protection eggs | worms |
|---|---|---|---|---|---|---|---|---|
| 1 | 6 to 8 | nd | 1.1 | 7 | ConA | 95 | 60 | 47 |
| | | | 1.2 | 8 | Adjuvant only | 0 | | |
| 2 | 8 to 10 | 155 to 240 | 2.1 | 7 | ConA | 50 | 70 | 51 |
| | | | 2.2 | 7 | Pool 1 | 16 | 85 | 0 |
| | | | 2.3 | 6 | Pool 2 | 19 | 83 | 38 |
| | | | 2.4 | 6 | Pool 3 | 14 | 78 | 63 |
| | | | 2.5 | 7 | Adjuvant only | 0 | | |
| 3 | 10 to 12 | 170 to 360 | 3.1 | 7 | Pool 2 - peak 1 | 25 | 30 | 0 |
| | | | 3.2 | 7 | Pool 2 - peak 2 | 14 | 61 | 0 |
| | | | 3.3 | 7 | Pool 2 - peak 3 | 16 | 83 | 0 |
| | | | 3.4 | 7 | Adjuvant only | 0 | | |
| 4 | 10 to 11 | 175 to 290 | 4.1 | 7 | Pool 3 - peak 2 | 10 | 54 | 13 |
| | | | 4.2 | 7 | Pool 3 - peak 3 | 1 | 35 | 26 |
| | | | 4.3 | 7 | Pool 3 - peak 4 | 2 | 47 | 0 |
| | | | 4.4 | 7 | Adjuvant only | 0 | | |
| | | | | | | mean | 62 | 22 |

FIG. 1 shows a flow chart of how the different immunogen fractions were prepared. All groups were immunised three times at three week intervals and challenged with 50,000 *O. ostertagi* L3 one week later. Immunogens were diluted with cold phosphate buffered saline, pH 7.4, (PBS) and mixed with QuilA (Superfos Biosector) so that each calf received either 20 mg (Trial 1) or 5 mg (Trials 2, 3 and 4) of adjuvant at each immunisation. Control immunogen was prepared identically, except that PBS was substituted for antigen, and administered to all challenge control animals. One ml of immunogen was injected intramuscularly into each side of the neck. All animals were bled at approximately weekly intervals to monitor the kinetics of the antibody response. Details of antigens, dose and numbers of animals are given in Table 5.

Statistical methods

Arithmetic group means are shown throughout with their standard errors. Significant differences between groups were calculated by the t test in Trial 1 and by analysis of variance followed by Tukey's test in Trials2, 3 and 4. To satisfy Bartlett's test for equal variances the egg data i was log transformed prior to analysis.

Results

Yield of Fourth Stage Larvae and ConA Binding Membrane Proteins

Recovery of fourth stage *O. ostertagi* larvae from donor calves ranged from 5% to 20% of the dose given. The yield of ConA binding membrane proteins was approximately 0.3 mg per 100,000 fourth stage larvae.

Comparison of L4 and Adult ConA Binding Proteins

ConA binding integral membrane proteins, prepared in the same way from adult *Haemonchus* conforms or fourth and adult stages of *O. ostertagi* were compared by gel analysis and western blotting. Coomassie stained gels indicated differences in the profiles of all three fractions (FIG. 2a), although additional bands present in the L4 but not in the adult *O. ostertagi* preparations were of most interest in this case. When the three ConA binding fractions were probed with anti-sera from calves which had been immunised with material obtained in the same way from adult *Ostertagia*, additional bands were still detected in the L4 fraction (FIG. 2b).

Digesta from a worm free calf was treated in exactly the same way as the L4s, but no protein peak was detected when the ConA column was eluted with sugar (not shown).

Protective capacity of glycoproteins from *O. ostertagi* L4s

Trial 1: Immunisation with the ConA Lectin Binding Fraction

1a) Antigen Used for Immunisation.

The gel profile of the preparation used to immunise the vaccinated calves in Trial 1 was very similar to that shown in FIG. 2 lane 3.

1b) Antibody Response

Serum antibody titres in the control group remained at background concentrations throughout (FIG. 3). In contrast, a marked response was observed in the vaccinated group by week 5, two weeks after the second vaccination. This response reached a peak on week 8 two weeks after the third immunisation.

1c) Egg and Worm Counts

Mean egg counts of the immunised calves were always lower than controls throughout the experiment, although the difference was not statistically significant on Days 28 and 30 (FIG. 4). However the group means of the cumulative eggs per gram over Days 19 to 30 were significantly different (P=0.01), with the vaccinated animals shedding 60% fewer eggs. Significantly (P<0.01) fewer worms were recovered from the vaccinates (1909±252) compared to the controls (3621±414 and FIG. 4). Small numbers of early fourth stage larvae were found in some calves but no difference between vaccinates and controls was observed.

1d) Identity of Components in the Protective Fraction by Mass Spectrometry.

This is shown in FIG. 6

Trial 2: Immunisation with Sub Fractions of the ConA Lectin Binding Glycoproteins.

This trial was done partly to determine whether the level of protection detected in the first trial could be improved if fractions were prepared which were more enriched for the protective components but also to find out whether simpler fractions could be equally protective.

2a Antigens used for Immunisation

A flow chart depicting how these preparations were made is shown in FIG. 1, the details relating to which calves received which fraction and the dose of protein administered are presented in Table 5 whereas the SDS-PAGE profiles of the immunogens are shown in FIG. 7.

2b) Antibody Response

The kinetics of the antibody responses of each group is shown in FIG. 8. All vaccinated groups showed a similar antibody response to *O. ostertagi* L4 antigen, and had a significantly (P<0.01) higher antibody titres compared to the control group from one week after the second immunisation until the end of the experiment.

2c) Egg and Worm Counts

All four vaccinated groups showed significantly reduced egg counts compared to the adjuvant only control group from Day 20 to Day 29 (FIG. 9). The group means of the cumulative egg counts over Days 19 to 34 were significantly lower in each of the vaccinated groups compared to the controls, with the corresponding percentage protection ranging from 70 to 85% as detailed in Table 5. Only Group 4 showed a significant reduction in worm burden at necropsy, with 64% fewer worms than the control group (FIG. 10 and Table 5).

2d) Identification of components in the best protected group by cDNA library screening. The sequences and, where possible, the corresponding identities of 135 immuno positive clones selected by the calves immunised with the pool 2 fraction are shown in Tables 1 and 2

Trial 3: Immunisation with Sub-Fractions of the 0.1 to 0.5M MonoQ pool.

The object of this trial was to separate the protective antigens identified by Group 2.2 by gel filtration in order to narrow the identity of the candidate protective polypeptides. (No attempt was made to do this for the unbound fraction as too little protein was available for the task)

3a) Antigens Used for Immunisation.

The peaks separated by gel filtration together with an SDS PAGE analysis of the polypeptides present in each of the three antigen pools used to immunise the calves are shown in FIG. 11. Details of the groups and doses of protein administered are laid out in Table 5.

3b) Egg and Worm Counts

The kinetics of the group mean egg counts of the calves in Trial 3 are shown in FIG. 12 and the cumulative counts are presented in FIG. 13. The mean egg output of the calves immunised with Peak 3 was consistently lower than the control calves with an overall reduction of 83% (Table 5). However, there was a large variance in the egg output of the control calves in this trial so this difference just failed to be statistically significant (P=0.056). The number of worms recovered from any of the vaccinated groups and the control group was very similar (Table 5).

3c) Identity of the Components in Peak 3, the Most Protective of the Pool3 Sub-Fractions.

Ten μg of the Peak 3 fraction was separated by SDS-PAGE and subjected to mass spectrometry as described in the Methods. About 16 polypeptide bands were visible FIG. 14. Twelve significant identities were obtained ranging from about 18 to 110 kDa in molecular weight and these are listed in FIG. 14.

3d) Identification of Components in the Best Protected Group by cDNA Library Screening.

The sequences and, where possible, the corresponding identities of 46 immuno positive clones selected by the calves immunised with the pool 3 fraction are shown in Tables 3 and 4.

Trial 4: Immunisation with Sub Fractions of the 0.1 to 0.5M MonoQ pool

As before the object of this trial was to determine whether the components responsible for the protection in Group 3.3 could be separated with a view to simplifying their identity.

4a) Antigens Used for Immunisation.

The peaks separated by gel filtration together with an SDS PAGE analysis of the polypeptides present in each of the three antigen pools used to immunise the calves are shown in FIG. 15. Details of the groups and doses of protein administered are laid out in Table 5.

4b) Egg and Worm Counts

The kinetics of the group mean egg counts of the calves in Trial 4 are shown in FIG. 16 and the overall protective effects are summarised in Table 5. The mean egg outputs of all four groups of immunised calves were lower than the controls but there was little to choose between the efficacy of the different fractions.

Discussion

There was little doubt that the ConA binding fraction of fourth stage *O. ostertagi* membrane extracts contained protective antigens, since all the groups vaccinated with this antigen or one of its derivatives had lower egg counts than their respective controls. As a crude measure, the mean percent reduction in egg output of all 11 groups immunised with this preparation or sub-fractions of it was 62%. More impressively, three of these fractions reduced cumulative egg counts by more than 80% (Table 5). The effect against worm numbers was more variable however, and did not necessarily correlate with the degree of egg reduction (Table 5). However, the two best fractions did reduce worm numbers by 50% or more (Table 5).

These protection figures were better than those achieved with the same ConA binding extract of adult *O. ostertagi* where eggs were only reduced by between 30 and 50% and there was no measurable effect against worm numbers (Smith et al 2000). These results support the hypothesis developed in the Introduction that fourth stage *O. ostertagi* were likely to be more susceptible to the gut antigen approach to vaccination than their adult counterparts and that gut membrane antigens sourced from this developing stage are likely to be more efficacious. This idea does not seem to have been mooted before and could have general applicability to various other non-blood feeding nematode parasite genera across a range of hosts.

Obtaining large numbers of fourth stage *O. ostertagi* is a laborious and expensive procedure. The trials reported here were made possibly by a regular supply of donor calves which were scheduled to be culled anyway after having been the subject of unrelated studies at the Institute.

Because it was not possible to obtain the L4s without some contaminating digesta, the possibility existed that plant material was the source of some of the bands present in the antigen preparations. This possibility was discounted when attempts to make similar preparations from worm free abomasal digesta did not yield any protein. Presumably the cellulose cell walls of the plant cells which make up the bulk of the digesta are resistant to Triton extraction.

Another possibility was that some of the L4 preparation polypeptides, which were additional to those observed in similar preparations from adult worms, were bovine in origin—perhaps from small pieces of abomasal tissue leaching from the mucosa when it was being incubated at 37 C to recover the larvae. However, an immunoblot developed with serum from calves immunised with *O. ostertagi* proteins revealed that several of these bands could not have been bovine proteins.

This discovery of apparently novel bands in the L4 fraction prompted a protection trial. The encouragingly positive result from the first vaccine experiment lead onto 3 further "fractionate and vaccinate" trials where the overall objective was to determine whether simpler fractions containing fewer components would be just as if not more efficacious. It was striking how little native protein was actually required to achieve a good level of protective immunity (Table 5), but because of the difficulty and expense of obtaining large numbers of *Ostertagia* L4s, synthetic antigens, probably derived by recombinant DNA techniques, will be essential for a commercial vaccine. Obviously, the cDNAs of the protective polypeptides are required to do this and some progress was made in that direction through a combination of mass spectrometry and cDNA library immunoscreening. Much remains to be done however before a single protective antigen can be identified.

REFERENCES (1) Armour, J. A. and Ogbourne, C. P. Bovine ostertagiasis: a review and annotated bibliography. Miscellaneous publication No 7 of the Commonwealth Institute of Parasitology, Commonwealth Agricultural Bureaux, England. 1982;

(2) Jackson, R., Rhodes, A. P., Pomroy, W. E., Leathwick, D. M., West, D. M., Waghorn, T. S., and Moffat, J. R. Anthelmintic resistance and management of nematode parasites on beef cattle-rearing farms in the North Island of New Zealand. N Z Vet J 2006; 54 (289-296.

(3) Suarez, V. H. and Cristel, S. L. Anthelmintic resistance in cattle nematode in the western Pampeana Region of Argentina. Veterinary Parasitology 2007; 144 (1-2): 111-117.

(4) Familton, A. S., Mason, P., and Coles, G. C. Anthelmintic-resistant Cooperia species in cattle. Vet Rec 2001; 149 (23): 719-720.

(5) Waghorn, T. S., Leathwick, D. M., Rhodes, A. P., Jackson, R., Pomroy, W. E., West, D. M., and Moffat, J. R. Prevalence of anthelmintic resistance on 62 beef cattle farms in the North Island of New Zealand. N Z Vet J 2006; 54 (6): 278-282.

(6) Gasbarre, L. C, Smith, L. L., Lichtenfels, J. R., and Pilitt, P. A. The identification of cattle nematode parasites resistant to multiple classes of anthelmintics in a commercial cattle population in the US. Proceedings of the 49th American Association of Veterinary Parasitologists, Pennsylvania. Proceedings of the 49th American Association of Veterinary Parasitologists, Pennsylvania 2004; Abstract 44 (55

(7) Anziani, O. S., Suarez, V., Guglielmone, A. A., Warnke, O., Grande, H., and Coles, G. C. Resistance to benzimidazole and macrocyclic lactone anthelmintics in cattle nematodes in Argentina. Veterinary Parasitology 2004; 122 (4): 303-306.

(8) Fiel, C. A., Saumell, C. A., Steffan, P. E., and Rodriguez, E. M. Resistance of *Cooperia* to ivermectin treatments in grazing cattle of the Humid Pampa, Argentina. Veterinary Parasitology 2001; 97 (3): 213-219.

(9) Stafford, K. and Coles, G. C. Nematode control practices and anthelmintic resistance in dairy calves in the south west of England. Vet Rec 1999; 144 (24): 659-661.

(10) Coles, G. C., Watson, C. L., and Anziani, 0. S. Ivermectin-resistant *Cooperia* in cattle. Vet Rec 2001; 148 (9): 283-284.

(11) Coles, G. C. Anthelmintic resistance in cattle. Cattle Practice 2004; 12 (177-179.

(12) Demeler, J., Van Zeveren, A. M. J., Kleinschmidt, N., Vercruysse, J., H-glund, J., Koopmann, R., Cabaret, J., Claerebout, E., Areskog, M., and von Samson-Himmelstjerna, G. Monitoring the efficacy of ivermectin and albendazole against gastro intestinal nematodes of cattle in Northern Europe. Veterinary Parasitology In Press, Corrected Proof (

(13) Love, S. C. and Coles, G. C. Anthelmintic resistance in sheep worms in New South Wales, Australia. Vet Rec 2002; 150 (3): 87

(14) van Wyk, J. A., Malan, F. S., and Randles, J. L. How long before resistance makes it impossible to control some field strains of *Haemonchus contortus* in South Africa with any of the modern anthelmintics? Veterinary Parasitology 1997; 70 (1-3): 111-122.

(15) Waller, P. J., Echevarria, F., Eddi, C., Maciel, S., Nari, A., and Hansen, J. W. The prevalence of anthelmintic resistance in nematode parasites of sheep in Southern Latin America: General overview. Veterinary Parasitology 1996; 62 (3-4): 181-187.

(16) Bartley, David J., Jackson, Elizabeth, Johnston, Kelly, Coop, Robert L., Mitchell, George B. B., Sales, Jill, and Jackson, Frank. A survey of anthelmintic resistant nematode parasites in Scottish sheep flocks. Veterinary Parasitology 2003; 117 (1-2): 61-71.

(17) Armour, J. A. *Ostertagia ostertagi* infections in the bovine: field and experimental studies. PhD thesis, University of Glasgow. 1967;

(18) Burger, H. J. and Pfeiffer, A. [Experimental vaccination of calves with irradiated larvae of *Ostertagia ostertagi* and *Cooperia oncophora*]. Zentralbl Veterinarmed B 1969; 16 (4): 357-367.

(19) Herlich, H. and Douvres, F. W. Gastrointestinal nematode immunization trials in cattle. Am J Vet Res 1979; 40 (12): 1781-1782.

(20) Hilderson, H., Berghen, P., De Graar, D. C., Claerebout, E., and Vercruysse, J. Immunisation of calves with *Ostertagia ostertagi* fourth stage larval antigens failed to protect calves from infection. International Journal for Parasitology 1995; 25 (6): 757-760.

(21) Geldhof, P., Claerebout, E., Knox, D., Vercauteren, I., Looszova, A., and Vercruysse, J. Vaccination of calves against *Ostertagia ostertagi* with cysteine proteinase enriched protein fractions. Parasite Immunol 2002; 24 (5): 263-270.

(22) Geldhof, P., Vercauteren, I., Gevaert, K., Staes, A., Knox, D. P., Vandekerckhove, J., Vercruysse, J., and Claerebout, E. Activation-associated secreted proteins are the most abundant antigens in a host protective fraction from *Ostertagia ostertagi*. Molecular and Biochemical Parasitology 2003; 128 (1): 111-114.

(23) Vercauteren, Isabel, Geldhof, Peter, Vercruysse, Jozef, Peelaers, Iris, Van Den Broeck, Wim, Gevaert, Kris, and Claerebout, Edwin. Vaccination with an *Ostertagia ostertagi* Polyprotein Allergen Protects Calves against Homologous Challenge Infection. Infect Immun 2004; 72 (5): 2995-3001.

(24) Geldhof, P., Vercauteren, I., Vercruysse, J., Knox, D. P., Van Den, Broeck W., and Claerebout, E. Validation of the protective *Ostertagia ostertagi* ES-thiol antigens with different adjuvantia. Parasite Immunol 2004; 26 (1): 37-43.

(25) Meyvis, Y., Geldhof, P., Gevaert, K., Timmerman, E., Vercruysse, J., and Claerebout, E. Vaccination against *Ostertagia ostertagi* with subfractions of the protective ES-thiol fraction. Veterinary Parasitology 2007; 149 (3-4): 239-245.

(26) Smith, W. D. and Zarlenga, D. S. Developments and hurdles in generating vaccines for controlling helminth parasites of grazing ruminants. Veterinary Parasitology 2006; 139 (4): 347-359.

(27) Smith, W. D. Prospects for vaccines of helminth parasites of grazing ruminants. International Journal for Parasitology 1999; 29 (1): 17-24.

(28) Newton, S. E. and Munn, E. A. The Development of Vaccines against Gastrointestinal Nematode Parasites, Particularly *Haemonchus contortus*. Parasitology Today 1999; 15 (3): 116-122.

(29) Smith W. D., Smith, S. K., and Pettit, D. Evaluation of immunization with gut membrane glycoproteins of *Ostertagia ostertagi* against homologous challenge in calves and against *Haemonchus contortus* in sheep. Parasite Immunology 2000; 22 (5): 239-247.

(30) Rose, J. H. The development of the parasitic stages of *Ostertagia ostertagi*. J Helminthol 1969; 43 (1): 173-184.

(31) Smith, W. D. and Smith, S. K. Evaluation of aspects of the protection afforded to sheep immunised with a gut membrane protein of *Haemonchus contortus*. Res Vet Sci 1993; 55 (1): 1-9.

(32) Murray, J. and Smith, W. D. Ingestion of host immunoglobulin by three non-blood-feeding nematode parasites of ruminants. Res Vet Sci 1994; 57 (3): 387-389.

(33) Smith, W. D., Smith, S. K., and Murray, J. M. Protection studies with integral membrane fractions of *Haemonchus contortus*. Parasite Immuno) 1994; 16 (5): 231-241.

(34) Borgsteede FHM. Editor. Facts and Reflections III. Workshop on "arrested development of nematodes in sheep and cattle" Lelystad, the Netherlands, May 1978. Published by the Central Veterinary Institute, Lelystad. the Netherlands.

The invention claimed is:

1. A method of raising an immune response in an animal, said method comprising administering an immunogenic amount of one or more L4 antigens, said L4 antigens being from a fourth lifecycle (L4) stage larvae of non-blood feeding parasitic nematodes, wherein the L4 antigens are isolated using a method comprising the steps of:
   obtaining a cell membrane protein preparation from the L4 stage larvae of a non-blood feeding parasitic nematode;
   contacting the cell membrane protein preparation with an affinity matrix comprising concanavalin A (ConA) under conditions which permit binding between the affinity matrix and L4 antigens present in the cell membrane protein preparation;
   washing the matrix to remove any unbound material; and
   eluting bound L4 antigens with a suitable elution solution/buffer.

2. The method of claim 1, wherein the L4 antigens are specifically expressed by L4 stage larvae of non-blood feeding parasitic nematodes and not at other lifecycle stages.

3. The method of claim 1, wherein the non-blood feeding parasitic nematode parasite is selected from a species within the genera consisting of *Ostertagia, Teladorsagia, Trichostrongylus, Nematodirus, Cooperia, Chabertia, Oesophagostomum* and *Ascaris*.

4. The method of claim 1, wherein the L4 antigens are isolated from L4 stage larvae of *Ostertagia ostertagi*.

5. The method of claim 1, wherein the L4 antigens comprise one or more of the antigens selected from the group consisting of:
   (i) antigens encoded by cDNA sequences having or comprising a cDNA sequence selected from the group consisting of SEQ ID NOS:1-198 and 199; and
   (ii) ConA binding proteins and/or peptides from L4 stage *Ostertagia ostertagi*.

6. The method of claim 1, wherein the one or more L4 antigen(s) are admixed with another component.

7. A vector comprising a nucleic acid sequence, wherein said nucleic acid sequence is a cDNA sequence selected from the group consisting of SEQ ID NOS:1-198 and 199, or a sequence having at least 60% identity or homology with a cDNA sequence selected from the group consisting of SEQ ID NOS:1-198 and 199.

8. A host cell transformed with the vector of claim 7.

9. A method for the production of a recombinant L4 protein or peptide for use in raising an immune response in an animal, said method comprising the step of (a) transforming a host cell with a nucleic acid sequence, wherein said nucleic acid sequence is a cDNA sequence selected from the group consisting of SEQ ID NOS:1-198 and 199, or a sequence having at least 60% identity or homology with a cDNA sequence selected from the group consisting of SEQ ID NOS:1-198 and 199, or transfecting a host cell with the vector of claim 7; (b) culturing the cells obtained in (a) under conditions in which expression of the protein takes place; and (c) isolating the expressed recombinant protein or peptide from the cell culture or/and the culture supernatant.

10. A method of preparing a vaccine and/or vaccine composition comprising one or more antigens from the fourth lifecycle (L4) stage larvae of non-blood feeding parasitic nematodes, for use in raising an immune response in an animal, said method comprising the steps of:
   (a) obtaining a cell membrane preparation from L4 stage larvae of a non-blood feeding parasitic nematode; and
   (b) contacting the cell membrane protein preparation with an affinity matrix under conditions which permit binding between the affinity matrix and antigens present in the cell membrane preparation;
   wherein the antigens released or separated from the affinity matrix are used to prepare a vaccine or vaccine composition.

11. The method of claim 10, wherein the affinity matrix comprises ConA.

12. The method of claim 10, further comprising the step of contacting antigens released or separated from the affinity matrix with Sephadex G-25 to remove carbohydrate.

13. The method of claim 1, wherein the L4 antigen is a glycoprotein, protein and/or peptide comprising a-linked mannose.

14. The method of claim 1, wherein the cell membrane preparation from L4 stage larvae of non-blood-feeding parasitic nematodes is obtained by subjecting the L4 stage larvae to lysis protocols to fragment the cell membrane and the fragmented membrane is collected by centrifugation.

15. The method of claim 1, wherein the cell membrane preparation from L4 stage larvae of a non-blood-feeding parasitic nematode is a TRITON X-100 extract of membranes from L4 stage larvae of non-blood-feeding parasitic nematodes.

16. The method of claim 1, wherein the suitable elution solution/buffer is a carbohydrate solution.

17. The method of claim 1, wherein L4 antigens eluted are subjected to further purification procedures.

18. The method of claim 17, wherein the further purification procedures comprise an anion exchange or gel filtration procedure.

19. The method of claim 17, wherein the further purification procedures comprise contacting the eluted L4 antigens with Sephadex G-25 to remove carbohydrate.

20. A method of raising an immune response in an animal, said method comprising administering an immunogenic amount of one or more L4 antigens, wherein the L4 antigens comprise one or more antigens selected from those encoded by cDNA sequences having or comprising a cDNA sequence selected from the group consisting of SEQ ID NOS:1-198 and 199, or a sequence having at least 60% identity or homology with a cDNA sequence selected from the group consisting of SEQ ID NOS:1-198 and 199.

21. The method of claim 20, wherein the L4 antigens comprise one or more antigens encoded by cDNA sequences having or comprising a cDNA sequence selected from the group consisting of SEQ ID NOS:14, 18, 19, 67, 68 and 86.

22. A method of immunizing or vaccinating an animal, said method comprising administering an immunogenic amount of one or more L4 antigens, wherein the L4 antigens comprise one or more antigens selected from those encoded by cDNA sequences having or comprising a cDNA sequence selected from the group consisting of SEQ ID NOS:1-198 and 199, or a sequence having at least 60% identity or homology with a cDNA sequence selected from the group consisting of SEQ ID NOS:1-198 and 199.

23. The method of claim 22, wherein the L4 antigens comprise one or more antigens encoded by cDNA sequences having or comprising a cDNA sequence selected from the group consisting of SEQ ID NOS:14, 18, 19, 67, 68 and 86.

24. The vector of claim 7, wherein said nucleic acid sequence is a cDNA sequence selected from the group consisting of SEQ ID NOS:14, 18, 19, 67, 68 and 86.

* * * * *

UNITED STATES PATENT AND TRADEMARK OFFICE
CERTIFICATE OF CORRECTION

PATENT NO. : 9,078,841 B2  
APPLICATION NO. : 13/516909  
DATED : July 14, 2015  
INVENTOR(S) : Smith et al.

Page 1 of 1

It is certified that error appears in the above-identified patent and that said Letters Patent is hereby corrected as shown below:

IN THE SPECIFICATION

Column 1, Line 33: Please correct "Europe $^{(9,10,11,12)}$, However,"
to read -- Europe $^{(9,10,11,12)}$. However, --

Column 4, Line 35: Please correct "FIGS. 1 and 5."
to read -- FIG. 1 and Table 5. --

Column 39, Line 21: Please make an indention at the beginning of line 21 so that it begins a new paragraph.

Column 39, Line 51: Please begin a new paragraph at "FIG 13. Group"

Column 42, Line 22: Please correct "FLM-3000flow manager"
to read -- FLM-3000 flow manager --

Column 47, Line 50: Please correct "O. ostertagi"
to read -- *O. ostertagi* --

Column 48, Lines 9-10: Please correct "However, an immunoblot developed"
to read as a continuing sentence as follows:
-- However, and immunoblot developed --

Column 48, Line 11: Please correct "*O, osteragi*"
to read -- *O. osteragi* --

Signed and Sealed this  
Fifth Day of July, 2016

Michelle K. Lee  
*Director of the United States Patent and Trademark Office*